(12) United States Patent
Smallheer et al.

(10) Patent No.: US 10,577,383 B2
(45) Date of Patent: Mar. 3, 2020

(54) MACROCYCLIC INHIBITORS OF MYELOPEROXIDASE

(71) Applicant: BRISTOL-MYERS SQUIBB COMPANY, Princeton, NJ (US)

(72) Inventors: Joanne M. Smallheer, Yardley, PA (US); Ellen K. Kick, Pennington, NJ (US); Meriah Neissel Valente, Bedminster, NJ (US); Carol Hui Hu, New Hope, PA (US); Oz Scott Halpern, Robbinsville, NJ (US); Sutjano Jusuf, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/099,010

(22) PCT Filed: Jun. 26, 2017

(86) PCT No.: PCT/US2017/039228
§ 371 (c)(1),
(2) Date: Nov. 5, 2018

(87) PCT Pub. No.: WO2018/005336
PCT Pub. Date: Jan. 4, 2018

(65) Prior Publication Data
US 2019/0177340 A1    Jun. 13, 2019

Related U.S. Application Data

(60) Provisional application No. 62/355,494, filed on Jun. 28, 2016.

(51) Int. Cl.
*C07D 519/00* (2006.01)
*A61P 9/10* (2006.01)

(52) U.S. Cl.
CPC ............ *C07D 519/00* (2013.01); *A61P 9/10* (2018.01)

(58) Field of Classification Search
CPC ........................... C07D 471/04; C07D 519/00
See application file for complete search history.

(56) References Cited

FOREIGN PATENT DOCUMENTS

| WO | WO2016040417 A1 | 3/2016 |
| WO | WO2016040419 A1 | 3/2016 |
| WO | WO2017040451 | 3/2017 |

OTHER PUBLICATIONS

Roth, Aaron et al. "Inhibition of myeloperoxidase: Evaluation of 2H-indazoles and 1H-indazolones", Biooriganic & Medicinal Chemistry, vol. 22(2), pp. 6422-6429 (2014).

*Primary Examiner* — Noble E Jarrell
(74) *Attorney, Agent, or Firm* — Elliott Korsen

(57) ABSTRACT

The present invention provides compounds of Formula (I): wherein the substituents are as defined in the specification, and compositions comprising any of such novel compounds. These compounds are myeloperoxidase (MPO) inhibitors and/or eosinophil peroxidase (EPX) inhibitors, and may be useful for for the treatment and/or prophylaxis of atherosclerosis, heart failure, chronic obstructive pulmonary disease (COPD), and related diseases.

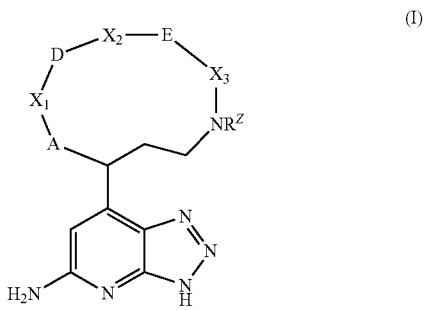

5 Claims, No Drawings

MACROCYCLIC INHIBITORS OF MYELOPEROXIDASE

CROSS REFERENCE TO RELATED APPLICATION

This application claims the priority of U.S. Provisional Application Ser. No. 62/355,494 filed Jun. 28, 2016 which is herein incorporated by reference.

FIELD OF THE INVENTION

The present invention relates to novel macrocyclic compounds, which are myeloperoxidase (MPO) inhibitors and/or eosinophil peroxidase (EPX) inhibitors, compositions containing them, and methods of using them, for example, for the treatment and/or prophylaxis of atherosclerosis, heart failure, chronic obstructive pulmonary disease (COPD), and related diseases.

BACKGROUND OF THE INVENTION

Cardiovascular disease is a major health risk throughout the industrialized world. Atherosclerosis, the most prevalent of cardiovascular diseases, is the principal cause of heart attack and stroke, and thereby the principal cause of death in the United States. Atherosclerosis is a complex disease involving many cell types and molecular factors (for a detailed review, see Weber et al., Nature Med, 17(11):1410-1422 (2011)).

MPO inhibitors have been suggested to reduce the atherosclerotic burden and/or the vulnerability of existing atherosclerotic lesions and thereby decrease the risk of acute myocardial infarction, unstable angina or stroke, and reduce ischemia-reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al., J. Clin. Invest., 94(1):437-444 (1994)). Moreover, HOCl-modified lipoproteins have been detected in advanced human atherosclerotic lesions (Hazed, L. J. et al., J. Clin. Invest., 97:1535-1544 (1996)). In eroded and ruptured human lesions, as compared to fatty streaks, an increased number of MPO expressing macrophages have been demonstrated, suggesting a particular role for MPO in acute coronary syndromes (Sugiyama, S. et al., Am. J. Pathol. 158(3):879-891 (2001); Tavora, F. R., BMC Cardiovasc. Disord., 9:27 (Jun. 23, 2009)).

Data accumulated during the last fifteen years indicate that the pro-atherogenic actions of MPO include oxidation of lipoproteins, induction of endothelial dysfunction via consuming nitric oxide and destabilization of atherosclerotic lesions by activation of proteases (Nicholls, S. J. et al., Arterioscler. Thromb. Vasc. Biol., 25(6):1102-1111 (2005); Nicholls, S. J. et al., JLR, S346-S351 (2009)). Several studies have focused on nitro- and chlorotyrosine modifications of LDL and HDL lipoproteins. Since chlorotyrosine modifications in vivo are generated by hypochlorous acid produced by MPO these modifications are regarded as specific markers of MPO activity (Hazen, S. et al., J. Clin. Invest., 99(9):2075-2081 (1997)).

ApoA-I isolated from atherosclerotic lesions is modified by reactive chlorine and nitrogen species as well as by reactive carbonyls (Pennathur, S. et al., J. Biol. Chem., 279:42977-42983 (2004); Shao, B. et al., J. Biol. Chem., 279:7856-7866 (2004); Zheng, L. et al., J. Clin. Invest., 114(4):529-541 (2004); Shao, B. et al., IBC in press (2012)). Chlorotyrosine modification of apoA1, the main apolipoprotein of HDL cholesterol, was associated with impaired cholesterol acceptor function (Bergt, C. S. et al., Proc. Natl. Acad. Sci. USA, 101(35):13032-13037 (2004); Zheng, L. et al., J. Clin. Invest., 114(4):529-541 (2004)). Thus, oxidation of apoA-I amino acid residues by the MPO-$H_2O_2$—$Cl^-$ system is one mechanism for loss of its biological activities.

The lipid and protein content of LDL are also targets for MPO oxidation and presence of chlorotyrosine in LDL extracted from human atherosclerotic tissues has been shown (Hazen, S. et al., J. Clin. Invest., 2075-2081 (1997)). LDL particles exposed to MPO in vitro become aggregated, leading to facilitated uptake via macrophage scavenger receptors and foam cell formation (Hazell, L. J. et al., Biochem. J, 290 (Pt. 1):165-172 (1993); Podrez, E. A. et al., J. Clin. Invest. 105:1095-1108 (2000)). Thus, MPO appears to play a role in the generation of oxidized LDL, which contributes to atherosclerosis plaque development.

Further evidence implicating MPO in the pathophysiology of atherosclerosis comes from the study of hMPO transgenic mice crossed with LDL-R KO mice (Castelini L. W. et al., J. Lipid Res., 47:1366-1377 (2006)). These mice expressed MPO in lesions and developed significantly larger aortic lesions than control LDL-R KO mice.

Many clinical studies have implicated MPO in cardiovascular disease in human patients. Patients with established coronary artery disease have higher plasma and leukocyte MPO levels than healthy controls (Zhang, R. et al., JAMA, 286(17):2136-2142 (2001)). Moreover, in three large prospective studies plasma levels of MPO predicted the risk of future coronary events or revascularization (Baldus, S. et al., Circulation, 108(12):1440-1445 (2003); Brennan, M. et al., N. Engl. J. Med., 349(17):1595-1604 (2003); Kohli, P. et al., Circulation, 122:A13175 (2010)). In two recent large nested case control prospective studies, the EPIC-Norfolk and MONICA-/KORA Augsburg studies, baseline MPO levels in these initially healthy populations turned out to be an excellent predictor of future risk of CAD and CHD respectively, showing that this inflammatory marker precedes the presentation of clinical symptoms of CVD (Meuwese, M. C. et al., J. Am. Coll. Cardiol., 50:159-165 (2007); Karakas et al., J. Int. Med., 271:43-50 (2011)). Interestingly, MPO deficient humans are less affected by cardiovascular disease than controls with normal MPO levels (Kutter, D. et al., Acta Haematol., 104:10-15 (2000)). A polymorphism in the MPO promoter affects expression leading to high and low MPO expressing individuals. In three different studies the high expression genotype has been associated with an increased risk of cardiovascular disease (Nikpoor, B. et al., Am. Heart J. 142(2):336-339 (2001); Makela, R. et al., Lab. Invest. 83(7):919-925 (2003); Asselbergs, F. W. et al., Am. J. Med., 116(6):429-430 (2004)).

MPO inhibitors are expected to preserve heart function and reduce heart failure burden in patients. In MPO null mice, preservation of left ventricular (LV) function has been observed in both a coronary artery ligation model (Askari, A. T. et al., J. Exp. Med., 197:615-624 (2003)) and an ischemia reperfusion model (Vasilyev, N. et al., Circulation, 112:2812-2820 (2005)), suggesting that MPO may provide a mechanistic link between inflammation, oxidant stress, and impaired cardiac remodeling. High circulating levels of MPO have also been linked to chronic heart failure in patients. Systemic MPO was increased in patients with established chronic systolic HF and correlated with diastolic dysfunction independent of age and plasma B-type natriuretic peptide (Tang, W. H. et al., *Am. J. Cardiol.*, 98:796-799 (2006)). Studies also showed that systemic MPO in subjects with myocardial infarction (MI) (Mocatta, T. J. et al., *J. Am. Coll. Cardiol.*, 49:1993-2000 (2007)) or chronic systolic HF (Tang, W. H. et al., *J. Am. Coll. Cardiol.*, 49:2364-2370 (2007)) may predict long-term adverse clinical events.

Inhibitors of MPO or EPX may be used to treat other neuroinflammatory diseases, including multiple sclerosis, Alzheimer's disease, Parkinson's disease, multiple system atrophy, and stroke as well as other inflammatory diseases or conditions like asthma, COPD, cystic fibrosis, inflammatory bowel disease, chronic kidney disease, renal glomerular damage and rheumatoid arthritis.

In these chronic inflammatory diseases, a role of MPO in the development of tissue injury has been suggested. In lesional tissues of patients with Alzheimer's disease, MPO protein was detected along with elevated levels of chlorotyrosine (Green, P. S. et al., *J. Neurochem.*, 90:724-733 (2004)). In an animal model of Parkinson's disease, increased levels of chlorotyrosine and HOCl-modified proteins in brain tissues have been reported (Choi, D. K. et al., *J. Neuroscience*, 25(28):6394-6600 (2005)). In asthmatic patients the level of bromotyrosine, a molecular fingerprint of eosinophil-catalyzed oxidation was associated with symptom severity (Wedes, S. H. et al., *J. Pediatr.*, 248-255 (2011)). Upon allergen challenge, a model that elicits primarily a strong eosinophilic response, lung segments of asthmatic subjects exhibit a >10 fold increase in bronchio-alveolar lavage 3-bromotyrosine an indicator of eosinophil activity vs. a 3-fold increase in 3-chlorotyrosine characteristic of MPO activity (Wu, W. et al., *JCI*, 105:1455-1463 (2000)). The presence of HOCl-modified protein was also detected in patients with membranous glomerulonephritis (Grone et al., *Lab. Invest.*, 82:5-14 (2002)). High MPO circulating levels have been implicated in the development of cardiovascular and chronic kidney disease in patients on hemodialysis (Honda, H. et al., *Clin. J. Am. Soc., Nephrol.*, 142-151 (2009). In addition MPO activity and 3-chlorotyrosine levels were also increased during hemodyalisis in patients with end-stage renal disease (Delporte, C et al., *Talanta*, 99:603-609 (2012)). Similarly, there is accumulation of neutrophils and eosinophils in conjunction with MPO and EPX seen in intestinal mucosa of patients with inflammatory bowel disease (Kruidenier, L. et al., *J. Pathol.*, 201:17-27 (2003); Carlson, M. et al., *Am. J. Gastrol.*, 94(7):1876-1883 (1999)) and in synovial fluids of rheumatoid arthritis patients (Edwards, S. W. et al., *Biochem. J.*, 250:81-85 (1988); Nucombe, H. L. et al., Ann. Rheum. Dis., 50:237-242 (1991)).

Thus, there is considerable evidence that MPO and/or EPX derived oxidants contribute to tissue injury in chronic inflammatory disorders. MPO and/or EPX inhibitors are anticipated to reduce the levels of oxidants and tissue injury associated with the progression of these diseases.

SUMMARY OF THE INVENTION

The present disclosure provides novel triazolopyridine compounds, including stereoisomers, tautomers, pharmaceutically acceptable salts, or solvates thereof, which are useful as MPO inhibitors and/or EPX inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of diseases or disorders associated with the activity of MPO and/or EPX.

The compounds of the invention may be used in therapy.

The compounds of the invention may be used for the manufacture of a medicament for the treatment and/or prophylaxis of diseases or disorders associated with the activity of MPO and/or EPX.

Examples of diseases or disorders associated with the activity of MPO and/or EPX include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

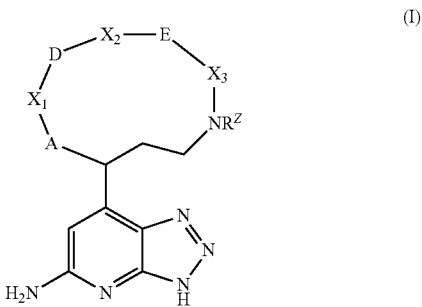

wherein
ring A is pyrazole substituted with 0-1 $R^1$;
$R^1$ is $C_{1-4}$ alkyl, $C_{1-4}$ haloalkyl or halogen;
$X_1$ is $CH_2$, or $C_{1-4}$ alkylene;
D is phenyl, pyridyl or pyrrolidinyl, all of which are substituted with 0-1 $R^2$,
$R^2$ is OH, halogen, $C_{1-4}$ alkyl, $C_{1-4}$ alkoxy or $C_{1-4}$ haloalkyl;
$X_2$ is a bond, $C_{1-4}$ alkylene substituted with 0-2 $R^3$, —O—, —OCH$_2$—, —CH$_2$O—, or —OCHR$^3$—;
$R^3$ is $C_{1-4}$ alkyl;
E is selected from a bond, phenyl, pyridyl, $C_3$-$C_8$ cycloalkyl or pyrrolidinyl, substituted with 0-2 $R^4$
$R^4$ is independently at each occurrence, halogen, $C_{1-4}$ alkoxy, $C_{1-4}$ haloalkoxy, phenyl or benzyl;
$X_3$ is a bond, $C_{1-4}$ alkyl substituted with 0-1 $R^5$ where $R^5$ is alkoxy, halogen, alkyl or hydroxyalkyl; or $X_3$ and NR$^z$ are taken together to form a pyrrolidinyl ring substituted with an aryl or aryl C$_{1-4}$ alkyl or group;

R$^z$ is H, CH$_3$, CH$_2$CH$_2$OCH$_3$, CH$_2$CH$_2$OH, or CH$_2$CONH$_2$;

or a pharmaceutically acceptable salt, stereoisomer, tautomer or a solvate thereof.

In a second aspect of the invention, there is disclosed a compound of formula II

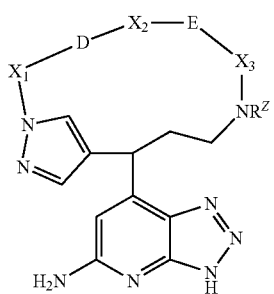

(II)

wherein

X$_1$ is CH$_2$, or C$_{1-4}$ alkylene;

D is phenyl, pyridyl or pyrrolidinyl, all of which are substituted with 0-1 R$^2$, R$^2$ is OH, halogen, C$_{1-4}$ alkyl, C$_{1-4}$ alkoxy or C$_{1-4}$ haloalkyl;

X$_2$ is a bond, C$_{1-4}$ alkylene substituted with 0-1 R$^3$, —O—, —OCH$_2$—, —CH$_2$O—, or —OCHR$^3$—;

R$^3$ is C$_{1-4}$ alkyl;

E is selected from a bond, phenyl, pyridyl, C$_3$-C$_8$ cycloalkyl or pyrrolidinyl, substituted with 0-2 R$^4$ R$^4$ is independently at each occurrence, halogen, C$_{1-4}$ alkoxy, C$_{1-4}$ haloalkoxy, phenyl or benzyl;

X$_3$ is a bond, C$_{1-4}$ alkyl substituted with 0-1 R$^5$ where R$^5$ is alkoxy, halogen, alkyl or hydroxyalkyl;

or X$_3$ and NR$^z$ are taken together to form a pyrrolidinyl ring substituted with an aryl or aryl C$_{1-4}$ alkyl or group;

R$^z$ is H, CH$_3$, CH$_2$CH$_2$OCH$_3$, CH$_2$CH$_2$OH, or CH$_2$CONH$_2$;

In a third aspect of the invention, within the prior aspects of the invention, there is disclosed a compound of formula II, wherein X$_1$ is CH$_2$ or —CH$_2$CH$_2$—;

D is phenyl;

X$_2$ is C$_{1-4}$ alkylene, —O—, —OCH$_2$— or —CH$_2$O;

E is a phenyl or C$_3$-C$_8$ cycloalkyl, substituted with 0-2 R$^4$;

R$^4$ is F, Cl, methoxy, CF$_3$ or benzyl;

X$_3$ is a bond or C$_{1-2}$ alkyl;

or a pharmaceutically acceptable salt, stereoisomer, tautomer or a solvate thereof.

In another aspect, the present invention provides a compound selected from any subset list of compounds within the scope of the prior aspects.

In another aspect, the present invention provides a compound selected the following:

7-{17-oxa-3,4,10-triazatetracyclo[16.3.1.1$^{3,6}$.1$^{12,1^6}$]tetracosa-1(22),4,6(24),12,14,16(23), 18,20-octaen-7-yl}-3H-[1,2,3]triazolo[4,5-b]pyridin-5-amine, 7-{18-oxa-3,4,10-triazatetracyclo[17.3.1.1$^{3,6}$.1$^{13,1^7}$]pentacosa-1(23),4,6(25),13,15,17(24),19,21-octaen-7-yl}-3H-[1,2,3]triazolo[4,5-b]pyridin-5-amine, 7-{18-oxa-3,4,10-triazatetracyclo[17.3.1.1$^{3,6}$.1$^{13,1^7}$]pentacosa-1(23),4,6(25),13,15,17(24),19,21-octaen-7-yl}-3H-[1,2,3]triazolo[4,5-b]pyridin-5-amine, 7-{18-oxa-3,4,10-triazatetracyclo[17.3.1.1$^{3,6}$.1$^{13,1^7}$]pentacosa-1(23),4,6(25),13,15,17(24),19,21-octaen-7-yl}-3H-[1,2,3]triazolo[4,5-b]pyridin-5-amine, 7-{10-methyl-17-oxa-3,4,10-triazatetracyclo[16.3.1.1$^{3,6}$.1$^{12,1^6}$]tetracosa-1(22),4,6(24),12,14,16(23), 18,20-octaen-7-yl}-3H-[1,2,3]triazolo[4,5-b]pyridin-5-amine, 7-{18-oxa-3,4,10-triazatetracyclo[17.3.1.1$^{3,6}$.1$^{12,1^6}$]pentacosa-1(23),4,6(25),12,14,16(24), 19,21-octaen-7-yl}-3H-[1,2,3]triazolo[4,5-b]pyridin-5-amine, 7-[(17R)-18-phenyl-16-oxa-2,8,9-triazapentacyclo[16.2.2.1$^{1,1^7}$.1$^{6,9}$.1$^{11,1^5}$]pentacosa-6(25),7,11(24),12,14-pentaen-5-yl]-3H-[1,2,3]triazolo[4,5-b]pyridin-5-amine, 7-[(17S)-18-phenyl-16-oxa-2,8,9-triazapentacyclo[16.2.2.1$^{1,1^7}$.1$^{6,9}$.1$^{11,1^5}$]pentacosa-6(25),7,11(24),12,14-pentaen-5-yl]-3H-[1,2,3]triazolo[4,5-b]pyridin-5-amine, 7-[(3S,4S)-4-benzyl-2-oxa-6,12,13-triazatetracyclo[13.3.1.1$^{3,6}$.1$^{1^0,13}$]henicosa-1(18),10(20),11,15(19), 16-pentaen-9-yl]-3H-[1,2,3]triazolo[4,5-b]pyridin-5-amine, 7-{14-oxa-3,4,10-triazatricyclo[13.3.1.1$^{3,6}$]icosa-1(19),4,6(20), 15,17-pentaen-7-yl}-3H-[1,2,3]triazolo[4,5-b]pyridin-5-amine, 7-{14'-oxa-3',4',10'-triazaspiro[cyclopropane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 7-{14'-oxa-3',4',10'-triazaspiro[cyclopropane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 7-{14'-oxa-3',4',10'-triazaspiro[cyclopentane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 7-[(3R,4S,6S,10R)-4-benzyl-2-oxa-7,13,14-triazatetracyclo[14.3.1.1$^{3,6}$.1$^{11,14}$]docosa-1(19), 11(21),12,16(20), 17-pentaen-10-yl]-3H-[1,2,3]triazolo[4,5-b]pyridin-5-amine, 7-[(3R,4S,6S,10S)-4-benzyl-2-oxa-7,13,14-triazatetracyclo[14.3.1.1$^{3,6}$.1$^{11,14}$]docosa-1(19),11(21),12,16(20), 17-pentaen-10-yl]-3H-[1,2,3]triazolo[4,5-b]pyridin-5-amine, 7-{8,9,15-triazatetracyclo[16.3.1.1$^{2,6}$.1$^{8,11}$]tetracosa-1(22), 2,4,6(24),9,11(23),18,20-octaen-12-yl}-3H-[1,2,3]triazolo[4,5-b]pyridin-5-amine, 7-{3-oxa-10,11,17-triazatetracyclo[16.2.2.1$^{4,8}$.1$^{1^0,13}$]tetracosa-4,6,8(24),11,13(23)-pentaen-14-yl}-3H-[1,2,3]triazolo[4,5-b]pyridin-5-amine, 7-{15,22-difluoro-18-oxa-3,4,10-triazatetracyclo[17.3.1.1$^{3,6}$.1$^{12,1^6}$]pentacosa-1(23),4,6(25),12,14,16(24), 19,21-octaen-7-yl}-3H-[1,2,3]triazolo[4,5-b]pyridin-5-amine, 7-[(18S)-19-phenyl-17-oxa-2,8,9-triazapentacyclo[17.2.2.1$^{1,1^8}$.1$^{6,9}$.1$^{12,1^6}$]hexacosa-6(26),7,12(25), 13,15-pentaen-5-yl]-3H-[1,2,3]triazolo[4,5-b]pyridin-5-amine, 7-{2-oxa-7,13,14-triazatetracyclo[14.3.1.1$^{3,6}$.1$^{11,14}$]docosa-1(19),11(21),12,16(20),17-pentaen-10-yl}-3H-[1,2,3]triazolo[4,5-b]pyridin-5-amine, 7-[(17R)-17-methyl-18-oxa-3,4,10-triazatetracyclo[17.3.1.1$^{3,6}$. 1$^{12,1^6}$]pentacosa-1(23),4,6(25),12,14,16(24), 19,21-octaen-7-yl]-3H-[1,2,3]triazolo[4,5-b]pyridin-5-amine, 7-{17-oxa-3,4,10-triazatetracyclo[17.3.1.1$^{3,6}$.1$^{12,1^6}$]pentacosa-1(23),4,6(25),12,14,16(24), 19,21-octaen-7-yl}-3H-[1,2,3]triazolo[4,5-b]pyridin-5-amine, 7-[(11S,14R)-16-oxa-3,4,10-triazatetracyclo[15.3.1.1$^{3,6}$.1$^{11,14}$]tricosa-1(21),4,6(23),17,19-pentaen-7-yl]-3H-[1,2,3]triazolo[4,5-b]pyridin-5-amine,

[(11S)-7-{5-amino-3H-[1,2,3]triazolo[4,5-b]pyridin-7-yl}-18-oxa-3,4,10-triazatetracyclo[17.3.1.1$^{3,6}$.1$^{13,1^7}$]pentacosa-1(23),4,6(25),13,15,17(24),19,21-octaen-1-yl]methanol, 7-{14-fluoro-17-oxa-3,4,10-triazatetracyclo[17.3.1.1$^{3,6}$.1$^{12,1^6}$]pentacosa-1(23),4,6(25), 12(24), 13,15,19,21-octaen-7-yl}-3H-[1,2,3]triazolo[4,5-b]pyridin-5-amine, 7-{15-fluoro-17-oxa-3,4,10-triazatetracyclo[17.3.1.1$^{3,6}$.1$^{12,1^6}$]pentacosa-1(23),4,6(25), 12(24),13,15,19,21-octaen-7-yl}-3H-[1,2,3]triazolo[4,5-b]pyridin-5-amine, 7-{14-chloro-17-oxa-3,4,10-triazatetracyclo[17.3.1.1$^{3,6}$.1$^{12,1^6}$]pentacosa-1(23),4,6(25), 12(24), 13,15,19,21-octaen-7-yl}-3H-[1,2,3]triazolo[4,5-b]pyridin-5-amine, 7-{18-oxa-3,4,10-triazatetracyclo[18.3.1.1$^{3,6}$.1$^{13,1^7}$]hexacosa-1(24),4,6(26), 13(25),14,16,20,22-octaen-7-yl}-3H-[1,2,3]triazolo[4,5-b]pyridin-5-amine, 7-[(11R)-11-methyl-18-oxa-3,4,10-triazatetracyclo[17.3.1.1$^{3,6}$.1$^{13,1^7}$]pentacosa-1(23),4,6(25),13,15,17(24),19,21-octaen-7-yl]-3H-[1,2,3]triazolo[4,5-b]pyridin-5-amine, 7-[(11S)-11-methyl-18-oxa-3,4,10-triazatetracyclo[17.3.1.1$^{3,6}$.1$^{13,1^7}$]pentacosa-1(23),4,6(25),13,15,17(24),19,21-octaen-7-yl]-3H-[1,2,3]triazolo[4,5-b]pyridin-5-amine, 7-[(17R)-17-(2-methylpropyl)-18-oxa-3,4,10-triazatetracyclo[17.3.1.1$^{3,6}$.1$^{12,1^6}$]pentacosa-1 (23),4,6(25),12,14,16(24),19,21-octaen-7-yl]-3H-[1,2,3]triazolo[4,5-b]pyridin-5-amine, 7-[(3R,4S,6S)-4-benzyl-2-oxa-7,13,14-triazatetracyclo[15.3.1.1$^{3,6}$.1$^{11,1^4}$]tricosa-1(20),11(22),12,17(21),18-pentaen-10-yl]-3H-[1,2,3]triazolo[4,5-b]pyridin-5-amine, 7-[(3R,4S,6S)-4-benzyl-2-oxa-7,13,14-triazatetracyclo[15.3.1.1$^{3,6}$.1$^{11,1^4}$]tricosa-1(20),11(22),12,17(21),18-pentaen-10-yl]-3H-[1,2,3]triazolo[4,5-b]pyridin-5-amine, 7-{5-amino-3H-[1,2,3]triazolo[4,5-b]pyridin-7-yl}-13-(2-phenylethyl)-3,4,10,13-tetraazatricyclo[13.3.1.1$^{3,6}$]icosa-1(19),4,6(20),15,17-pentaen-12-one, 7-{12,12-difluoro-18-oxa-3,4,10-triazatetracyclo[17.3.1.1$^{3,6}$.1$^{13,1^7}$]pentacosa-1(23),4,6(25),13,15,17(24),19,21-octaen-7-yl}-3H-[1,2,3]triazolo[4,5-b]pyridin-5-amine, or a stereoisomer, a tautomer, or a pharmaceutically acceptable salt thereof.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof. In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need of such treatment and/or prophylaxis a therapeutically effective amount of at least one of the compounds of the present invention, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of diseases or disorders associated with the activity of MPO and/or EPX.

Examples of diseases or disorders associated with the activity of MPO and/or EPX that may be prevented, modulated, or treated according to the present invention include, but are not limited to, atherosclerosis, coronary heart disease, coronary artery disease, coronary vascular disease, cerebrovascular disorders, peripheral vascular disease, dyslipidemias and the sequelae thereof, cardiovascular disorders, angina, ischemia, cardiac ischemia, heart failure, stroke, myocardial infarction, reperfusion injury, angioplastic restenosis, hypertension, vascular complications of diabetes, obesity or endotoxemia.

In one embodiment, examples of diseases or disorders include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, transient ischemic attack and stroke. In one embodiment, examples of diseases or disorders include atherosclerosis, coronary heart disease, cerebrovascular disorders and dyslipidemias and the sequelae thereof. In one embodiment, examples of diseases or disorders include coronary artery disease and acute coronary syndrome. In one embodiment, examples of diseases or disorders include dyslipidemias and the sequelae thereof. In one embodiment, examples of diseases or disorders include heart failure. In one embodiment, examples of diseases or disorders include lung diseases including asthma, COPD and cystic fibrosis. In one embodiment, examples of diseases or disorders include neuroinflammatory diseases, including multiple sclerosis, Alzheimer's disease, Parkinson's disease, multiple system atrophy, and stroke.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, diuretics, mineralocorticoid receptor antagonists, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma high-density lipoprotein (HDL)-raising agents, anti-hypercholesterolemic agents, cholesterol biosynthesis inhibitors (such as HMG CoA reductase inhibitors), acyl-coenzyme A:cholesterol acytransferase (ACAT) inhibitors, cholesterylester transfer protein (CETP) inhibitors, liver X receptor (LXR) agonists, anti-probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, diuretics, mineralocorticoid receptor antagonists, calcium channel blockers, anti-diabetes agents, angiotensin II receptor antagonists, angiotensin converting enzyme inhibitors, platelet aggregation inhibitors, factor Xa inhibitors, anti-thrombotic agents, renin inhibitors, fibrinogen receptor antagonists, aspirin and fabric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 15th Edition, John Wiley & Sons, Inc., New York (2007). "$C_6$ or $C_{10}$ aryl" or "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated, or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene, T. W. et al., *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH). Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of Formula (I) or Formula (II)) is a prodrug within the scope and spirit of the invention. Various forms of prodrugs are well known in the art. For examples of such prodrug derivatives, see:

(a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) or Formula (II) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "μwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Ac | Acetic |
| AcOH | acetic acid |
| ACN (or MeCN) | acetonitrile |
| APF | aminophenyl fluorescein |
| BINAP | 2,2'-bis(diphenylphosphino)-1,1'-binaphthyl |
| Bn | benzyl |
| Boc | tert-butyl carbonyl |
| Boc$_2$O | Di-tert-butyl dicarbonate |
| Bu | butyl |
| dba (Pd$_2$(dba)$_3$) | dibenzylideneacetone |
| CMBP | cyanomethylenetributylphosphorane |
| DCM | dichloromethane |
| DEAD | diethyl azodicarboxylate |
| DIAD | diisopropyl azodicarboxylate |
| Diamide | N,N,N',N'-Tetramethylazodicarbonamide (1,1'-Azobis(N,N-dimethylformamide)) |
| DIEA | diisopropylethylamine |
| DMAP | 4-dimethylaminopyridine |
| DME | Dimethoxyethane |
| DMF | dimethylformamide |
| DMSO | dimethyl sulfoxide |
| dppf | 1,1'-bis(diphenylphosphino)ferrocene |
| (DtBPF)PdCl$_2$ | 1.1'-bis(di-tert-butylphosphino)ferrocene palladium dichloride |
| EPX | eosinophil peroxidase |
| Et | ethyl |
| EtOH | ethanol |
| EtOAc | ethyl acetate |
| HATU | 2-(7-Aza-1H-benzotriazole-1-yl)-1,1,3,3-tetramethyluronium hexafluorophosphate |

| | |
|---|---|
| HBTU | 2-(1H-Benzotriazole-1-yl)-1,1,3,3-tetramethyluronium hexafluorophosphate |
| i-Bu | isobutyl |
| i-Pr | isopropyl |
| LAH | lithium aluminum hydride |
| Me | methyl |
| MeOH | methanol |
| MPO | myeloperoxidase |
| NMM | N-methylmorpholine |
| NMP | N-Methylpyrrolidone |
| PCC | pyridinium chlorochromate |
| Ph | phenyl |
| Pr | propyl |
| t-Bu | tert-butyl |
| TBDMS-Cl | t-butyldimethylchlorosilane |
| TBDMS | t-butyldimethylsilyl |
| TBDPS | t-butyldiphenylsilyl |
| TBDPS-Cl | t-butyldiphenylchlorosilane |
| TEA | Triethylamine |
| TFA | Trifluoroacetic acid |
| THF | tetrahydrofuran |
| TMAD | N,N,N',N'-Tetramethylazodicarbonamide (1,1'-Azobis(N,N-dimethylformamide)) |
| Ts | tosyl |

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH Publishers, Inc., New York, N.Y. (1999). Preferred methods include, but are not limited to, those described below. *All references* cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., *Protecting Groups in Organic Synthesis*, 4th Edition, Wiley (2007)).

Compounds having the general Formula (I):

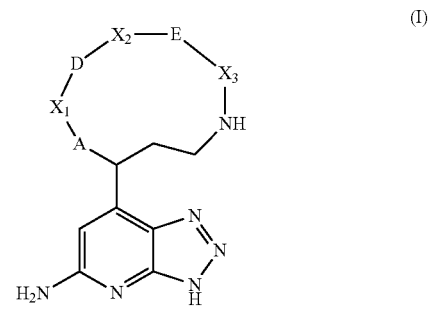

wherein A, $X_1$, D, $X_2$, E and $X_3$ are defined above, can be prepared by the following one or more of the synthetic schemes outlined below.

Macrocyclic compounds of this invention can be prepared by cyclization of a suitably functionalized acyclic precursor under appropriately dilute reaction conditions to minimize intermolecular reaction. Examples of such cyclizations are intramolecular Ullmann reaction between a phenol or aliphatic alcohol and an aryl iodide or bromide (for examples, see Uchiro, H. et al. *Org. Lett.* 2011,13, 6268 or Collins, J. C. et al. *J. Org. Chem.* 2012, 77, 11079.), intramolecular Mitsunobu condensation of a phenol with a benzylic or primary or secondary alcohol (for examples, see Chen, K. X. et al. *J. Med. Chem.* 2005, 49, 567) or intramolecular Suzuki-Miyaura reaction of a boronic acid or boronate with a suitable coupling partner such as an aryl or vinyl iodide or bromide (for example, see Dieckmann, M.; et al., Angew. Chem. Int. Ed. 2012, 51, 5667-5670). Other macrocyclization methods include macrolactamizations, macrolactonization and intramolecular olefin metathesis (for examples, see Yu, X. and Sun, D. *Molecules* 2013, 18, 6230).

Compounds of this invention wherein D and E are phenyl and $X_2$ is O can be prepared by intramolecular Ullmann condensation from a suitably protected precursor 1-1 as shown in Scheme 1. Typical reagents and conditions for this cyclization are CuI, a base such as cesium carbonate, and a ligand such as 9,10-phenanthroline in a suitable solvent such as toluene at a temperature of 110-150° C. at a concentration of 3-5 mM in a sealed flask. Deprotection of the N-protecting groups with TFA or TFA/triethylsilane in DCM provides the desired macrocycles 1-2.

Scheme 1

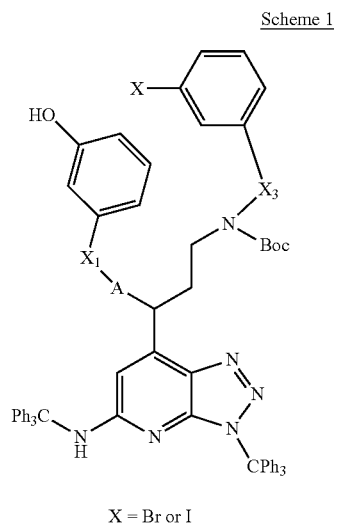

X = Br or I

Scheme 2

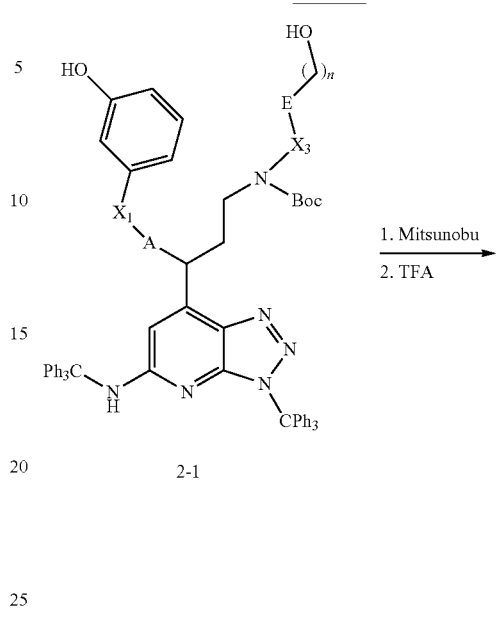

2-1

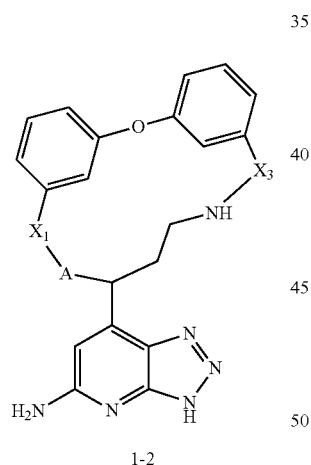

1-2

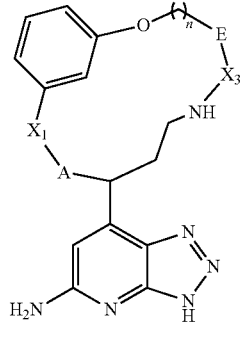

2-2

Alternately, compounds of this invention wherein D is phenyl and $X_2$ is $O(CH_2)_n$, can be prepared by intramolecular Mitsunobu reaction of suitably protected precursors 2-1 as shown in Scheme 2. For primary alcohol intermediates, the cyclization can be carried out using DIAD and triphenylphosphine in THF at a concentration of 1-3 mM and a temperature from 0° C. to room temperature. For secondary alcohols (e.g. when E is a saturated carbocycle and n=0), a mixture of DIAD, triphenylphosphine and triethylamine can be used, or for more sterically hindered secondary alcohols, a solution of CMBP in toluene at 100° C. provides the macrocyclic products. Deprotection of the N-protecting groups with TFA or TFA/triethylsilane in DCM provides the desired macrocycles 2-2.

Alternately, as shown in Scheme 3, macrocycles of this invention can be prepared from suitably protected and functionalized intermediates 3-1 via an intramolecular Suzuki-Miyaura condensation, followed by deprotection and reduction of the double bond. An effective catalyst for this cyclization is Pd(dppf)Cl$_2$ in the presence of a base such as $K_2CO_3$ or Ba(OH)$_2$ in a solvent such as aq. Dioxane or DMF at temperatures from room temperature to 85° C. and concentrations from 1-10 mM. Deprotection of the N-protecting groups with TFA or TFA/triethylsilane in DCM, followed by hydrogenation over PtO$_2$ to reduce the double bond, provides the desired macrocycles 3-2.

Scheme 3
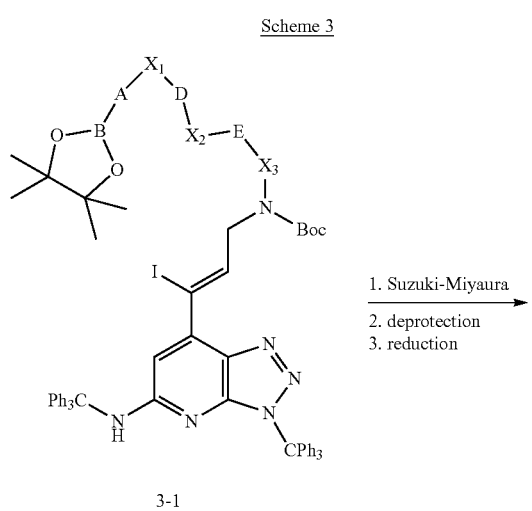
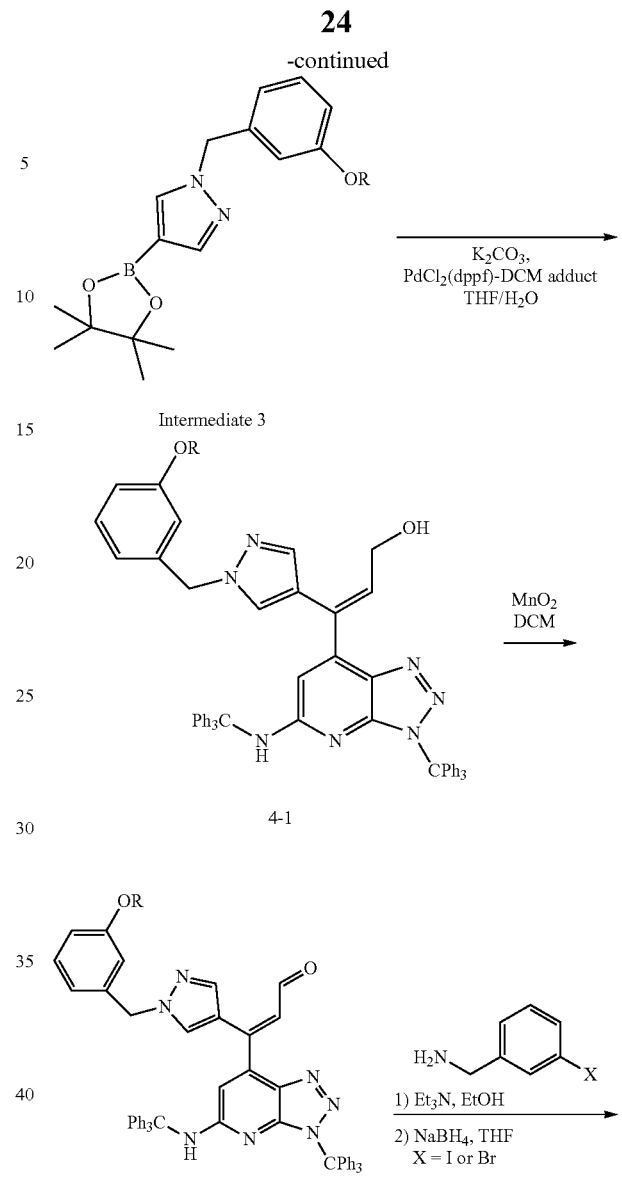
Compounds of this invention can further be prepared as outlined in Schemes 4-8 below and as described in detail in the specific examples that follow. It should be noted that all bis-tritylated triazolopyridine intermediates were obtained as mixtures of two trityl regioisomers which were carried through without separation.
Scheme 4
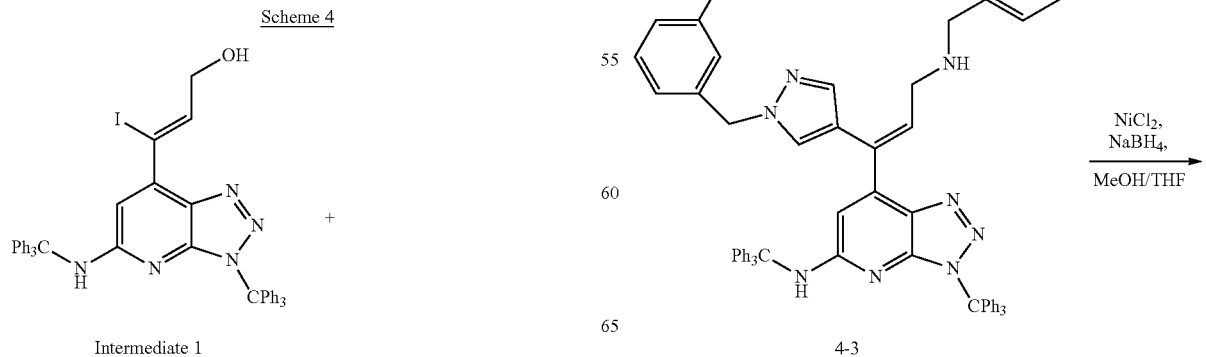

25
-continued
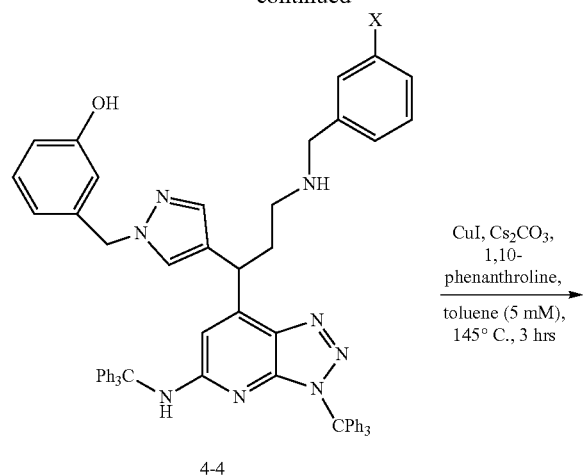
4-4
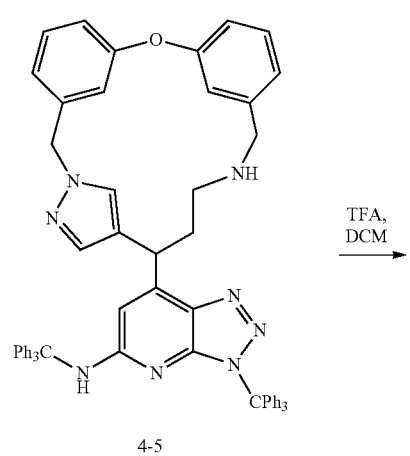
4-5
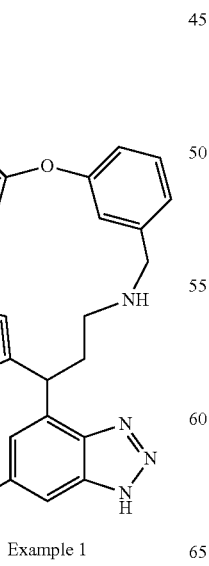
Example 1
26
Scheme 5
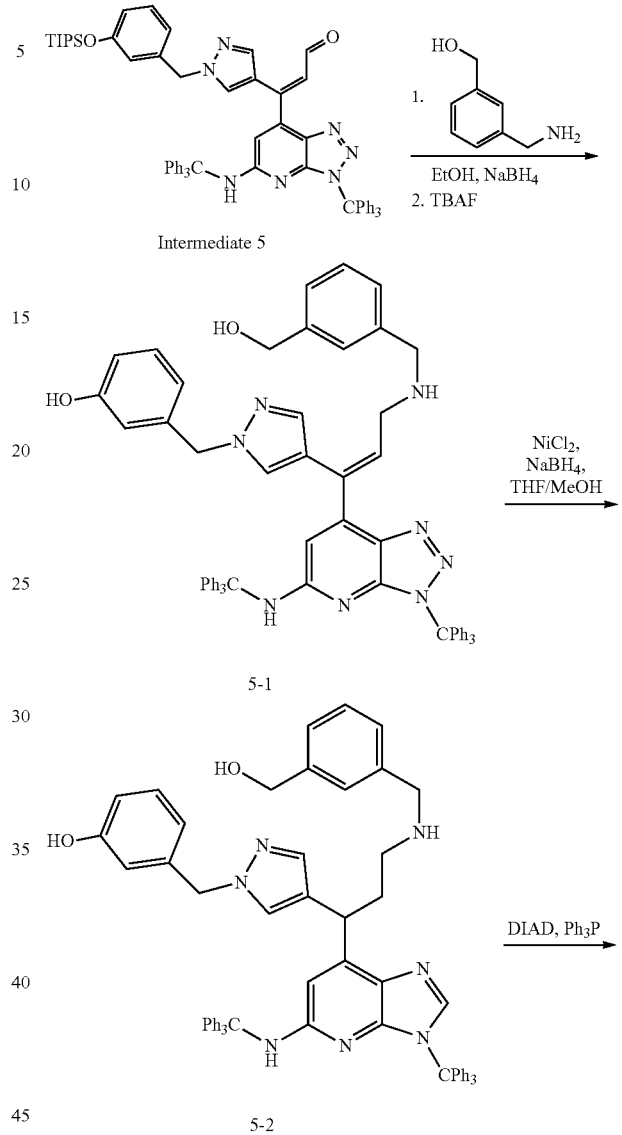

-continued
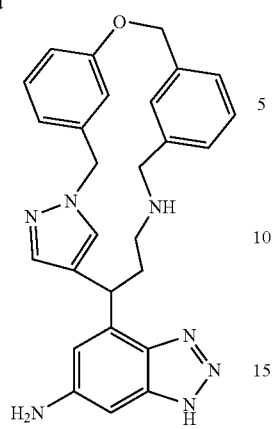
Example 2
Scheme 6
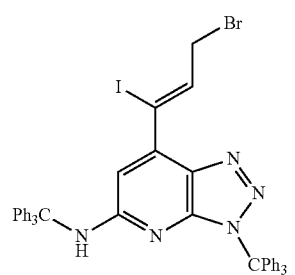
Intermediate 3
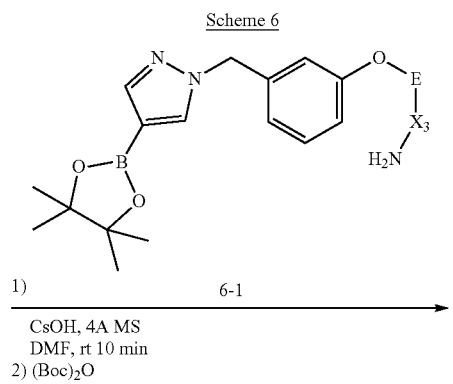
6-1
1) CsOH, 4A MS
DMF, rt 10 min
2) (Boc)₂O
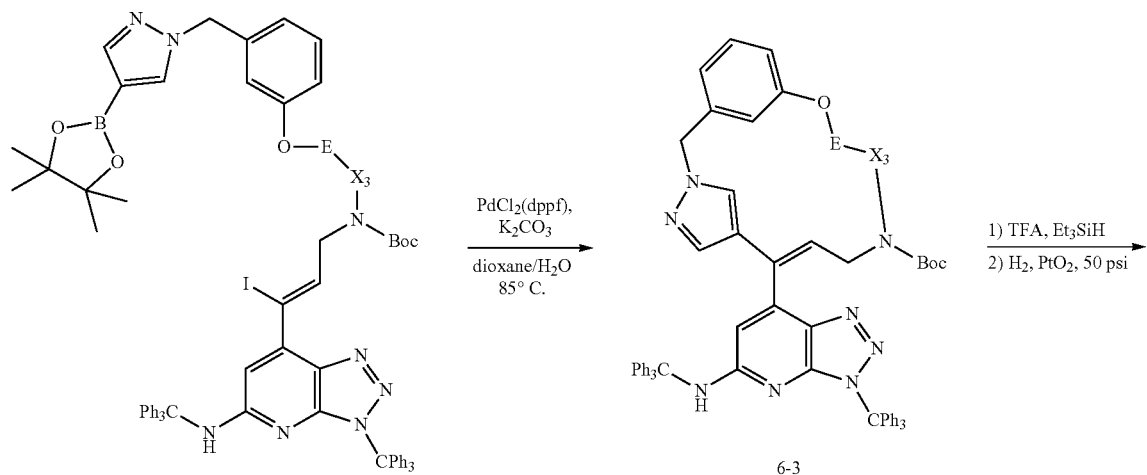
6-2
PdCl₂(dppf), K₂CO₃
dioxane/H₂O
85° C.
6-3
1) TFA, Et₃SiH
2) H₂, PtO₂, 50 psi -continued
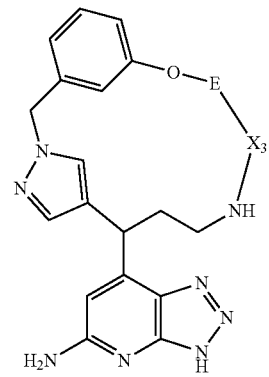
6-4
Scheme 7
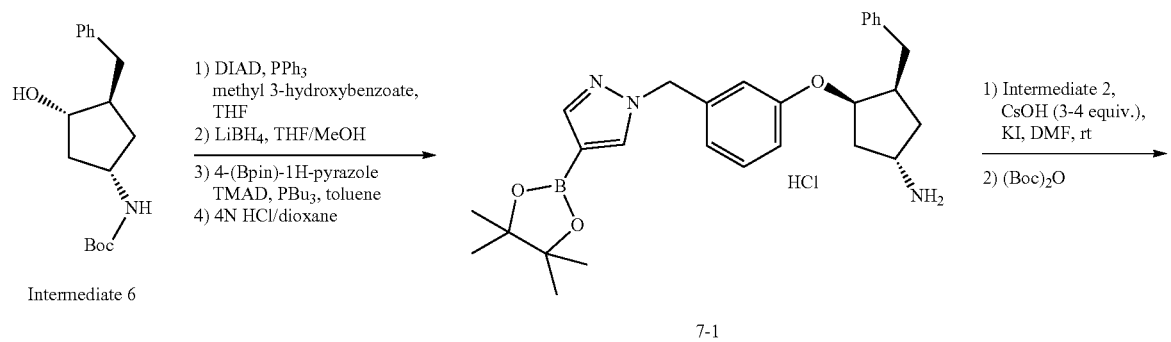
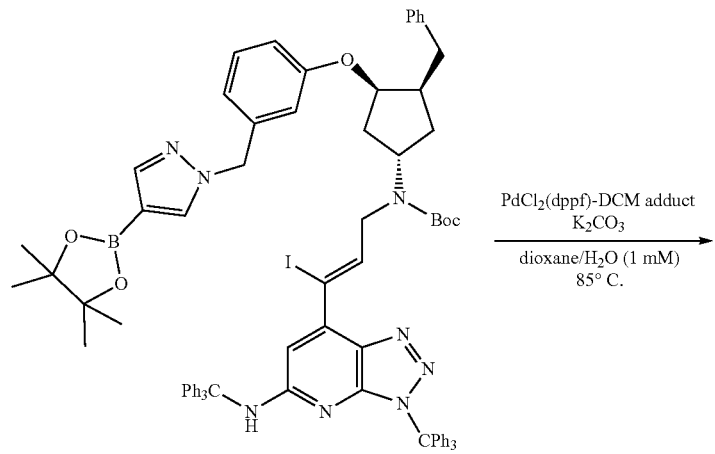
7-2

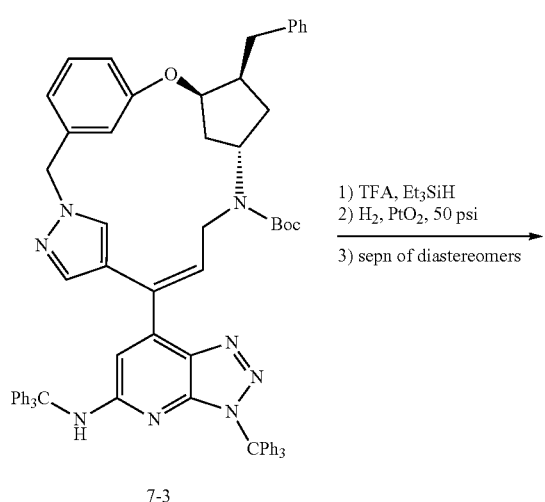

7-3

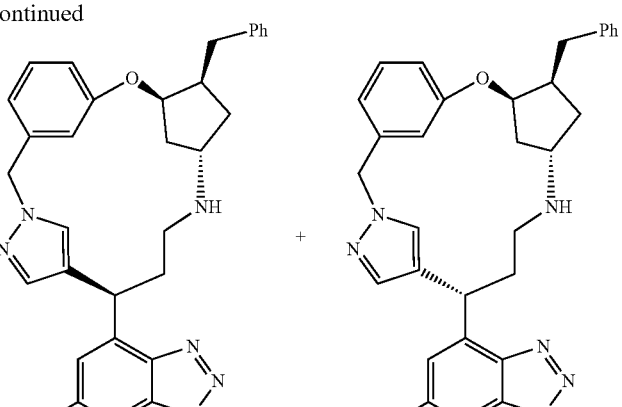

Example 25     Example 26

Scheme 8

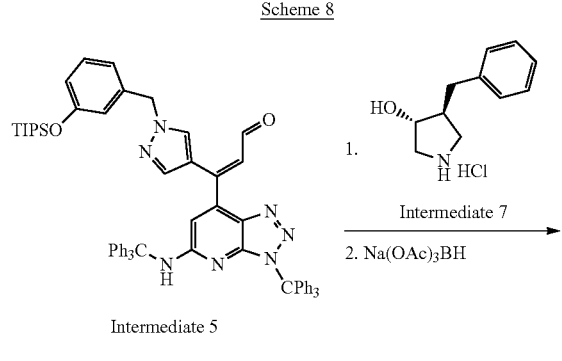

Intermediate 5

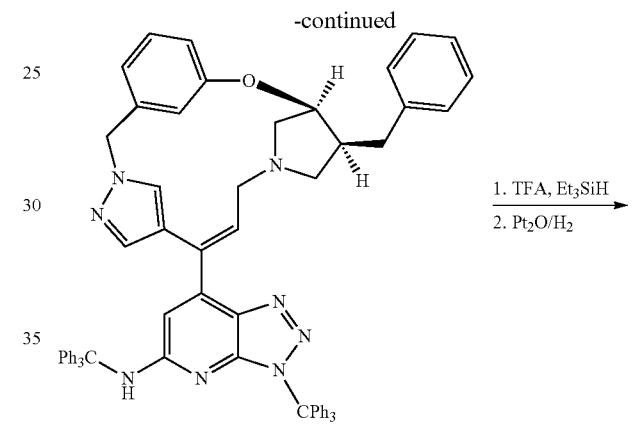

8-2

Example 31

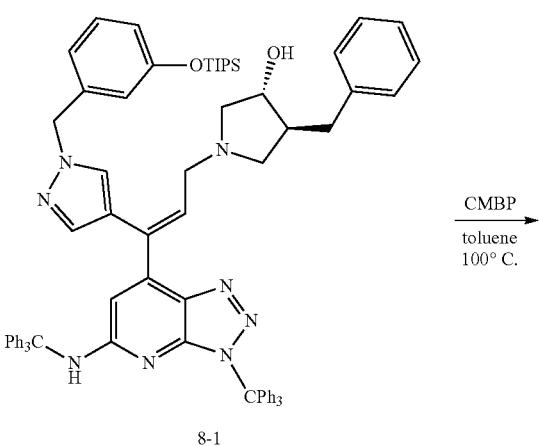

8-1

General Methods

The following methods were used in the exemplified Examples, except where noted otherwise.

Purification of intermediates and final products was carried out via either normal or reverse phase chromatography. Normal phase chromatography was carried out using pre-packed SiO$_2$ cartridges eluting with either gradients of hexanes and ethyl acetate or DCM and MeOH unless otherwise indicated. For highly polar amines, gradients of DCM and 1M NH$_3$ in MeOH were used. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (90% water, 10% ACN, 0.1% TFA) and Solvent B (10% water, 90% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 5% water, 10 mM $NH_4OAc$) or with gradients of Solvent A (95% water, 2% ACN, 0.1% $NH_4OH$) and Solvent B (98% ACN, 2% water, 0.1% $NH_4OH$).

Analytical HPLC: Methods Employed in Characterization of Examples

Products were analyzed by reverse phase analytical HPLC: carried out on a Shimadzu Analytical HPLC: system running Discovery VP software. RT=retention time.

Method A: Linear gradient of 0 to 100% B over 10 min, with
  5 min hold at 100% B
  UV visualization at 254 nm
  Column: SunFire C18; 3.5 μm; 4.6×150 mm
  Flow rate: 1 mL/min (Method A)
  Solvent A: 10% acetonitrile, 90% water, 0.05% TFA
  Solvent B: 10% water, 90% acetonitrile, 0.05% TFA Method B: Linear gradient of 0 to 100% B over 10 min, with
  5 min hold at 100% B
  UV visualization at 254 nm
  Column: XBridge Phenyl 3.5 μm; 4.6×150 mm
  Flow rate: 1 mL/min (Method A)
  Solvent A: 10% acetonitrile, 90% water, 0.05% TFA
  Solvent B: 10% water, 90% acetonitrile, 0.05% TFA Method C: Linear gradient: 0-100% B over 3 min, then a 0.75-min hold at 100% B
  Temperature: 50° C.
  UV visualization at 220 nm
  Column: Waters Acquity UPLC BEH C18, 1.7 μm; 2.1×50 mm
  Flow: 1.11 mL/min (Method A)
  Solvent A: 5:95 acetonitrile:water with 0.1% TFA
  Solvent B: 95:5 acetonitrile:water with 0.1% TFA Method D: Linear gradient: 0-100% B over 3 min, then a 0.75-min hold at 100% B
  Temperature: 50° C.
  UV visualization at 220 nm
  Column: Waters Acquity UPLC BEH C18, 1.7 μm; 2.1×50 mm
  Flow: 1.11 mL/min (Method A)
  Solvent A: 5:95 acetonitrile:water with 10 mM ammonium acetate
  Solvent B: 95:5 acetonitrile:water with 10 mM ammonium acetate LC/MS Methods Employed in Characterization of Examples Reverse phase analytical HPLC/MS was performed on Shimadzu LC10AS systems coupled with Waters ZMD Mass Spectrometers (Methods A-E) or Waters Acquity system coupled with a Waters MICROMASS® ZQ Mass Spectrometer (Method F).

Method A: Linear gradient of 0 to 100% B over 4 min, with
  1 min hold at 100% B
  UV visualization at 220 nm
  Column: PHENOMENEX® Luna C18 4.6×50 mm
  Flow rate: 4 mL/min (Method A)
  Solvent A: 0.1% trifluoroacetic acid, 90% water, 10% acetonitrile
  Solvent B: 0.1% trifluoroacetic acid, 90% acetonitrile, 10% water Method B: Linear gradient of 0 to 100% B over 4 min, with
  1 min hold at 100% B
  UV visualization at 220 nm
  Column: PHENOMENEX® Luna C18 2×50 mm
  Flow rate: 4 mL/min (Method A)
  Solvent A: 98% water, 2% methanol, 0.1% formic acid
  Solvent B: Methanol, 0.1% formic acid Method C: Linear gradient of 0 to 100% B over 4 min, with
  1 min hold at 100% B
  UV visualization at 220 nm
  Column: PHENOMENEX® Luna C18 4.6×50 mm
  Flow rate: 4 mL/min (Method A)
  Solvent A: 0.1% trifluoroacetic acid, 90% water, 10% methanol
  Solvent B: 0.1% trifluoroacetic acid, 90% methanol, 10% water Method D: Linear gradient of 0 to 100% B over 2 min, with
  1 min hold at 100% B
  UV visualization at 220 nm
  Column: PHENOMENEX® Luna C18 2.0×30 mm
  Flow rate: 1 mL/min (Method A)
  Solvent A: 0.1% trifluoroacetic acid, 90% water, 10% methanol
  Solvent B: 0.1% trifluoroacetic acid, 90% methanol, 10% water Method E: Linear gradient of 0 to 100% B over 2 min, with
  1 min hold at 100% B
  UV visualization at 220 nm
  Column: PHENOMENEX® Luna C18 2.0×30 mm
  Flow rate: 1 mL/min (Method A)
  Solvent A: 98% water, 2% methanol, 0.1% formic acid
  Solvent B: Methanol, 0.1% formic acid.

Method F: Linear gradient of 2 to 98% B over 1 min, with
  0.5 min hold time at 98% B
  UV visualization at 220 nm
  Column: Waters BEH C18 2.1×50 mm
  Flow rate: 0.8 mL/min (Method A)
  Solvent A: 0.05% TFA, 100% water
  Solvent B: 0.05% TFA, 100% acetonitrile Preparative HPLC: Methods Employed in the Purification of Products Method G: Linear gradient of 20 to 100% B over 10 min, with 2 min hold time at 100% B
  Shimadzu LC-8A binary pumps
  Shimadzu SPD-10 A or 20 A UV detector
  UV visualization at 220 nm
  Column: Waters SunFire 19×100 mm 5 μm C18
  Flow rate: 20 mL/min (Method A).
  Solvent A: 0.1% TFA, 10% MeOH, 90% water
  Solvent B: 0.1% TFA, 90% MeOH, 10% water Method J: Linear gradient of 20 to 100% B over 10 min, with 2 min hold time at 100% B
  Shimadzu LC-8A binary pumps
  Shimadzu SPD-10A or 20A UV detector
  UV visualization at 220 nm
  Column: PHENOMENEX® Luna Axia 30×100 mm 5 μm C18
  Flow rate: 20 mL/min (Method A).
  Peak collection triggered by UV absorbance
  Solvent A: 0.1% TFA, 10% MeOH, 90% water
  Solvent B: 0.1% TFA, 90% MeOH, 10% water Method K: Linear gradient of 0 to 100% B over 10 min, with 2 min hold time at 100% B
  Shimadzu LC-8A binary pumps
  Shimadzu SPD-20A UV detector
  UV visualization at 220 nm Column: PHENOMENEX® Luna Axia 30×75 mm 5 µm C18

Flow rate: 20 mL/min (Method A).

Peak collection triggered by UV absorbance

Solvent A: 0.1% TFA, 10% ACN, 90% water

Solvent B: 0.1% TFA, 90% ACN, 10% water

NMR Employed in Characterization of Examples $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (3 units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled. For $^1$H NMR spectrum taken in 1:1 mixtures of $CDCl_3$ and MeOH, the spectra were referenced to the $CD_3OD$ solvent peak.

IV. Biology

Myeloperoxidase (MPO) and eosinophil peroxidase (EPX) are heme-containing enzymes and are members of the family of mammalian heme peroxidases that also includes salivary peroxidase, lactoperoxidase (LPO), thyroid peroxidase (TPO), prostaglandin H synthase and others. Both MPO and EPX use hydrogen peroxide to oxidize an array of substrates to either hypohalous acids or free radicals. Whereas both EPX and MPO are able to oxidize bromine ($Br^-$), iodine ($I^-$) and thiocyanate ($^-SCN$), MPO is also able to oxidize chloride ($Cl^-$) to hypochlorous acid (HOCl) efficiently.

MPO is present predominantly in neutrophils and to a lesser extent in monocytes and subtypes of tissue macrophages. The processed mature form of the enzyme is a glycosylated 146 kDa homodimer. Each subunit is made of a light and heavy polypeptide chain and contains a protoporphyrin IX group with a central iron. The three-fold linkage of the heme is unique compared to other heme proteins and provides specific spectral and catalytic properties to MPO. MPO uses hydrogen peroxide to oxidize an array of substrates to either hypohalous acids or free radicals. The main substrate for MPO is generally accepted to be chloride, which is oxidized to hypochlorous acid. This is one of the most reactive oxidants produced in vivo. Other substrates include thiocyanate, bromide, tyrosine, tryptophan, sulfhydryls, phenol and indole derivatives, ascorbate, nitrite, nitric oxide, and urate.

The physiological role of MPO is to participate in the killing of invading bacterial and fungal pathogens (Klebanoff, S. J., *J. Exp Med.,* 126:1063-1078 (1967); Klebanoff, S. J., *J. Bacteriol.,* 95:2131-2138 (1968); Klebanoff, S. J., *Science,* 169:1095-1097 (1970)). However, excessive generation of oxidants by MPO and other peroxidases has been linked to tissue damage in many diseases, especially those characterized by acute or chronic inflammation. At sites of inflammation, PMNs or tissue macrophages can generate hydrogen peroxide and upon activation also produce myeloperoxidase. This is evidenced by the fact that, in many cases, enzymatically active MPO in conjunction with 3-chlorotyrosine, a tissue marker for HOCl-mediated damage, or HOCl-modified proteins can be detected in diseased tissues colocalized with neutrophils or macrophages (Daugherty, A. et al., *JCI,* 94:437-444 (1994); Bergt et al., *Proc. Natl. Acad. Sci.,* 101:13032-13037 (2004); Pennathur, S. et al., *JBC,* 279:42977-42983 (2004); Choi D. K. et al., *J. Neurosci.,* 25(28):6394-6600 (2005)).

Eosinophil peroxidase (EPX) is a cationic heme-containing protein, and represents nearly 25% of the total mass of the secondary granule protein in eosinophils. It is a highly basic 77 kDa protein made up of two subunits containing a modified Fe-protoporphyrin-IX prosthetic group. EPX shares with MPO the ability to use $H_2O_2$ to oxidize thiocyanate, bromide, and nitrite in vivo to kill bacteria, and viruses (Jong, E. C. et al., *J. Immunol.,* 124:1949-1953 (1980)). Eosinophils play a unique role in host defense mechanisms but increased levels of circulating and tissue eosinophils are implicated in promoting cellular and tissue injury in particular in asthma, and during allergic inflammatory responses of lung diseases.

MPO Peroxidation Assay (Amplex Red Assay)

MPO peroxidation activity was measured in 100 mM KPi (pH 7.4) by utilizing the non-fluorescent reagent Amplex Red (Invitrogen Cat. #A12222) which can be oxidized to the highly fluorescent resorufin. Amplex Red is oxidized by the peroxidase action of MPO to resorufin. Reactions were carried out in 50 µL total volume by adding a 25 µL mixture of 200 pM myeloperoxidase and 40 nM $H_2O_2$ (Sigma #349887) to 100 nL inhibitor in 100% DMSO in a 384 well Perkin Elmer Optiplate. Enzyme and compound were preincubated for ten minutes at room temperature.

After the ten minute preincubation, 25 µL of an Amplex Red mixture containing 200 µM Amplex Red and 10 mM $H_2O_2$ was added to the plate. Kinetic determinations were carried out immediately on a Perkin Elmer Envision (15 minute kinetic read, Ex: 535 nm, Em: 590 nm).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

MPO Chlorination Assay (APF Assay) MPO chlorination activity was measured in 100 mM KPi (pH 7.4) by utilizing the non-fluorescent reagent Aminophenyl fluorescein (APF, Invitrogen Cat. #A36003). APF is cleaved by (—OCl) to yield the fluorescent compound fluorescein. Reactions were carried out in 50 µL total volume by adding a 25 µL mixture of 200 pM myeloperoxidase and 120 mM NaCl to 100 nL inhibitor in 100% DMSO in a 384 well, non-binding surface clear bottom plate (Corning #3655). Enzyme, inhibitor, and chloride were preincubated for ten minutes at room temperature.

After the ten minute preincubation, 25 µL of an APF mixture containing 10 mM APF, 120 mM NaCl and 10 µM $H_2O_2$ was added to the plate using the internal dispensing system of a Hammatsu FDSS 6000. Kinetic determinations were carried out immediately on the FDSS 6000 (3 minute kinetic read, 1 read every second, ex: 485 nm, em: 535 nm).

IC$_{50}$ values for inhibitors were calculated by taking the slope of the linear portion of the kinetic measurement (20 seconds to 80-120 secs).

IC$_{50}$ values were calculated by determining the slope of the linear portion of the kinetic trace (180-540 secs), and using that calculated slope to determine % inhibition occurring at each concentration of inhibitor using the following equation:

$$Y = A + \frac{B-A}{1+(C/x)^D}$$

where A=minimal Y value (activity level of inhibited sample), B=maximal Y value (activity level of uninhibited sample), C=Log IC$_{50}$, D=Hill Slope, x=concentration of inhibitor.

EPX Bromination Assay

EPX bromination activity was measured in 100 mM KPi (pH 7.4) by monitoring the H$_2$O$_2$ catalyzed formation of 3-bromo tyrosine from tyrosine and potassium bromide. A 50 µl mixture of 0.6 µM EPX (Lee Biosolutions Cat. #342-60) was added to 100 nL inhibitor in 100% DMSO in a 384 well REMP plate. Enzyme and compound were preincubated for ten minutes at room temperature.

After the ten minute preincubation of enzyme and inhibitor, 25 µL of a mixture containing 400 µM tyrosine and 1200 µM potassium bromide was added to the plate containing enzyme and inhibitor, followed by the addition of 25 µl of 20 µM H$_2$O$_2$. The reaction was allowed to proceed for 15 minutes, at which time it was quenched with 10 µL of 20% TCA. The final concentrations of all components were 0.3 µM EPX, 100 µM tyrosine, 400 µM potassium bromide, 5 µM H$_2$O$_2$, 0.1% DMSO, 2.0% TCA.

IC$_{50}$ values were determined by determining the peak areas of 3-bromo-tyrosine present at the end of the 15 minute reaction and fitting the data to:

$$Y = A + \frac{B-A}{1+(C/x)^D}$$

where A=minimal Y value (activity level of inhibited sample), B=maximal Y value (activity level of uninhibited sample), C=Log IC$_{50}$, D=Hill Slope, x=concentration of inhibitor.

Reversed-phase analysis was performed on a Waters Acquity Ultra Performance LC system using an Acquity UPLC BEH C$_{18}$ 1.7 µM, 2.1×50 mm analytical column. The column was maintained at 60° C. Samples were eluted using a gradient of 0%-100% B over 2.5 minutes, followed by equilibration with 100% A for 1 minute where A consisted of 0.1% TFA and B consisted of 90% MeOH/0.1% TFA at a flow rate of 0.6 mL/min. The retention time of 3-bromo tyrosine was 1.22 min (Method A).

The exemplified Examples disclosed below were tested in the MPO peroxidation assay described above and found to have MPO inhibitory activity. A range of IC$_{50}$ values of ≤10 µM (10000 nM) was observed.

Most of the exemplified Examples disclosed below were tested in the MPO chlorination assay described above and found having MPO inhibitory activity. A range of IC$_{50}$ values of ≤10 µM (10000 nM) was observed.

Some compounds of the invention were tested in the EPX bromination assay described above and were found to inhibit EPX with a range of IC$_{50}$ values of ≤10 µM (10000 nM), as demonstrated by Example 2 (EPX IC$_{50}$=0.19 µM); Example 5 (EPX IC$_{50}$=0.037 µM); Example 18 (EPX IC$_{50}$=0.22 µM); and Example 20 (EPX IC$_{50}$=0.063 µM).

Table 1 below lists IC$_{50}$ value range in the MPO peroxidation (Amplex Red) assay and MPO chlorination assay (APF) measured for the following Examples. Potency ranges A=1-100 nM; B=101-999 nM; C=1000-10000 nM.

TABLE 1

| Example No. | Amplex Red Assay IC$_{50}$ value (µM) | APF Assay IC$_{50}$ value (µM) |
|---|---|---|
| 1 | B | A |
| 2 | B | A |
| 3 | A | A |
| 4 | B | B |
| 5 | A | A |
| 6 | C | B |
| 7 | A | A |
| 8 | B | A |
| 9 | A | A |
| 10 | B | A |
| 11 | B | A |
| 12 | A | A |
| 13 | C | B |
| 14 | C | A |
| 15 | B | A |
| 16 | B | A |
| 17 | C | B |
| 18 | B | A |
| 19 | B | A |
| 20 | B | B |
| 21 | B | A |
| 22 | B | A |
| 23 | C | B |
| 24 | B | A |
| 25 | A | A |
| 26 | A | A |
| 27 | A | A |
| 28 | C | A |
| 29 | A | A |
| 30 | B | A |
| 31 | B | A |
| 32 | B | A |
| 33 | B | A |
| 34 | C | B |
| 35 | C | C |
| 36 | C | A |
| 37 | C | B |

Accordingly, the compounds of the present invention may be administered to mammals, preferably humans, for the treatment of a variety of conditions and disorders, including, but not limited to, atherosclerosis, coronary artery disease, acute coronary syndrome, dyslipidemias and the sequelae thereof, angina, ischemia, cardiac ischemia, myocardial infarction, reperfusion injury, angioplastic restenosis, hypertension, vascular complications of diabetes, obesity or endotoxemia, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors, antihypertensives or other pharmaceutically active material.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, 0-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the myeloperoxidase. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving myeloperoxidase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

VI. Examples

The following Examples have been prepared, isolated and characterized using the methods disclosed herein. The following examples demonstrate a partial scope of the invention and are not meant to be limiting of the scope of the invention.

Intermediate 1. (Z)-3-iodo-3-(3-trityl-5-(tritylamino)-3H-[1,2,3]triazolo[4,5-b]pyridin-7-yl)prop-2-en-1-ol

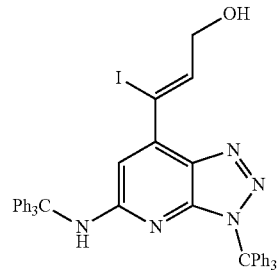

Step A. (E)-4-Bromo-3-((4-chlorophenyl)diazenyl)pyridine-2,6-diamine

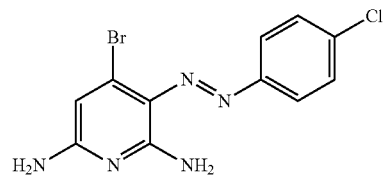 [SMILES: Nc1cc(Br)c(/N=N/c2ccc(Cl)cc2)c(N)n1]

To a solution of 4-chloroaniline (0.678 g, 5.32 mmol) in 6 N HCl (3.37 mL, 20.2 mmol) at 0° C. was added a solution of sodium nitrite (0.367 g, 5.32 mmol) in water (0.581 mL), and the reaction mixture was stirred for 30 min. The reaction was then treated with urea (0.032 g, 0.53 mmol), and poured into a solution of 4-bromopyridine-2,6-diamine (1.00 g, 5.32 mmol) in water (14.5 mL). After 30 min, sodium acetate (1.96 g, 23.9 mmol) was added, and the reaction mixture was allowed to stir ON. The reaction mixture was then filtered, and the filtrate was dried in vacuo to furnish the diazene intermediate (1.19 g, 68.7%). MS(ESI) m/z 328.0 (M+H).

Step B. 4-Bromopyridine-2,3,6-triamine

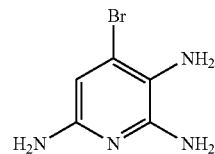

To a solution of the product of Step A (1.2 g, 3.6 mmol) in EtOH (12 mL) was added acetic acid (0.63 mL, 11 mmol) and zinc powder (0.72 g, 11 mmol), and the reaction mixture was heated to 70° C. After 90 min, the reaction mixture was filtered through Celite® and concentrated. The residue was purified by silica gel chromatography to furnish the triamine intermediate (0.57 g, 77%).

Step C. 7-Bromo-3H-[1,2,3]triazolo[4,5-b]pyridin-5-amine

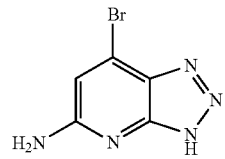 [SMILES: Nc1cc(Br)c2nn[nH]c2n1]

To a solution of the triamine from Step B (0.568 g, 2.80 mmol) in THF (28 mL) was added isoamyl nitrite (0.377 mL, 2.80 mmol). The reaction mixture was stirred ON. The solution was then treated with an additional 0.20 mL of isoamyl nitrite, and the solution was stirred ON. The solution was then concentrated, and the residue purified by silica gel chromatography to furnish the desired triazolopyridine (0.185 g, 30.9%). MS(ESI) m/z 214.0 (M+H).

Step D. 7-Bromo ditrityl-3H-[1,2,3]triazolo[4,5-b]pyridin-5-amine

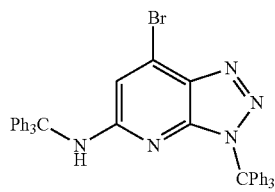

TEA (81.0 mL, 581 mmol) was added to a suspension of diaminotriazolopyridine from Step C (25.0 g, 117 mmol) and trityl chloride (75.0 g, 269 mmol) in DCM (1.5 L), and the reaction mixture was stirred at rt ON. The reaction mixture was concentrated and purified by column chromatography to yield 7-Bromo ditrityl-3H-[1,2,3]triazolo[4,5-b]pyridin-5-amine as a mixture of 2 trityl regioisomers (~15 g, 18%) as a tan solid. MS(ESI) m/z 700.1.

Step E. 3-(3-trityl-5-(tritylamino)-3H-[1,2,3]triazolo[4,5-b]pyridin-7-yl)prop-2-yn-1-ol

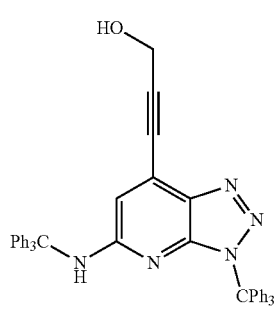

To a solution of the product of Step D (10.0 g, 14.3 mmol) in DMF (48 mL), was added bis(triphenylphosphine)palladium(II) chloride (0.402 g, 0.573 mmol), prop-2-yn-1-ol (1.61 g, 28.6 mmol), copper(I) iodide (0.109 g, 0.573 mmol), and triethylamine (5.98 ml, 42.9 mmol) in a pressure rated sealed tube under an Ar atmosphere. The reaction mixture was heated to 85° C. for 18 hours, and then cooled to rt. The reaction mixture was filtered trough Celite®, and the filtrate was concentrated. The residue was purified by chromatography on silica gel (preflushed with 1% TEA/Hexanes) to provide the alkynol product (6.75 g, 70%). MS(ESI) m/z 674.4 (M+H).

Intermediate 1. A solution the alkynol obtained in step E (6.83 g, 10.1 mmol) in anhydrous THF (43 mL) was added dropwise to a solution of 1M LAH in THF (21.3 mL, 21.3 mmol) and sodium methoxide (55.0 mg, 1.01 mmol) in THF (43 mL) at 0° C. under Ar, and the reaction mixture was stirred for 1 hr at 0° C. Dimethyl carbonate (1.83 g, 20.3 mmol) was then added at 0° C., and the reaction mixture was stirred for 10 min at 0° C. The reaction mixture was then cooled to −78° C., and a solution of iodine (5.15 g, 20.3 mmol) in anhydrous THF (20 mL) was added dropwise. The reaction mixture was allowed to warm to rt and stirred for 1 h, and was then quenched with 20 mL of MeOH, and diluted with water and EtOAc. The layers were separated, and the aqueous phase was extracted 4× with EtOAc. The combined organics were washed with brine, dried with $Na_2SO_4$, filtered and concentrated. The residue was purified by chromatography on silica gel (preflushed with 1% TEA/Hexanes) to provide Intermediate 1, (3.65 g, 45%). MS(ESI) m/z 802.4 (M+H). Major regioisomer II-1 NMR (400 MHz, $CDCl_3$) δ 7.26-7.14 (m, 30H), 6.28 (s, 1H), 5.85 (s, 1H), 4.37 (d, J=5.3 Hz, 2H).

Intermediate 2. (Z)-7-(3-bromo-1-iodoprop-1-en-1-yl)-N,3-ditrityl-3H-[1,2,3]triazolo[4,5-b]pyridin-5-amine

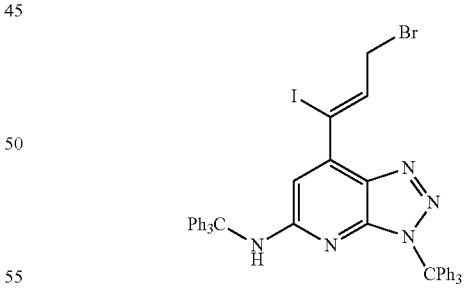

Intermediate 1 (2.50 g, 3.12 mmol) was dissolved in DCM (15.6 mL), and the solution was cooled to 0° C. with stirring under argon. Triphenylphosphine (0.981 g, 3.74 mmol) and $CBr_4$ (1.24 g, 3.74 mmol) were added, and stirring was continued for 1.5 h at 0° C. and then 2 h at rt. The reaction mixture was concentrated, and the residue was purified by flash chromatography to provide Intermediate 2 as a light yellow solid (1.94 g, 72%, isolated as mixture of trityl regioisomers).

Intermediate 3. 4-(4,4,5,5-Tetramethyl-1,3,2-dioxaborolan-2-yl)-1-(3-((triisopropylsilyl)oxy)benzyl)-1H-pyrazole

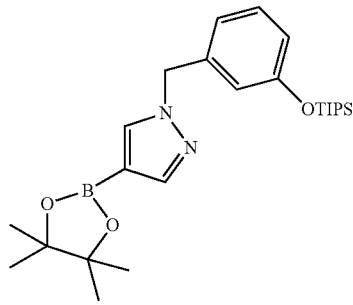

Step A. Methyl 3-((triisopropylsilyl)oxy)benzoate

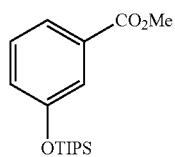

Methyl 3-hydroxybenzoate (10.0 g, 65.7 mmol) and imidazole (5.28 g, 78.0 mmol) were dissolved in DMF (44 mL). The solution was cooled to 0° C. in an ice/salt water bath while triisopropylsilylchloride (15.9 mL, 67.7 mmol) was added dropwise. After completion of addition, stirring was continued in ice bath for ~1 h and then at rt ON. An additional 2.64 g of imidazole (39.0 mmol) and TIPS-Cl (8.0 mL, 34 mmol) were added. The reaction mixture was stirred for another 5 h. The reaction mixture was diluted with water and extracted 3× with diethyl ether. The combined extracts were washed with water and brine, then dried over $Na_2SO_4$, filtered and evaporated. Crude product was purified by flash chromatography to provide methyl 3-((triisopropylsilyl)oxy)benzoate (18.2 g., 90%). MS(ESI) m/z 309.2 (M+H). $^1$H NMR (500 MHz, DMSO-$d_6$) δ 7.56 (d, J=7.7 Hz, 1H), 7.46-7.33 (m, 2H), 7.20-7.11 (m, 1H), 1.32-1.15 (m, 3H), 1.10-1.00 (m, 18H).

Step B. (3-((triisopropylsilyl)oxy)phenyl)methanol

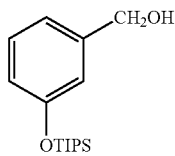

Methyl 3-((triisopropylsilyl)oxy)-benzoate (18.2 g, 59.1 mmol) was dissolved in THF (236 ml) with stirring under argon. The solution was cooled to 0° C., and a 2M solution of $LiBH_4$ in THF (59.1 mL, 118 mmol) was added in rapid dropwise fashion. MeOH (4.78 ml, 118 mmol) was then added slowly dropwise. The reaction mixture was stirred ON allowing the ice to melt, so that reaction mixture gradually assumed rt. The reaction mixture was then heated to reflux for 4-5 h to drive the reaction to completion as determined by LCMS. The reaction mixture was cooled to rt, and then in an ice bath and was quenched with water, then 1M NaOH. EtOAc was added, and the mixture was stirred to dissolve the most of solids. The mixture was transferred to a separatory funnel with additional water. Phases were separated, and aqueous layer reextracted 2× with EtOAc. The remaining solid was carefully dissolved with a little 1M HCl and water, and was added to the aqueous layer which was extracted once more with EtOAc. The combined extracts were washed with brine, then dried over $Na_2SO_4$, filtered and evaporated to yield (3-((triisopropylsilyl)oxy)phenyl)methanol as a colorless liquid (16.0 g, 97%). $^1$H NMR (500 MHz, CDCl$_3$) δ 7.20 (t, J=7.70 Hz, 1H), 6.92 (d, J=7.43 Hz, 1H), 6.90 (d, J=1.93 Hz, 1H), 6.80 (dd, J=1.79, 8.12 Hz, 1H), 4.64 (s, 2H), 1.58 (br s, 1H), 1.20-1.32 (m, 3H), 1.10 (d, J=7.15 Hz, 18H).

Step C. (3-(bromomethyl)phenoxy)triisopropylsilane

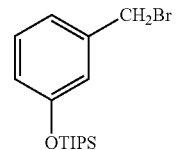

(3-((triisopropylsilyl)oxy)phenyl)methanol (6.87 g, 24.5 mmol) was dissolved in THF (122 ml), and triphenylphosphine (9.64 g, 36.7 mmol) was added. The resulting solution was cooled in an ice bath, and $CBr_4$ (12.2 g, 36.7 mmol) was added. The reaction mixture was stirred for 1.5 h in an ice bath, then ON at rt. The reaction mixture was filtered, and the solid washed with small amounts of THF. The filtrate was evaporated. The crude was purified by flash chromatography to provide the bromide (5.63 g, 66.9%). $^1$H NMR (500 MHz, CDCl$_3$) δ ppm 7.12-7.21 (m, 1H) 6.95 (d, J=7.70 Hz, 1H) 6.91 (t, J=2.06 Hz, 1H) 6.79-6.82 (m, 1H) 4.43 (s, 2H) 1.21-1.30 (m, 3H) 1.09-1.12 (m, 18H).

Intermediate 3. NaH (60% in oil, 0.941 g, 23.5 mmol) was suspended in DMF (15 mL) with stirring under argon at 0° C. A solution of 4-(4,4,5,5-tetramethyl-1,3,2-dioxaborolan-2-yl)-1H-pyrazole (4.15 g, 21.4 mmol) in DMF (20 mL) was added dropwise at a rate to control foaming. The resulting mixture was stirred for 10-15 min at 0° C. (3-(bromomethyl)phenoxy)triisopropylsilane (8.43 g, 24.5 mmol) was then added dropwise along with additional DMF (18 mL). The reaction mixture was stirred for ~1 h at 0° C., then ON at rt. The reaction mixture was quenched with sat'd $NH_4Cl$, diluted with water and extracted 3× with EtOAc. The combined extracts were washed with water, 10% LiCl solution and brine, dried over Na$_2$SO$_4$, filtered and evaporated. The residue was purified by flash chromatography to provide Intermediate 3 as a clear oil (6.0 g, 62%). MS(ESI) m/z 457.2 (M+H). $^1$H NMR (500 MHz, CDCl$_3$) δ 7.82 (s, 1H), 7.65 (s, 1H), 7.18 (t, J=7.8 Hz, 1H), 6.87-6.75 (m, 2H), 6.68 (s, 1H), 5.26 (s, 2H), 1.31 (s, 12H), 1.20 (dd, J=15.0, 7.3 Hz, 3H), 1.11-1.02 (m, 18H).

Intermediate 3 can Also be Prepared Directly from the Benzyl Alcohol of Step B as Follows:

A solution of 4-(4,4,5,5-tetramethyl-1,3,2-dioxaborolan-2-yl)-1H-pyrazole (0.423 g, 2.18 mmol) and (3-((triisopropylsilyl)oxy)phenyl)methanol (0.612 g, 2.18 mmol) in toluene (10.9 mL) was prepared. Tris(butyl)phosphine (0.818 mL, 3.27 mmol) was added, followed by 1,1'-azobis(N,N-dimethylformamide) (0.564 g, 3.27 mmol), and the reaction mixture was stirred at rt ON. The reaction mixture was filtered, the solid was washed with additional toluene, and the filtrate was evaporated. The crude product was purified by flash chromatography to provide Intermediate 3 as a white solid (0.605 g, 61%).

Intermediate 4. (Z)-3-(1-(3-((Triisopropylsilyl)oxy) benzyl)-1H-pyrazol-4-yl)-3-(3-trityl-5-(tritylamino)-3H-[1,2,3]triazolo[4,5-b]pyridin-7-yl)prop-2-en-1-ol

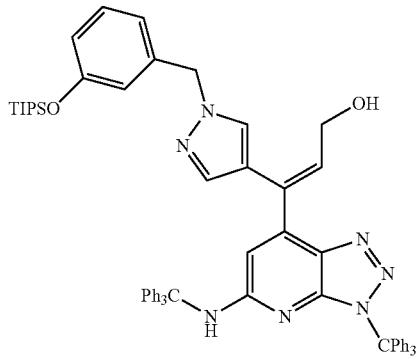

To a solution of K$_2$CO$_3$ (4.29 g, 31.0 mmol) in water (25 mL) was added Intermediate 3 (4.47 g, 9.79 mmol) and Intermediate 1 (4.98 g, 6.21 mmol) in 30 mL of THF, in a pressure rated flask. The mixture was degassed with Ar, and then PdCl$_2$(dppf)-CH$_2$Cl$_2$ adduct (0.507 g, 0.621 mmol) was added. The flask was capped and heated to 80° C. for 3 h. After the reaction was cooled to rt, it was diluted with EtOAc and water, and the phases were separated. The aqueous layer was extracted twice with EtOAc, and the combined organic layers were washed with brine, dried over Na$_2$SO$_4$, and concentrated. The residue was purified by chromatography on silica gel (preflushed with 1% TEA/Hexanes) to provide the product, (5.75 g, 92%). MS(ESI) m/z 1004.5 (M+H). $^1$H NMR (500 MHz, CD$_3$OD) δ 7.31-7.22 (m, 11H), 7.22-7.15 (m, 17H), 7.11 (s, 1H), 7.07-7.03 (m, 6H), 6.86-6.80 (m, 1H), 6.73 (s, 1H), 5.96 (s, 1H), 5.17 (s, 2H), 4.18 (d, J=6.6 Hz, 2H), 1.30-1.23 (m, 3H), 1.10 (d, J=7.4 Hz, 18H).

Intermediate 5. (Z)-3-(1-(3-((Triisopropylsilyl)oxy) benzyl)-1H-pyrazol-4-yl)-3-(3-trityl-5-(tritylamino)-3H-[1,2,3]triazolo[4,5-b]pyridin-7-yl)acrylaldehyde

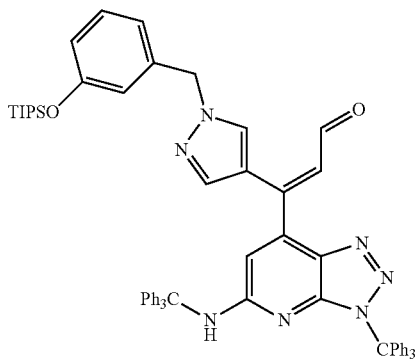

To a solution of Intermediate 4 (4.0 g, 4.0 mmol) in DCM (133 mL) was added manganese dioxide (3.8 g, 44 mmol). The reaction mixture was stirred at rt ON, and was then filtered through a pad of Celite. The solids were washed with DCM. The filtrate was evaporated to give the product as a dark yellow foam (3.92 g, 92%). MS(ESI) m/z 1002.5 (M+H). $^1$H NMR (500 MHz, CDCl$_3$) δ 9.68 (d, J=7.70 Hz, 1H), 7.44 (d, J=7.70 Hz, 1H), 7.22-7.30 (m, 12H), 7.14-7.22 (m, 14H), 7.10 (s, 1H), 6.98-7.07 (m, 6H), 6.82 (dd, J=2.06, 7.84 Hz, 1H), 6.72 (d, J=1.93 Hz, 1H), 6.68 (d, J=7.43 Hz, 1H), 5.89 (s, 1H), 5.84 (s, 1H), 5.06 (s, 2H), 1.16-1.28 (m, 3H), 1.01-1.12 (m, 18H).

Intermediate 6. tert-butyl ((1S,3S,4S)-3-benzyl-4-hydroxycyclopentyl)carbamate

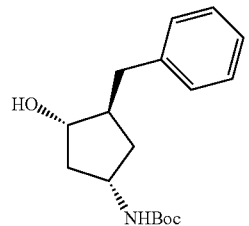 [SMILES: CC(C)(C)OC(=O)N[C@H]1C[C@H](Cc2ccccc2)[C@@H](O)C1]

To a stirred solution of racemic tert-butyl cis-6-oxabicyclo[3.1.0]hexan-3-ylcarbamate (27.0 g, 136 mmol) in THF (500 mL), benzylmagnesium chloride (203 mL, 407 mmol) was added at 0° C., and then the mixture was allowed to warm to rt and stirred for 3 hrs. The reaction mixture was quenched with NH$_4$Cl solution and extracted into EtOAc twice. The combined organic layer was dried over Na$_2$SO$_4$ and concentrated. The crude product was purified by flash chromatography to afford an off white solid. Chiral SFC separation (Chiralpak IC, 30×250 mm, 5μ column eluted with 10% MeOH/90% CO$_2$ at 150 mL/min, 150 Bar, 40° C.) of the product mixture provided 10.2 g of each isomer in >99.5% ee. Intermediate 6: MS(ESI) m/z 292.5 (M+H). $^1$H NMR (500 MHz, DMSO-$d_6$) δ 7.32-7.23 (m, 2H), 7.21-7.08 (m, 3H), 6.74 (br d, J=7.2 Hz, 1H), 4.76 (d, J=5.2 Hz, 1H), 3.82-3.67 (m, 1H), 3.64-3.52 (m, 1H), 2.87 (dd, J=13.3, 4.8 Hz, 1H), 2.29 (dd, J=13.5, 9.9 Hz, 1H), 2.20-2.09 (m, 1H), 2.05-1.94 (m, 1H), 1.54-1.41 (m, 2H), 1.35 (s, 9H). The absolute configuration of Intermediate 6 was assigned based on the X-ray crystallography of a co-crystal of final macrocyclic product, Ex. 26 complexed with MPO.

Intermediate 7. (3R,4S)-4-Benzylpyrrolidin-3-ol hydrochloride

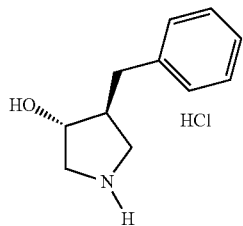 [SMILES: O[C@H]1CNC[C@@H]1Cc1ccccc1 ; Cl]

Intermediate 7 was prepared following the procedure described in Intermediate 6 by using racemic tert-butyl 6-oxa-3-azabicyclo[3.1.0]hexane-3-carboxylate as the starting material, followed by SFC chiral separation (Chiralpak AD, 30×250 mm, 5μ column eluted with 10% MeOH/90% $CO_2$ at 75 mL/min, 150 Bar, 40° C., Peak 2, >99.5% ee) and removal of the Boc-protecting group with 4N HCl in dioxane to provide the title compound as its hydrochloride salt. MS(ESI) m/z 278.1 (M+H). The absolute configuration was not determined.

Intermediate 8. (Z)-3-iodo-3-(3-trityl-5-(tritylamino)-3H-[1,2,3]triazolo[4,5-b]pyridin-7-yl)acrylaldehyde

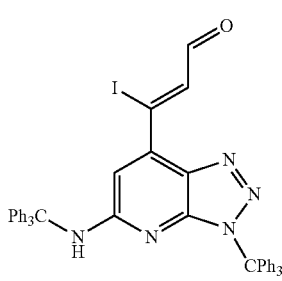

Intermediate 1 (0.203 g, 0.253 mmol) was dissolved in DCM (8.44 mL), and manganese dioxide (0.330 g, 3.80 mmol) was added. The mixture was stirred at room temperature for 3 h. The reaction mixture was filtered through a pad of Celite, and the solids were washed thoroughly with DCM. The filtrate was evaporated to give Intermediate 8 as a bright yellow solid (200 mg, 99%). MS(ESI) m/z 800.2 (M+H).

Intermediate 9. (S)-4-Amino-1phenylbicyclo[2.2.2]octan-2-ol, TFA salt

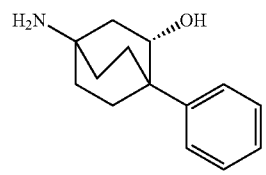 [SMILES: NC12CCC(c3ccccc3)(CC1)[C@@H](O)C2]

Step A. 4-(Benzylamino)-1-(4-bromophenyl)bicyclo[2.2.2]octan-2-ol

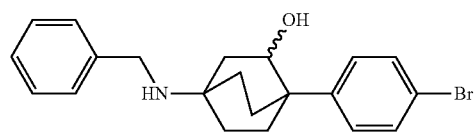 [SMILES: OC1CC2(NCc3ccccc3)CCC1(c1ccc(Br)cc1)CC2]

To a solution of the ketone from Intermediate 5, Step D (7.03 g, 18.3 mmol) dissolved in EtOH (340 mL) at 0° C. was added $NaBH_4$ (1.04 g, 27.4 mmol), and the reaction mixture was stirred at rt for 3 days. The reaction mixture was concentrated, partitioned between brine and EtOAc, and the aqueous layer was separated and washed 1× with EtOAc. The combined organic layers were dried over $MgSO_4$, and purified via flash chromatography to furnish 4-(benzylamino)-1-(4-bromophenyl)bicyclo[2.2.2]octan-2-ol (5.3 g, 75%). MS(ESI) m/z 388.0 (M+H).

Step B. tert-Butylbenzyl(4-(4-bromophenyl)-3-oxobicyclo[2.2.2]octan-1-yl)carbamate

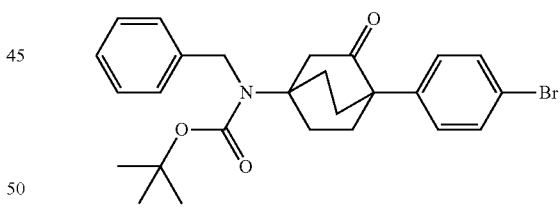

To a solution of the intermediate amine from Step A (5.0 g, 13 mmol) in THF (22 mL) was added 1N NaOH (22 mL) followed by $Boc_2O$ (3.0 mL, 13 mmol). The biphasic mixture was stirred ON at 50° C. Additional $Boc_2O$ (3.0 mL, 13 mmol) was added, and the reaction mixture was again stirred ON. The reaction mixture was partitioned between EtOAc and water, and the organic phase was dried over $MgSO_4$, filtered and concentrated. The residue was purified by flash chromatography to furnish tert-butyl benzyl(4-(4-bromophenyl)-3-oxobicyclo[2.2.2]octan-1-yl)carbamate (3.0 g, 6.2 mmol, 48%), $^1$H NMR (400 MHz, CDCl$_3$) δ 7.43 (d, J=8.6 Hz, 2H), 7.37-7.30 (m, 2H), 7.30-7.22 (m, 1H), 7.20 (d, J=7.3 Hz, 2H), 7.04-6.93 (m, 2H), 4.63 (s, 2H), 3.06 (s, 2H), 2.37-2.07 (m, 6H), 2.05-1.92 (m, 2H), 1.47 (s, 9H). MS(ESI) m/z 430.0 (M+H-tBu).

Step C. tert-Butyl(S)-benzyl(4-(4-bromophenyl)-3-hydroxybicyclo[2.2.2]octan-1-yl)carbamate

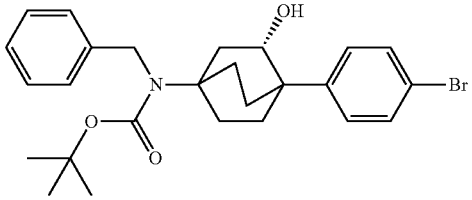 [SMILES: CC(C)(C)OC(=O)N(Cc1ccccc1)C12CCC(c3ccc(Br)cc3)(CC1)[C@@H](O)C2]

To a solution of the ketone of Step B (2.0 g, 4.1 mmol) in EtOH (41 mL) at 0° C. was added NaBH$_4$ (0.16 g, 4.1 mmol), and the reaction mixture was stirred for 1 hour. The reaction mixture was diluted with water, and the resultant precipitate was filtered and dried under vacuum ON to furnish racemic tert-butyl benzyl(4-(4-bromophenyl)-3-hydroxybicyclo[2.2.2]octan-1-yl)carbamate (1.6 g, 80%), $^1$H NMR (400 MHz, CDCl$_3$) 7.43 (d, J=8.6 Hz, 2H), 7.34-7.28 (m, 2H), 7.24-7.15 (m, 5H), 4.59 (s, 2H), 4.13-4.04 (m, 1H), 2.73 (ddd, J=13.1, 9.5, 3.1 Hz, 1H), 2.40-2.29 (m, 1H), 2.25-2.12 (m, 2H), 2.10-1.98 (m, 2H), 1.94 (dt, J=13.4, 3.1 Hz, 1H), 1.91-1.83 (m, 1H), 1.77-1.62 (m, 2H), 1.44 (s, 9H), 1.23 (d, J=2.6 Hz, 1H). MS(ESI) m/z 386.1/388.1 (M+H-Boc). The enantiomers were separated by Chiral SFC (Chiralpak OJ-H eluted with 15% MeOH/85% CO at 150 bar and 40° C.) to provide tert-butyl (S)-benzyl(4-(4-bromophenyl)-3-hydroxybicyclo[2.2.2]octan-1-yl)carbamate and tert-butyl (R)-benzyl(4-(4-bromophenyl)-3-hydroxybicyclo[2.2.2]octan-1-yl)carbamate in >99.5% ee.

Intermediate 9. tert-Butyl (S)-benzyl(4-(4-bromophenyl)-3-hydroxybicyclo[2.2.2]octan-1-yl)carbamate was dissolved in DCM (40 mL) and TFA (8 mL), and the mixture was stirred for 1 h. The reaction mixture was concentrated, and the residue taken up in 200 mL of EtOH and 10% Pd—C (0.58 g) was added. This mixture was stirred under 55 psi hydrogen gas ON. The catalyst was removed by filtration through Celite. The filtrate was evaporated to provide the title compound, which was used without further purification. MS(ESI) 217.9 (M+H).

Intermediate 10. (R)-4-Amino-1phenylbicyclo[2.2.2]octan-2-ol, TFA Salt

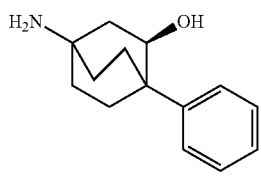 [SMILES: NC12CCC(c3ccccc3)(CC1)[C@H](O)C2]

Intermediate 10 was prepared from tert-butyl (R)-benzyl (4-(4-bromophenyl)-3-hydroxybicyclo[2.2.2]octan-1-yl)carbamate as described for Intermediate 9. MS(ESI) 217.9 (M+H).

Example 1

7-{17-oxa-3,4,10-triazatetracyclo[16.3.1.1$^{3,6}$.1$^{12,1^6}$]tetracosa-1(22),4,6(24),12,14,16(23),18,20-octaen-7-yl}-3H-[1,2,3]triazolo[4,5-b]pyridin-5-amine 2TFA

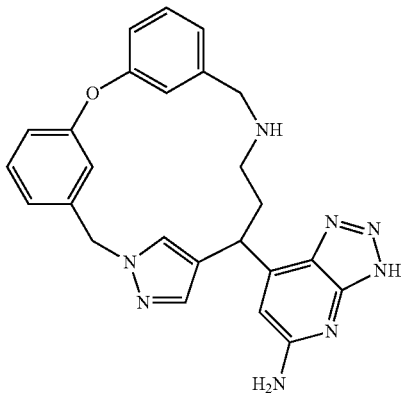 [SMILES: Nc1cc(C2CCNCc3cccc(c3)Oc3cccc(c3)Cn3cc2cn3)c2nn[nH]c2n1]

1A. (Z)-7-(3-((3-iodobenzyl)amino)-1-(1-(3-((triisopropylsilyl)oxy)benzyl)-1H-pyrazol-4-yl)prop-1-en-1-yl)-N,3-ditrityl-3H-[1,2,3]triazolo[4,5-b]pyridin-5-amine

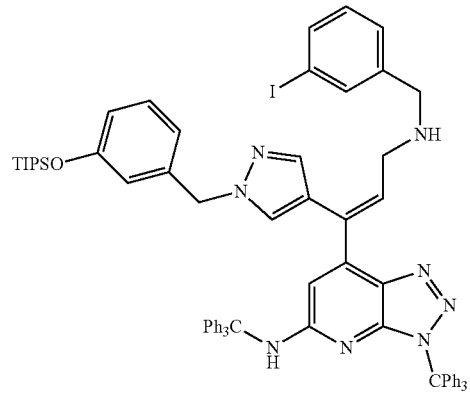

To a solution of Intermediate 5 (1.5 g, 1.5 mmol) and TEA (1.3 mL, 9.0 mmol) in EtOH (17 mL) was added (3-iodophenyl)methanamine, HCl (1.2 g, 4.5 mmol). The reaction solution was heated to 60° C. for 4 hours. After cooling to rt, THF (14 mL) was added to the solution, followed by NaBH$_4$ (0.31 g, 8.2 mmol). The reaction mixture was allowed to stir at rt for 18 h. The reaction mixture was partitioned between EtOAc and 1N NaOH, and the phases were separated. The aqueous layer was extracted twice with EtOAc, and the combined organic layers were washed with brine, dried over Na$_2$SO$_4$, and concentrated. The residue was purified by chromatography on silica gel (preflushed with 1% TEA/Hexanes) to provide the product (0.443 g, 24%). MS(ESI) m/z 1219.6 (M+H).

1B: (Z)-3-((4-(3-((3-iodobenzyl)amino)-1-(3-trityl-5-(tritylamino)-3H-[1,2,3]triazolo[4,5-b]pyridin-7-yl)prop-1-en-1-yl)-1H-pyrazol-1-yl)methyl)phenol

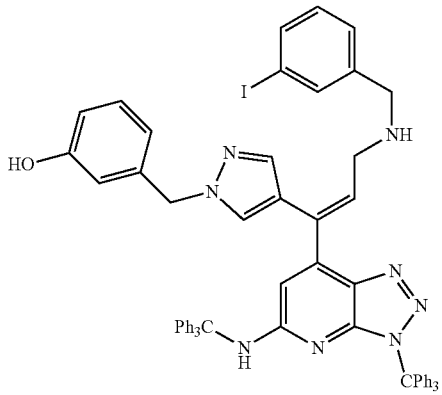

To a solution of 1A (443 mg, 0.363 mmol) in THF (3.63 mL) was added TBAF (1.09 mL, 1.09 mmol). The reaction solution was stirred at rt for 18 h. The mixture was diluted with EtOAc and water, and the phases were separated. The aqueous layer was extracted twice with EtOAc, and the combined organic layers were washed with brine, dried over $Na_2SO_4$, and concentrated. The residue was purified by chromatography on silica gel (preflushed with 1% TEA/Hexanes) to provide the product, (271 mg, 70%). MS(ESI) m/z 1063.4 (M+H).

1C: 3-((4-(3-((3-iodobenzyl)amino)-1-(3-trityl-5-(tritylamino)-3H-[1,2,3]triazolo[4,5-b]pyridin-7-yl)propyl)-1H-pyrazol-1-yl)methyl)phenol

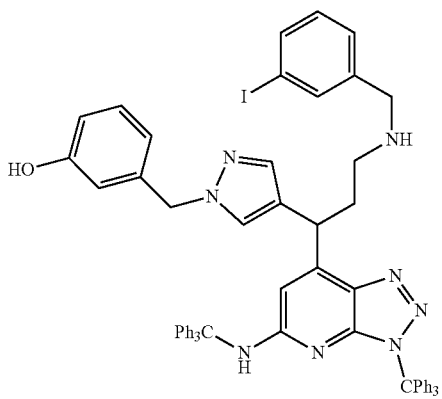

To a solution of 1B (67 mg, 0.063 mmol) and nickel (II) chloride (41 mg, 0.32 mmol) in MeOH (3 mL) and THF (1.2 mL) at 0° C. was added $NaBH_4$ (19 mg, 0.51 mmol). The reaction mixture was stirred for 45 min at 0° C., and then quenched with saturated aq. $NH_4Cl$. The mixture was partitioned between EtOAc and 1N NaOH, and the phases were separated. The aqueous layer was extracted twice with EtOAc, and the combined organic layers were washed with brine, dried over $Na_2SO_4$, and concentrated to provide 1C (68 mg, 100%). MS(ESI) m/z 1065.6 (M+H).

1D: 7-{17-oxa-3,4,10-triazatetracyclo[16.3.1.$1^{3,6}.1^{12,16}$]tetracosa-1(22),4,6(24),12,14,16(23),18,20-octaen-7-yl}-N,3-bis(triphenylmethyl)-3H-[1,2,3]triazolo[4,5-b]pyridin-5-amine

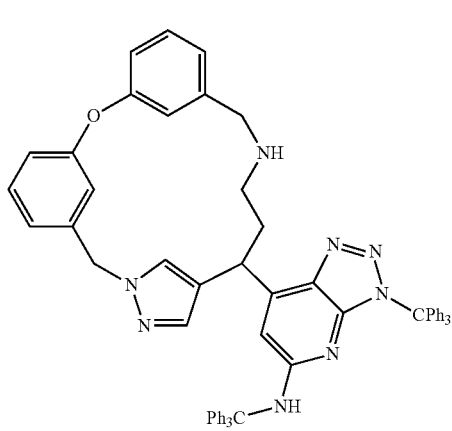

In a sealed vial, a suspension of 1C (67 mg, 0.063 mmol), CuI (13 mg, 0.069 mmol), 1,10-phenanthroline (25 mg, 0.14 mmol), and $Cs_2CO_3$ (62 mg, 0.19 mmol) in toluene (13 mL) was heated to 150° C. for 2 h. The reaction was filtered through a pad of Celite and concentrated. The residue was purified by chromatography on silica gel (preflushed with 1% TEA/Hexanes) to provide the 1D (17 mg, 29%). MS(ESI) m/z 937.6 (M+H).

Example 1

To a solution of 1D (31 mg, 0.033 mmol) in DCM (1 mL) was added TFA (0.10 mL, 1.3 mmol). After stirring at rt for 1 h, the reaction was quenched with $Et_3SiH$ (0.011 mL, 0.066 mmol), and the reaction mixture was concentrated. The crude residue was titruated with hexanes, and the product was purified by RP prep HPLC to provide the title compound as its TFA salt (6.2 mg, 26%). MS(ESI) m/z 453.0 (M+H). $^1$H NMR (500 MHz, $CD_4OD$) δ 7.71 (s, 1H), 7.54 (t, J=8.0 Hz, 1H), 7.48 (s, 1H), 7.43 (t, J=7.8 Hz, 1H), 7.30 (d, J=7.7 Hz, 1H), 7.26-7.18 (m, 1H), 7.18-7.08 (m, 2H), 6.94 (t, J=1.9 Hz, 1H), 6.66 (s, 1H), 6.01 (t, J=1.8 Hz, 1H), 5.33 (s, 2H), 4.51 (dd, J=12.4, 3.0 Hz, 1H), 4.35 (d, J=13.2 Hz, 1H), 4.08 (d, J=13.2 Hz, 1H), 2.98-2.87 (m, 1H), 2.66-2.53 (m, 2H), 2.51-2.39 (m, 1H). Analytical HPLC: RT=4.23 min (Method A).

Example 2

7-{18-oxa-3,4,10-triazatetracyclo[17.3.1.$1^{3,6}.1^{12,16}$]pentacosa-1(23),4,6(25),12,14,16(24),19,21-octaen-7-yl}-3H-[1,2,3]triazolo[4,5-b]pyridin-5-amine, 2TFA

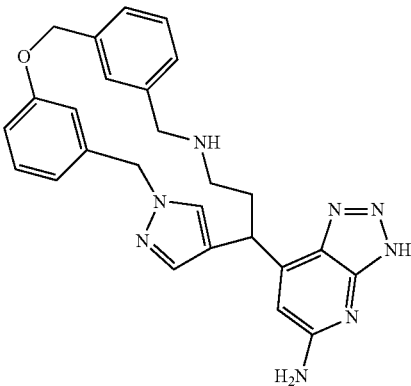 [SMILES: Nc1cc(C2CCNCc3cccc(c3)COc3cccc(c3)Cn3cc2cn3)c2nn[nH]c2n1]

2A. 3-((4-(3-((3-(hydroxymethyl)benzyl)amino)-1-(3-trityl-5-(tritylamino)-3H-[1,2,3]triazolo[4,5-b]pyridin-7-yl)propyl)-1H-pyrazol-1-yl)methyl)phenol

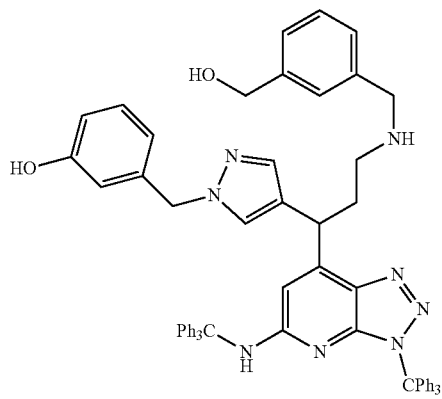

2A was prepared from Intermediate 5 and (3-(aminomethyl)phenyl)methanol in two steps using the procedures described for 1A and 1B. MS(ESI) m/z 1123.6 (M+H).

2B. 7-{18-oxa-3,4,10-triazatetracyclo[17.3.1.1³,⁶.1¹²,¹⁶]pentacosa-1(23),4,6(25),12,14,16(24),19,21-octaen-7-yl}-N,3-bis(triphenylmethyl)-3H-[1,2,3]triazolo[4,5-b]pyridin-5-amine

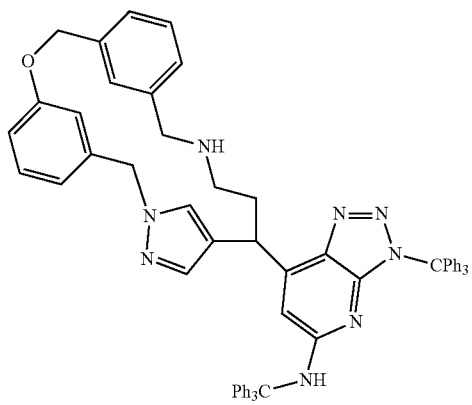

A solution of 2A (0.017 g, 0.018 mmol) and PPh₃ (0.014 g, 0.053 mmol) was bubbled with Ar for 5 mins. The solution was cooled to 0° C., and a solution of DIAD (0.010 mL, 0.053 mmol) in THF (1.5 mL) was added dropwise over 20 mins. After an additional 20 mins, the reaction was allowed to warm to rt and stirred for 2 days. The reaction mixture was concentrated, and the residue was purified by flash chromatography on silica gel pre-treated with 1% TEA in hexanes to give 2B (16 mg, 94%). MS(ESI) m/z 951.4 (M+H).

Example 2 was prepared by deprotection of 2B with TFA as described for Example 1. MS(ESI) m/z 467.1 (M+H). ¹H NMR (500 MHz, CD₄OD) δ 7.60 (s, 1H), 7.46-7.37 (m, 3H), 7.37-7.26 (m, 3H), 7.05 (dd, J=8.1, 2.1 Hz, 1H), 6.99 (d, J=7.4 Hz, 1H), 6.45 (br. s., 1H), 6.30 (s, 1H), 5.33-5.16 (m, 4H), 4.47 (dd, J=11.8, 3.0 Hz, 1H), 4.33 (d, J=13.5 Hz, 1H), 4.16 (d, J=13.2 Hz, 1H), 3.00-2.86 (m, 1H), 2.74-2.61 (m, 1H), 2.58-2.48 (m, 1H), 2.48-2.36 (m, 1H). Analytical HPLC: RT=4.26 min (Method A).

Example 3

7-{18-oxa-3,4,10-triazatetracyclo[17.3.1.1³,⁶.1¹³,¹⁷]pentacosa-1(23),4,6(25),13,15,17(24),19,21-octaen-7-yl}-3H-[1,2,3]triazolo[4,5-b]pyridin-5-amine, 2TFA

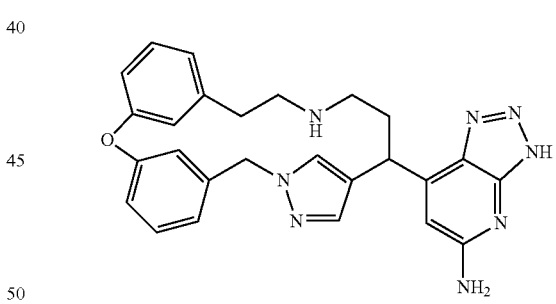

Example 3 was prepared from Intermediate 5 and 2-(3-bromophenyl)ethanamine using the procedures described for Example 1. MS(ESI) m/z 467.2 (M+H). ¹H NMR (500 MHz, CD₄OD) δ 7.78 (s, 1H), 7.53 (s, 1H), 7.48-7.36 (m, 2H), 7.21-7.13 (m, 2H), 7.10 (d, J=6.6 Hz, 1H), 6.99 (d, J=8.5 Hz, 1H), 6.74 (s, 1H), 6.47 (br. s., 1H), 6.18 (s, 1H), 5.32 (s, 2H), 4.43 (dd, J=11.6, 3.6 Hz, 1H), 3.53-3.41 (m, 2H), 3.02-2.96 (m, 2H), 2.96-2.90 (m, 1H), 2.71-2.60 (m, 1H), 2.52-2.39 (m, 2H). Analytical HPLC: RT=4.46 min (Method A).

Example 4

7-{18-oxa-3,4,10-triazatetracyclo[17.3.1.1$^{3,6}$.1$^{13,17}$]pentacosa-1(23),4,6(25),13,15,17(24),19,21-octaen-7-yl}-3H-[1,2,3]triazolo[4,5-b]pyridin-5-amine, 2TFA, Enantiomer A, and

Example 5

7-{18-oxa-3,4,10-triazatetracyclo[17.3.1.1$^{3,6}$.1$^{13,17}$]pentacosa-1(23),4,6(25),13,15,17(24),19,21-octaen-7-yl}-3H-[1,2,3]triazolo[4,5-b]pyridin-5-amine, 2TFA, Enantiomer B

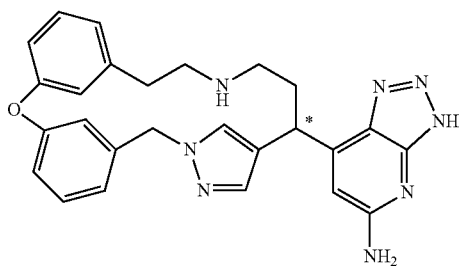 [SMILES: Nc1cc(C2CCNCCc3cccc(c3)Oc3cccc(c3)Cn3cc2cn3)c2nn[nH]c2n1]

Example 3 (31 mg, 0.066 mmol) was separated by chiral SFC separation (Chiralpak IC-H, 21×250 mm, 5 micron; mobile phase: 35% IPA-DEA/65% CO$_2$; 50 mL/min, 150 Bar, 40° C.). The first eluting peak at 10.29 mins provided Example 4 (8.4 mg, 18%). MS(ESI) m/z 467.1 (M+H). $^1$H NMR (500 MHz, CD$_4$OD) δ 7.83 (s, 1H), 7.56 (s, 1H), 7.43 (q, J=7.9 Hz, 2H), 7.19 (t, J=7.3 Hz, 2H), 7.12 (dt, J=8.0, 1.2 Hz, 1H), 7.00 (dd, J=6.9, 1.1 Hz, 1H), 6.75 (s, 1H), 6.67 (s, 1H), 6.18 (s, 1H), 5.34 (s, 2H), 4.48 (dd, J=11.8, 3.3 Hz, 1H), 3.58-3.40 (m, 2H), 3.06-2.91 (m, 3H), 2.70-2.61 (m, 1H), 2.59-2.43 (m, 2H). Analytical HPLC: RT=4.52 min (Method A). The second eluting peak at 17.07 min provided Example 5 (7.5 mg, 16%). MS(ESI) m/z 467.1 (M+H). $^1$H NMR (500 MHz, CD$_4$OD) δ 7.81 (s, 1H), 7.54 (d, J=0.5 Hz, 1H), 7.41 (q, J=8.0 Hz, 2H), 7.22-7.12 (m, 2H), 7.10 (dt, J=6.9, 1.3 Hz, 1H), 7.02-6.95 (m, 1H), 6.74 (t, J=1.9 Hz, 1H), 6.63 (s, 1H), 6.16 (t, J=1.8 Hz, 1H), 5.32 (s, 2H), 4.46 (dd, J=11.7, 3.4 Hz, 1H), 3.56-3.42 (m, 2H), 3.05-2.86 (m, 3H), 2.71-2.59 (m, 1H), 2.56-2.39 (m, 2H). Analytical HPLC: RT=4.45 min (Method A).

Example 6

7-{10-methyl-17-oxa-3,4,10-triazatetracyclo[16.3.1.1$^{3,6}$.1$^{12,16}$]tetracosa-1(22),4,6(24),12,14,16(23),18,20-octaen-7-yl}-3H-[1,2,3]triazolo[4,5-b]pyridin-5-amine, 2TFA

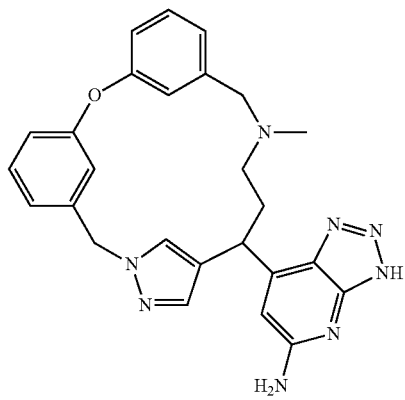 [SMILES: CN1CCC(c2cc(N)nc3[nH]nnc23)c2cnn(c2)Cc2cccc(c2)Oc2cccc(c2)C1]

Example 6A. 7-{10-methyl-17-oxa-3,4,10-triazatetracyclo[16.3.1.1$^{3,6}$.1$^{12,16}$]tetracosa-1(22),4,6(24),12,14,16(23),18,20-octaen-7-yl}-N,3-bis(triphenylmethyl)-3H-[1,2,3]triazolo[4,5-b]pyridin-5-amine, 2 TFA

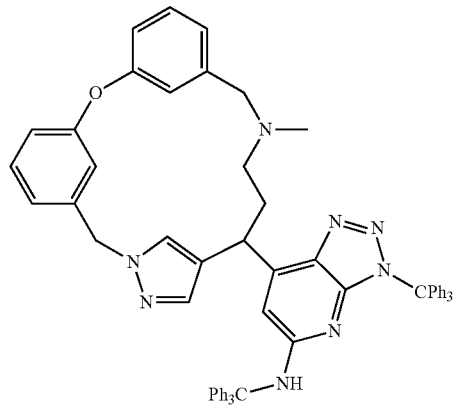

To a solution of 1D (32 mg, 0.034 mmol) in THF (0.69 mL) at 0° C., was added K$_2$CO$_3$ (14 mg, 0.10 mmol) followed by Met (0.10 mL, 0.05 mmol). The solution was allowed to warm to rt and stirred for 3 h. The reaction mixture was quenched with water and extracted with EtOAc. The combined extracts were washed with brine, dried over Na$_2$SO$_4$ and concentrated to give 6A (32.8 mg, 100%). MS(ESI) m/z 951.6 (M+H).

Example 6 was prepared by deprotection of 6A with TFA as described for Example 1. MS(ESI) m/z 467.2 (M+H). $^1$H NMR (500 MHz, CD$_4$OD) δ 7.71 (s, 1H), 7.62-7.56 (m, 1H), 7.54-7.39 (m, 2H), 7.37 (d, J=7.4 Hz, 1H), 7.29-7.21 (m, 1H), 7.20-7.08 (m, 2H), 7.05-6.93 (m, 1H), 6.64 (br. s., 1H), 5.78 (br. s., 1H), 5.35 (s, 2H), 4.64-4.48 (m, 1H), 4.37 (d, J=13.2 Hz, 1H), 4.10 (d, J=13.2 Hz, 1H), 3.10 (s, 3H), 3.06-2.98 (m, 1H), 2.96-2.85 (m, 1H), 2.79-2.67 (m, 1H), 2.56-2.39 (m, 1H). Analytical HPLC: RT=4.27 min (Method A).

Example 7

7-[(11S)-11-Methyl-18-oxa-3,4,10-triazatetracyclo [17.3.1.1$^{3,6}$.1$^{13,17}$]pentacosa-1(23),4,6(25),13,15,17 (24),19,21-octaen-7-yl]-3H-[1,2,3]triazolo[4,5-b] pyridin-5-amine, 2TFA

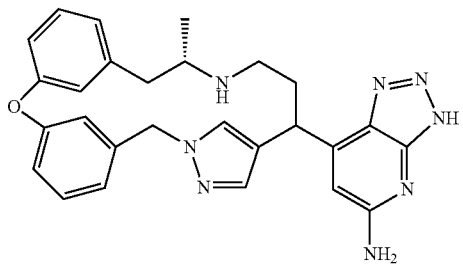

7A. (S)—N—((S)-1-(3-Bromophenyl)propan-2-yl)-2-methylpropane-2-sulfinamide

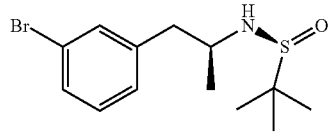 [SMILES: C[C@@H](Cc1cccc(Br)c1)N[S@@](=O)C(C)(C)C]

To a solution of 1-(3-bromophenyl)propan-2-one (1.0 g, 4.7 mmol) and (S)-2-methylpropane-2-sulfinamide (0.63 g, 5.2 mmol) in THF (16 mL) was added titanium (IV) isopropoxide (2.8 mL, 9.4 mmol). The reaction solution was heated to 60° C. for 18 h. The solution was cooled to rt, then added dropwise to a solution of NaBH$_4$ (0.73 g, 19 mmol) in THF (10 mL) at −40 to −50° C. The resulting mixture was warmed up to 10° C. during a 1.5 h period, and then MeOH was added dropwise until gas evolution stopped. The mixture was stirred at rt for 20 min, then filtered through Celite, and the solids rinsed with EtOAc. The filtrate was washed with brine, dried over Na$_2$SO$_4$, filtered and concentrated. The crude product was purified by flash chromatography to give 7A (0.88 g, 59%). MS(ESI) m/z 319.8 (M+H). 1H NMR (500 MHz, CDCl3) δ 7.39 (tt, J=3.9, 1.9 Hz, 2H), 7.24-7.12 (m, 2H), 3.67 (dd, J=6.3, 5.5 Hz, 1H), 2.90-2.76 (m, 2H), 1.23-1.15 (m, 12H).

7B. Methyl 3-(3-((S)-2-((S)-1,1-dimethylethylsulfinamido)propyl)phenoxy)benzoate

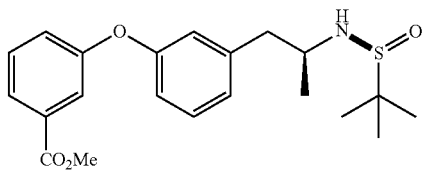

7A (0.88 mg, 2.8 mmol) and methyl 3-hydroxybenzoate (0.42 g, 2.8 mmol) were dissolved in dioxane (11 mL). Cesium carbonate (0.27 g, 8.3 mmol), copper(I) iodide (0.53 g, 2.8 mmol) and 2-(dimethylamino)acetic acid (0.28 mg, 2.8 mmol) were added. Ar was bubbled through mixture for 5 min, then the reaction mixture was heated at 105° C. ON. The mixture was cooled to rt, diluted with ethyl acetate (25 mL), and washed with 1N HCl. The aqueous layer was extracted with EtOAc (4×), and the combined extracts were washed with brine and concentrated. The crude was purified by silica gel chromatography to provide 7B as a clear oil (0.34 g., 32% yield). MS(ESI) m/z 390.0 (M+H).

7C (S)—N—((S)-1-(3-(3-(Hydroxymethyl)phenoxy)phenyl)propan-2-yl)-2-methylpropane-2-sulfinamide

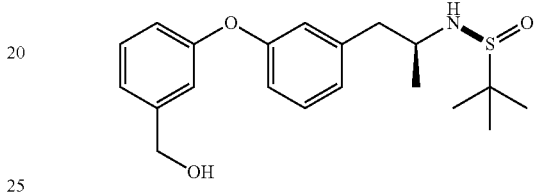

7B (0.17 g, 0.44 mmol) was dissolved in THF (0.9 mL) with stirring under argon at rt. A solution of lithium borohydride (2M in THF, 0.44 mL, 0.87 mmol) was added in rapid dropwise fashion. MeOH (0.035 mL, 0.87 mmol) was then added slowly dropwise. The reaction mixture was stirred at rt for 1.5 h. The reaction mixture was then cooled in an ice bath and quenched with water, then 1M NaOH. EtOAc was added, and mixture was stirred to dissolve the solids. Mixture was transferred to a separatory funnel with additional water to help dissolve the remaining white solid. The phases were separated, and the aqueous layer was reextracted 2× with EtOAc. The combined extracts were washed with brine, then dried over Na$_2$SO$_4$, filtered and evaporated to provide 7C (0.146 g, 93%) as a viscous oil. MS(ESI) m/z 362.0 (M+H).

7D. (S)-2-Methyl-N—((S)-1-(3-(3-((4-(4,4,5,5-tetramethyl-1,3,2-dioxaborolan-2-yl)-1H-pyrazol-1-yl) methyl)phenoxy)phenyl)propan-2-yl)propane-2-sulfinamide

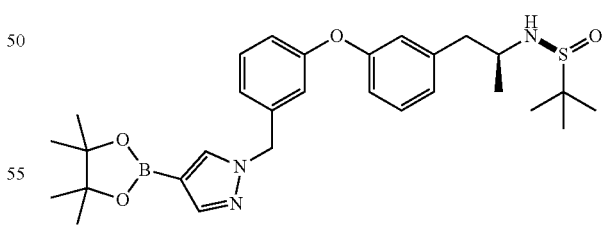

A mixture of 4-(4,4,5,5-tetramethyl-1,3,2-dioxaborolan-2-yl)-1H-pyrazole (65.5 mg, 0.338 mmol) and 7C was dissolved in toluene (0.17 mL). Tris(butyl)phosphine (0.134 mL, 0.540 mmol) was added, followed by TMAD (93 mg, 0.54 mmol), and the reaction mixture was stirred at rt ON. The reaction mixture was filtered, and the filtrate was concentrated. The residue was purified by silica gel chromatography to provide 7D as a clear oil (0.141 mg, 78%) MS(ESI) m/z 538.2 (M+H).

7E. (S)-1-(3-(3-((4-(4,4,5,5-t\Tetramethyl-1,3,2-dioxaborolan-2-yl)-1H-pyrazol-1-yl)methyl)phenoxy)phenyl)propan-2-amine, HCl

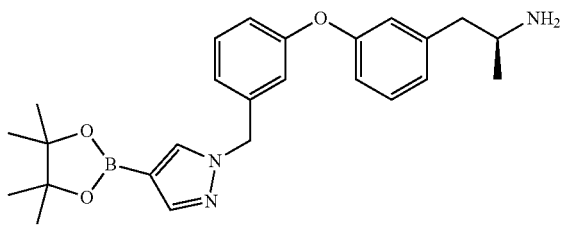 [SMILES: C[C@H](N)Cc1cccc(Oc2cccc(Cn3cc(B4OC(C)(C)C(C)(C)O4)cn3)c2)c1]

To a solution of 7D (0.141 g, 0.262 mmol) in dioxane (2 mL) was added a solution of 4M HCl in dioxane (0.655 mL, 2.62 mmol), and the mixture was stirred at rt for 1 h. The solvent was evaporated, and the residue was triturated with Et$_2$O to give 7E (112 mg, 98%) as a white solid. MS(ESI) m/z 434.1 (M+H).

7F. (S,Z)-tert-Butyl (3-iodo-3-(3-trityl-5-(tritylamino)-3H-[1,2,3]triazolo[4,5-b]pyridin-7-yl)allyl) (1-(3-(3-((4-(4,4,5,5-tetramethyl-1,3,2-dioxaborolan-2-yl)-1H-pyrazol-1-yl)methyl)phenoxy)phenyl)propan-2-yl)carbamate

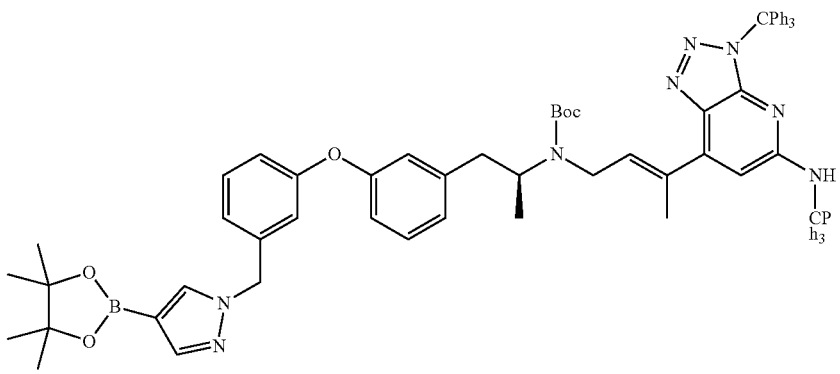

To a solution of 7E (75 mg, 0.17 mmol) in DMF (0.55 mL) was added cesium hydroxide monohydrate (58 mg, 0.35 mmol), and the mixture was stirred at rt for 30 min. KI (19 mg, 0.12 mmol) and Intermediate 2 (0.10 g, 0.12 mmol) were added, and stirring was continued for an additional 10 min. Boc$_2$O (0.54 mL, 0.23 mmol) was then added to the reaction mixture. The mixture was stirred for 1 h at room temperature. The solids were removed by filtration and washed with EtOAc. The filtrate was concentrated, and the residue purified by silica gel chromatography to give 7F (12 mg, 77%) MS(ESI) m/z 1317.6 (M+H).

7G. tert-Butyl (14Z,7S,10Z)-7-methyl-11-(3-trityl-5-(tritylamino)-3H-[1,2,3]triazolo[4,5-b]pyridin-7-yl)-11H-4-oxa-8-aza-1 (1,4)-pyrazola-3,5(1,3)-dibenzenacycloundecaphan-10-ene-8-carboxylate

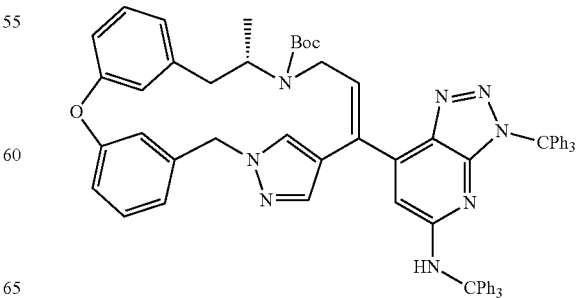

A mixture of 7F (0.12 g, 0.089 mmol), PdCl₂(dppf)-CH₂Cl₂ adduct (36 mg, 0.044 mmol) and K₂CO₃ (62 mg, 0.44 mmol) in a 100 mL flask was evacuated and back-filled with argon 3× times before sparged dioxane (60 mL) and H₂O (9.3 mL) were added. The resulting reaction mixture was stirred at 85° C. ON. The reaction mixture was filtered through Celite, and the solids were rinsed with EtOAc. The filtrate was concentrated. The crude was purified by flash chromatography to give 7G (34 mg, 36%) as a pale yellow oil. MS(ESI) m/z 1063.6 (M+H).

7H. 7-((14Z,7S,10Z)-7-Methyl-11H-4-oxa-8-aza-1(1,4)-pyrazola-3,5(1,3)-dibenzenacycloundecaphan-10-en-11-yl)-3H-[1,2,3]triazolo[4,5-b]pyridin-5-amine, TFA

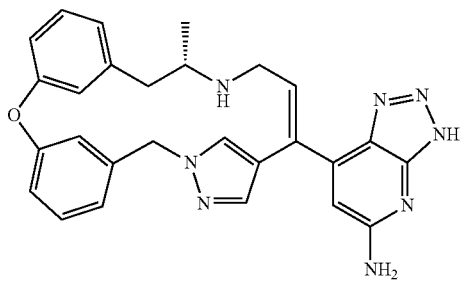 [SMILES: C[C@H]1Cc2cccc(c2)Oc2cccc(c2)Cn2cc(cn2)/C(c2cc(N)nc3[nH]nnc23)=C\CN1]

7G (34.1 mg, 0.032 mmol) was dissolved in DCM (3 mL) and TFA (0.3 mL), and the mixture was stirred at rt for 2-3 h. hours. A few drops of triethylsilane were added, and the mixture was concentrated. The residue was triturated with hexane to provide 7H (15 mg, 98%). MS(ESI) m/z 479.3 (M+H).

Example 7

7H (15 mg, 0.031 mmol) was dissolved in EtOH (0.5 mL), and PtO₂ (1.8 mg, 7.8 μmol) was added under Ar. The mixture was degassed, then stirred under 50 psi H₂ gas ON. The catalyst was removed by filtration, washed with EtOAc discarded. The filtrate was evaporated. Purification by RP-HPLC provided Example 7 (7.6 mg, 39%) MS(ESI) m/z 481.3 (M+H). ¹H NMR (500 MHz, CD₄OD) δ 7.78 (d, J=8.0 Hz, 1H), 7.53 (d, J=8.5 Hz, 1H), 7.46-7.37 (m, 2H), 7.24-7.05 (m, 3H), 7.00-6.90 (m, 1H), 6.82 (d, J=13.8 Hz, 1H), 6.56 (d, J=12.1 Hz, 1H), 6.04-5.79 (m, 1H), 5.35 (s, 2H), 4.49-4.37 (m, J=3.3 Hz, 1H), 3.86-3.74 (m, 1H), 3.17-3.05 (m, 1H), 2.92-2.76 (m, 2H), 2.62-2.37 (m, 3H), 1.50 (dd, J=10.0, 6.7 Hz, 3H). Analytical HPLC: RT=4.68 min (Method A).

Example 8

7-[(11R)-11-Methyl-18-oxa-3,4,10-triazatetracyclo[17.3.1.1³,⁶.1¹³,¹⁷]pentacosa-1(23),4,6(25),13,15,17(24),19,21-octaen-7-yl]-3H-[1,2,3]triazolo[4,5-b]pyridin-5-amine, 2TFA

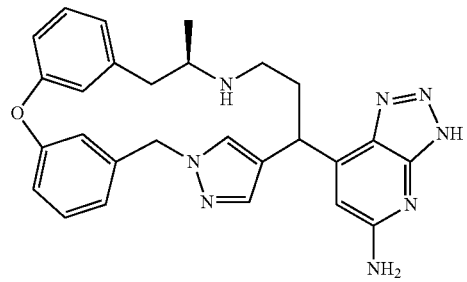 [SMILES: C[C@@H]1Cc2cccc(c2)Oc2cccc(c2)Cn2cc(cn2)C(c2cc(N)nc3[nH]nnc23)CCN1]

Example 8 was prepared as described for Example 7 by substituting (R)-2-methylpropane-2-sulfinamide for (S)-2-methylpropane-2-sulfinamide in step 7A. MS(ESI) m/z 481.2 (M+H). ¹H NMR (500 MHz, CD₄OD) δ 7.77 (d, J=8.5 Hz, 1H), 7.53 (d, J=8.3 Hz, 1H), 7.46-7.34 (m, 2H), 7.24-7.04 (m, 3H), 6.95 (ddd, J=17.6, 8.3, 2.2 Hz, 1H), 6.82 (d, J=14.0 Hz, 1H), 6.56 (d, J=12.4 Hz, 1H), 6.03-5.78 (m, 1H), 5.35 (s, 2H), 4.49-4.38 (m, 1H), 3.85-3.75 (m, 1H), 3.18-3.04 (m, 1H), 2.94-2.76 (m, 2H), 2.62-2.37 (m, 3H), 1.49 (dd, J=10.0, 6.7 Hz, 3H). Analytical HPLC: RT=4.74 min (Method A).

Example 9

7-{17-Oxa-3,4,10-triazatetracyclo[17.3.1.1³,⁶.1¹²,¹⁶]pentacosa-1(23),4,6(25),12,14,16(24),19,21-octaen-7-yl}-3H-[1,2,3]triazolo[4,5-b]pyridin-5-amine, 2TFA

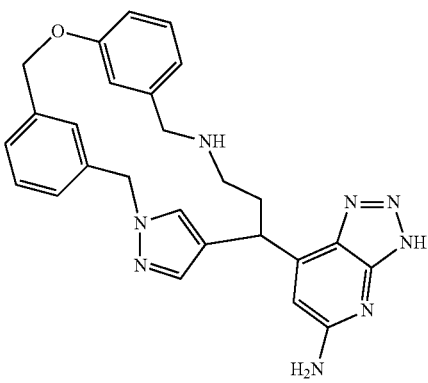 [SMILES: Nc1cc(C2CCNCc3cccc(c3)OCc3cccc(c3)Cn3cc2cn3)c2nn[nH]c2n1]

9A. (3-(((tert-Butyldiphenylsilyl)oxy)methyl)phenyl)methanol

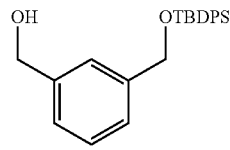

To a stirred solution of 1,3-phenylenedimethanol (1.0 g, 7.2 mmol) and imidazole (0.74 g, 11 mmol) in DMF (36 mL) at 0° C. was added TBDPS-Cl (2.0 mL, 7.6 mmol). After 30 min, the reaction mixture was allowed to warm to rt and stirred for 18 h. The mixture was diluted with Et$_2$O, washed with water (4×), then brine, dried over Na$_2$SO$_4$, filtered and concentrated. The crude product was purified by flash chromatography to give 9A (1.2 g, 44%). $^1$H NMR (500 MHz, CDCl$_3$) δ 7.72 (dd, J=8.0, 1.4 Hz, 4H), 7.45 (d, J=7.4 Hz, 2H), 7.43-7.37 (m, 4H), 7.34 (d, J=11.8 Hz, 3H), 7.29 (s, 2H), 4.81 (s, 2H), 4.71 (d, J=5.8 Hz, 2H), 1.59 (d, J=11.8 Hz, 1H), 1.13 (s, 9H).

9B. 1-(3-(((tert-Butyldiphenylsilyl)oxy)methyl)benzyl)-4-(4,4,5,5-tetramethyl-1,3,2-dioxaborolan-2-yl)-1H-pyrazole

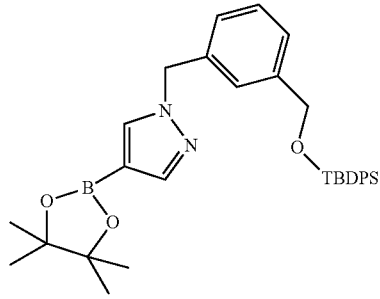

To a solution of 4-(4,4,5,5-tetramethyl-1,3,2-dioxaborolan-2-yl)-1H-pyrazole (0.62 g, 3.2 mmol) and 9A in toluene (16 mL) was added tri n-butylphosphine (1.3 mL, 5.1 mmol) and TMAD (0.89 g, 5.1 mmol), and the reaction mixture was stirred at rt for 18 h. The reaction was filtered, and the filtrate was concentrated. The crude product was purified by flash chromatography to give 9B (1.5 g, 84%). MS(ESI) m/z 553.3 (M+H).

9C. (3-((4-(4,4,5,5-Tetramethyl-1,3,2-dioxaborolan-2-yl)-1H-pyrazol-1-yl)methyl)phenyl)methanol

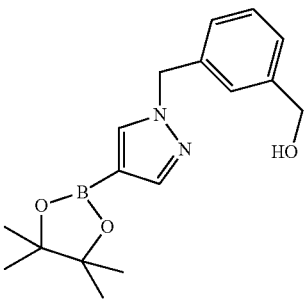 [SMILES: CC1(C)OB(c2cnn(Cc3cccc(CO)c3)c2)OC1(C)C]

To a solution of 9B (1.5 g, 2.7 mmol) in THF (24 mL) was added TBAF (4.0 mL, 4.0 mmol), and the reaction mixture was stirred for 3 h. The reaction was partitioned between EtOAc and water, and the phases were separated. The aqueous layer was extracted twice with EtOAc, and the combined organic layers were washed with brine, dried over Na$_2$SO$_4$, and concentrated. The crude product was purified by flash chromatography to give 9C (0.59 g, 70%). MS(ESI) m/z 314.9 (M+H).

9D. tert-Butyl 3-((3-((4-(4,4,5,5-tetramethyl-1,3,2-dioxaborolan-2-yl)-1H-pyrazol-1-yl)methyl)benzyl)oxy)benzylcarbamate

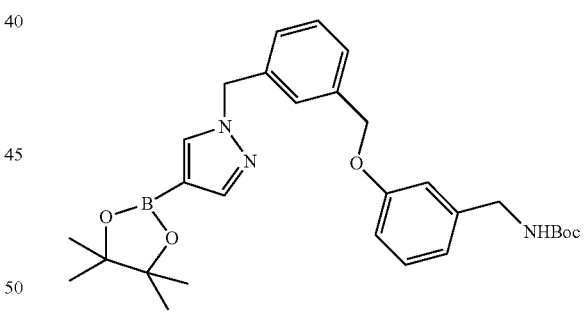

To a solution of 9C (0.22 g, 0.69 mmol) and tert-butyl 3-hydroxybenzylcarbamate (0.18 g, 0.81 mmol) in THF (2.2 mL) at 0° C. was added Ph$_3$P (0.22 g, 0.83 mmol) and DIAD (0.16 mL, 0.83 mmol). The mixture was gradually warmed to rt and stirred for 18 h. Additional portions of DIAD (0.08 mL, 0.41 mmol) and Ph$_3$P (0.11 g, 0.41 mmol) were added, and the mixture was stirred for an additional 18 h. The reaction mixture was concentrated, and the crude product was purified by flash chromatography to give 9D (199 mg, 56%). MS(ESI) m/z 520.2 (M+H).

9E. (3-((3-((4-(4,4,5,5-Tetramethyl-1,3,2-dioxaborolan-2-yl)-1H-pyrazol-1-yl)methyl)benzyl)oxy)phenyl)methanamine, HCl

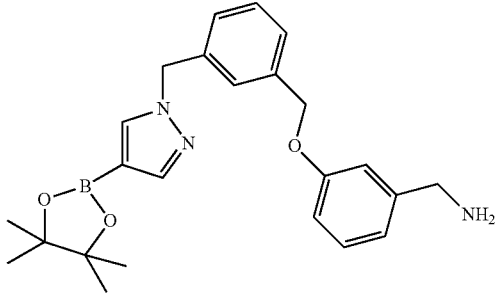 [SMILES: CC1(C)OB(c2cnn(Cc3cccc(COc4cccc(CN)c4)c3)c2)OC1(C)C]

To a solution of 9D (199 mg, 0.383 mmol) in dioxane (3 mL) was added HCl (0.957 mL, 3.83 mmol; 4N in dioxane). The reaction mixture was stirred at rt. After reaction was complete by LCMS, the volatiles were removed by evaporated, and the residue was triturated with Et$_2$O to provide 9E as a white solid (114 mg, 70.8%). MS(ESI) m/z 420.1 (M+H).

Example 9 was prepared from 9E using the procedures described for the preparation of Example 7 starting from step 7F. MS(ESI) m/z 467.3 (M+H). $^1$H NMR (500 MHz, CD$_4$OD) δ 7.68 (s, 1H), 7.45 (d, J=0.6 Hz, 1H), 7.41-7.30 (m, 3H), 7.26-7.20 (m, 1H), 6.99-6.96 (m, 2H), 6.94 (d, J=7.7 Hz, 1H), 6.88 (dd, J=8.0, 2.2 Hz, 1H), 6.59 (s, 1H), 5.32 (s, 2H), 5.30-5.19 (m, 2H), 4.50 (d, J=9.1 Hz, 1H), 4.29 (d, J=13.2 Hz, 1H), 4.08 (d, J=13.2 Hz, 1H), 2.98-2.88 (m, 1H), 2.71-2.61 (m, 1H), 2.57-2.38 (m, 2H). Analytical HPLC: RT=4.09 min (Method A).

Example 10

7-[(17R)-17-Methyl-18-oxa-3,4,10-triazatetracyclo[17.3.1.1$^{3,6}$.1$^{12,16}$]pentacosa-1(23),4,6(25),12,14,16(24),19,21-octaen-7-yl]-3H-[1,2,3]triazolo[4,5-b]pyridin-5-amine, 2TFA

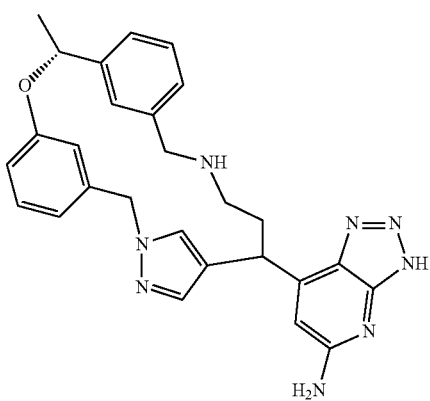 [SMILES: C[C@H]1Oc2cccc(c2)Cn2cc(cn2)C(c2cc(N)nc3[nH]nnc23)CCNCc2cccc1c2]

10A. (S)-3-(1-Hydroxyethyl)benzonitrile

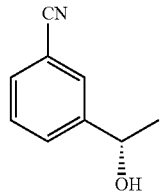

A solution of 3-acetylbenzonitrile (0.50 g, 3.4 mmol) in THF (10 mL) was added to a solution of 1M BH$_3$-THF (2.1 mL, 2.1 mmol) and (S)-1-methyl-3,3-diphenylhexahydropyrrolo[1,2-c][1,3,2]oxazaborole (95 mg, 0.34 mmol) in THF (8 mL) at −78° C. dropwise over 20 min. The resulting solution was allowed to gradually warm to rt and stir for 18 h. The reaction mixture was quenched with MeOH (0.2 mL), then water (1 mL). The mixture was stirred for 30 min, then diluted with EtOAc, washed with water and brine, then dried over Na$_2$SO$_4$, filtered and concentrated. The crude product was purified by flash chromatography to give 10A (420 mg, 83%, 75.2% ee). $^1$H NMR (500 MHz, CDCl$_3$) δ 7.70 (s, 1H), 7.62 (d, J=8.0 Hz, 1H), 7.57 (d, J=7.7 Hz, 1H), 7.49-7.44 (m, 1H), 4.96 (s, 1H), 1.92 (d, J=3.9 Hz, 1H), 1.52 (d, J=7.2 Hz, 2H).

10B. (S)-tert-Butyl 3-(1-hydroxyethyl)benzylcarbamate

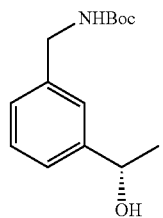 [SMILES: C[C@H](O)c1cccc(CNC(=O)OC(C)(C)C)c1]

To a solution of 10A (0.42 g, 2.9 mmol) in THF (3.0 mL) was added a 1M solution of LiAlH$_4$ in THF (5.7 mL, 5.7 mmol) at 0° C. dropwise. The reaction was allowed to gradually warm to rt and stirred for 18 h. The reaction mixture was diluted with 15 mL of THF, then quenched at 0° C. sequentially with H$_2$O (0.2 mL), 1N NaOH (0.2 mL) and H$_2$O (0.6 mL). After stirring for 15 min at rt, MeOH (5.0 mL) was added, followed by Boc$_2$O (0.62 g, 2.9 mmol). After stirring for an additional 1 h at rt, the suspension was filtered, and the solids washed with EtOAc. The filtrate was concentrated, and the crude product purified by flash chromatography to give 10B (0.52 g, 72%). $^1$H NMR (500 MHz, CDCl$_3$) δ 7.36-7.27 (m, 3H), 7.21 (d, J=7.2 Hz, 1H), 4.91 (dd, J=6.3, 3.6 Hz, 1H), 4.33 (d, J=5.2 Hz, 2H), 1.80 (d, J=3.6 Hz, 1H), 1.50 (d, J=6.3 Hz, 3H), 1.48 (s, 9H).

10C. (R)-methyl 3-(1-(3-(((tert-butoxycarbonyl) amino)methyl)phenyl)ethoxy)benzoate

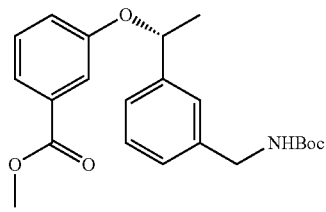 [SMILES: COC(=O)c1cccc(O[C@H](C)c2cccc(CNC(=O)OC(C)(C)C)c2)c1]

10C was prepared from 10B using the procedure described for 9D. MS(ESI) m/z 387.1 (M+H).

10D. (R)-tert-Butyl 3-(1-(3-(hydroxymethyl)phenoxy)ethyl)benzylcarbamate

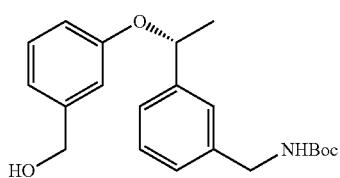 [SMILES: C[C@@H](Oc1cccc(CO)c1)c1cccc(CNC(=O)OC(C)(C)C)c1]

To a solution of 10C (0.55 g, 1.4 mmol) in THF (2.9 mL) was added a 2M solution of LiBH$_4$ in THF (1.4 mL, 2.9 mmol) in rapid dropwise fashion, followed by MeOH (0.12 mL, 2.9 mmol). The reaction mixture was stirred at room temperature for 1 h, and then was heated to 66° C. for 4.5 h. The reaction mixture was cooled in an ice bath and quenched with water, then 1M NaOH. EtOAc was added, and mixture was stirred to dissolve the solids. The layers were separated, and the aqueous layer was extracted with EtOAc. The combined organic layers were washed with brine, dried over Na$_2$SO$_4$ and concentrated. The crude product was purified by flash chromatography, followed by purification by chiral SFC (Chiralcel OJ column, 30×250 mm, 5 micron; mobile phase: 30% MeOH/70% CO$_2$; flow conditions: 85 mL/min, 150 Bar, 40° C.) to resolve the enriched stereoisomers to give 10D (192 mg, 32%, 99.0% ee). MS(ESI) m/z 358.1 (M+H).

Example 10 was prepared from 10D using the procedures described for the preparation of Example 9 from 9E. MS(ESI) m/z 481.3 (M+H). $^1$H NMR (500 MHz, CD$_4$OD) δ 7.64 (d, J=9.9 Hz, 1H), 7.45-7.38 (m, 3H), 7.37-7.32 (m, 2H), 7.29 (dt, J=9.6, 8.0 Hz, 1H), 7.04 (ddd, J=7.7, 5.1, 2.1 Hz, 1H), 6.98 (t, J=6.7 Hz, 1H), 6.63 (d, J=11.0 Hz, 1H), 6.36-6.22 (m, 1H), 5.42-5.31 (m, 1H), 5.30-5.12 (m, 2H), 4.58 (dd, J=12.5, 3.2 Hz, 1H), 4.36 (dd, J=13.5, 12.4 Hz, 1H), 4.17 (dd, J=13.3, 9.5 Hz, 1H), 3.03-2.91 (m, 1H), 2.77-2.35 (m, 3H), 1.60 (dd, J=9.5, 6.5 Hz, 3H). Analytical HPLC: RT=4.92 min (Method A).

Example 11

[(11S)-7-{5-Amino-3H-[1,2,3]triazolo[4,5-b]pyridin-7-yl}-18-oxa-3,4,10-triazatetracyclo[17.3.1.1$^{3,6}$.1$^{13,17}$]pentacosa-1(23),4,6(25),13,15,17(24),19,21-octaen-11-yl]methanol, 2TFA

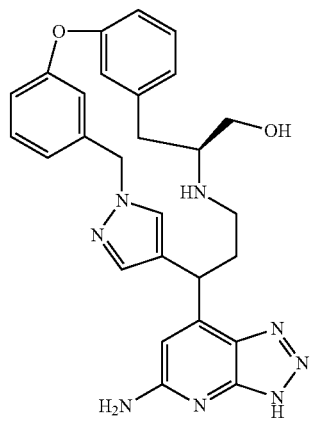 [SMILES: Nc1cc(C2CCN[C@H](CO)Cc3cccc(c3)Oc3cccc(c3)Cn3cc2cn3)c2nn[nH]c2n1]

11A. (S)-tert-Butyl (1-hydroxy-3-(3-iodophenyl)propan-2-yl)carbamate

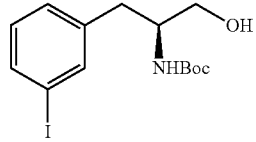 [SMILES: CC(C)(C)OC(=O)N[C@H](CO)Cc1cccc(I)c1]

To a solution of (S)-2-((tert-butoxycarbonyl)amino)-3-(3-iodophenyl)propanoic acid (1.0 g, 2.6 mmol) in THF (13 mL) at −78° C. was added 1M BH$_3$-THF (5.1 mL, 5.1 mmol) dropwise. The solution was allowed to warm to rt and stirred for 18 h. The reaction mixture was cooled to 0° C. and quenched with 10% AcOH in MeOH (30 mL). After stirring at 0° C. for 10 min, the mixture was concentrated in vacuo. The residue was dissolved in EtOAc and washed with 1N HCl, water, and saturated aq. NaHCO$_3$. The organic layer was dried over Na$_2$SO$_4$, filtered and concentrated to give 11A (0.53 g, 55%). $^1$H NMR (500 MHz, CDCl$_3$) δ 7.59 (s, 2H), 7.24-7.15 (m, 1H), 7.11-7.00 (m, 1H), 4.78-4.64 (m, 1H), 3.89-3.79 (m, 1H), 3.71-3.63 (m, 1H), 3.61-3.53 (m, 1H), 2.83-2.76 (m, 2H), 1.44 (s, 9H)

11B. (S)-tert-Butyl (1-((tert-butyldiphenylsily)oxy)-3-(3-iodophenyl)propan-2-yl)carbamate

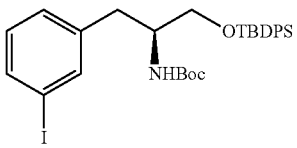

Example 11B was prepared using the procedure described for 9A. (733 mg, 51%) MS(ESI) m/z 616.2 (M+H).

11C. tert-Butyl (14Z,7S,10Z)-7-((((tert-butyldiphenylsilyl)oxy)methyl)-11-(3-trityl-5-(tritylamino)-3H-[1,2,3]triazolo[4,5-b]pyridin-7-yl)-11H-4-oxa-8-aza-1(1,4)-pyrazola-3,5(1,3)-dibenzenacycloundecaphan-10-ene-8-carboxylate

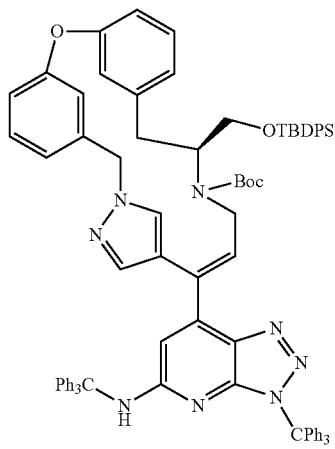

11C was prepared from 11B following the steps described for the conversion of 7A to 7G. MS(ESI) m/z 1317.1 (M+H).

11D. tert-Butyl (14Z,7S,10Z)-7-(hydroxymethyl)-11-(3-trityl-5-(tritylamino)-3H-[1,2,3]triazolo[4,5-b]pyridin-7-yl)-11H-4-oxa-8-aza-1(1,4)-pyrazola-3,5(1,3)-dibenzenacycloundecaphan-10-ene-8-carboxylate

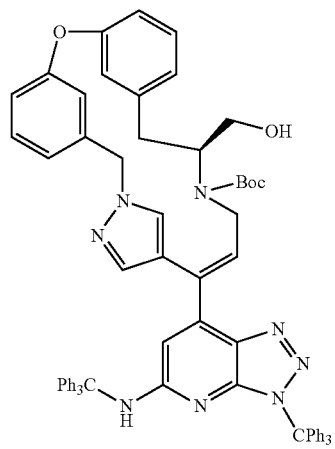

11C (35 mg, 0.027 mmol) was taken up in THF (0.9 mL) and TBAF (0.08 mL, 0.08 mmol) was added. The reaction mixture was stirred at rt ON. The reaction mixture was concentrated, and the residue purified by flash chromatography to provide 11D which was used directly in the next step.

Example 11 was prepared from 11D using the procedures described for 7H and Ex. 7. MS(ESI) m/z 497.3 (M+H). $^1$H NMR (500 MHz, CD$_4$OD) δ 7.74 (d, J=6.6 Hz, 1H), 7.53 (d, J=2.2 Hz, 1H), 7.45-7.37 (m, 2H), 7.23-7.05 (m, 3H), 6.99-6.92 (m, 1H), 6.86 (d, J=15.1 Hz, 1H), 6.42 (d, J=11.6 Hz, 1H), 6.05-5.78 (m, 1H), 5.37-5.34 (m, 2H), 4.47-4.37 (m, 1H), 3.98-3.86 (m, 1H), 3.73 (dd, J=11.7, 5.6 Hz, 1H), 3.69-3.60 (m, 1H), 3.15-3.06 (m, 1H), 2.96-2.83 (m, 2H), 2.64-2.39 (m, 3H). Analytical HPLC: RT=4.28 min (Method A).

Example 12

7-{14-Fluoro-17-oxa-3,4,10-triazatetracyclo[17.3.1.1$^{3,6}$.1$^{12,16}$]pentacosa-1(23),4,6(25),12(24),13,15,19,21-octaen-7-yl}-3H-[1,2,3]triazolo[4,5-b]pyridin-5-amine

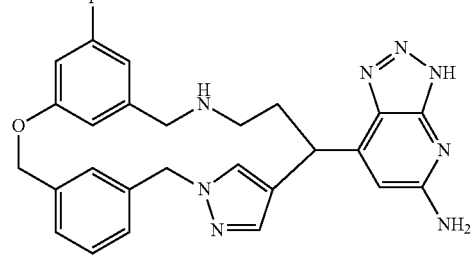

Example 12 was prepared from 9C and tert-butyl 3-fluoro-5-hydroxybenzylcarbamate (prepared from 3-fluoro-5-hydroxybenzonitrile by procedures described for 10B) using procedures described for Example 9. MS(ESI) m/z 485.2 (M+H). $^1$H NMR (500 MHz, CD$_4$OD) δ 7.70 (s, 1H), 7.49 (s, 1H), 7.46-7.32 (m, 3H), 6.99 (s, 1H), 6.84 (s, 1H), 6.74 (d, J=6.9 Hz, 1H), 6.68 (dt, J=10.9, 2.1 Hz, 1H), 6.50 (s, 1H), 5.34 (s, 2H), 5.27 (q, J=15.4 Hz, 2H), 4.50 (dd, J=12.0, 3.4 Hz, 1H), 4.30 (d, J=13.2 Hz, 1H), 4.10 (d, J=13.2 Hz, 1H), 3.03-2.89 (m, 1H), 2.72-2.62 (m, 1H), 2.58-2.38 (m, 2H). Analytical HPLC: RT=4.53 min (Method A).

Example 13

7-{15-Methoxy-17-oxa-3,4,10-triazatetracyclo[17.3.1.1$^{3,6}$.1$^{12,16}$]pentacosa-1(23),4,6(25),12(24),13,15,19,21-octaen-7-yl}-3H-[1,2,3]triazolo[4,5-b]pyridin-5-amine, 2TFA

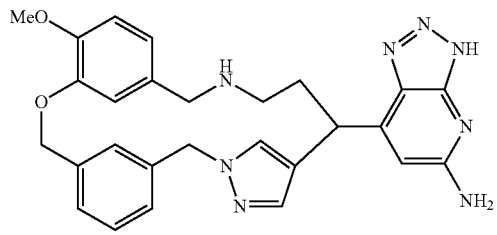 [SMILES: COc1ccc2cc1OCc1cccc(c1)Cn1cc(cn1)C(c1cc(N)nc3[nH]nnc13)CCNC2]

Example 13A. tert-butyl 3-hydroxy-4-methoxybenzylcarbamate

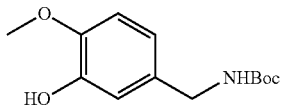 [SMILES: COc1ccc(CNC(=O)OC(C)(C)C)cc1O]

To a solution of 5-(aminomethyl)-2-methoxyphenol, HCl (1.1 g, 5.6 mmol) and Boc$_2$O (2.4 g, 11 mmol) in MeOH (28 mL) was added NaHCO$_3$(1.9 g, 22 mmol), and the reaction mixture was stirred at rt for 18 h. The mixture was filtered, and the filtrate was concentrated. The residue was purified by flash chromatography to give 13A (0.33 g, 23%). MS(ESI) m/z 254.0 (M+H).

13B. tert-Butyl 3-((3-(hydroxymethyl)benzyl)oxy)-4-methoxybenzylcarbamate

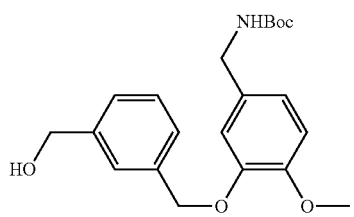 [SMILES: COc1ccc(CNC(=O)OC(C)(C)C)cc1OCc1cccc(CO)c1]

13B was prepared from 13A and 1,3-phenylenedimethanol by Mitsunobu alkylation using the procedure described for 10D. MS(ESI) m/z 374.3 (M+H).

Example 13 was prepared from 13B using the procedures described for the preparation of Example 9 from 9D. MS(ESI) m/z 497.3 (M+H). $^1$H NMR (500 MHz, CD$_4$OD) δ 7.59 (s, 1H), 7.46 (s, 1H), 7.44-7.36 (m, 3H), 7.03 (d, J=0.8 Hz, 2H), 6.91 (d, J=11.3 Hz, 2H), 6.53 (s, 1H), 5.32-5.24 (m, 4H), 4.48 (dd, J=11.7, 3.7 Hz, 1H), 4.14 (d, J=13.2 Hz, 1H), 4.02 (d, J=13.5 Hz, 1H), 3.86-3.83 (m, 3H), 2.88-2.80 (m, 1H), 2.69-2.61 (m, 1H), 2.52-2.41 (m, 2H). Analytical HPLC: RT=4.03 min (Method A).

Example 14

7-{15-Fluoro-17-oxa-3,4,10-triazatetracyclo [17.3.1.1$^{3,6}$.1$^{12,16}$]pentacosa-1(23),4,6(25),12(24), 13,15,19,21-octaen-7-yl}-3H-[1,2,3]triazolo[4,5-b] pyridin-5-amine, 2TFA

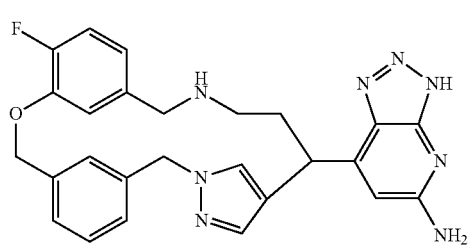 [SMILES: Nc1cc(C2CCNCc3ccc(F)c(c3)OCc3cccc(c3)Cn3cc2cn3)c2nn[nH]c2n1]

Example 14 was prepared from 9C and tert-butyl 4-fluoro-3-hydroxybenzylcarbamate (prepared from 4-fluoro-3-hydroxybenzonitrile by procedures described for 10B) using the procedures described for Example 9. MS(ESI) m/z 485.3 (M+H). $^1$H NMR (500 MHz, CD$_4$OD) δ 7.62 (s, 1H), 7.45 (s, 1H), 7.44-7.37 (m, 3H), 7.15 (dd, J=11.0, 8.5 Hz, 1H), 7.10 (dd, J=7.8, 2.1 Hz, 1H), 7.02 (ddd, J=8.5, 4.1, 2.1 Hz, 1H), 6.92 (s, 1H), 6.56 (s, 1H), 5.31 (s, 2H), 5.30-5.24 (m, 2H), 4.49 (dd, J=12.0, 3.7 Hz, 1H), 4.20 (d, J=13.5 Hz, 1H), 4.05 (d, J=13.2 Hz, 1H), 2.90-2.81 (m, 1H), 2.64 (d, J=5.0 Hz, 1H), 2.54-2.41 (m, 2H). Analytical HPLC: RT=4.53 min (Method A).

Example 15

7-{14-Chloro-17-oxa-3,4,10-triazatetracyclo [17.3.1.1$^{3,6}$.1$^{12,16}$]pentacosa-1(23),4,6(25),12(24), 13,15,19,21-octaen-7-yl}-3H-[1,2,3]triazolo[4,5-b] pyridin-5-amine, 2TFA

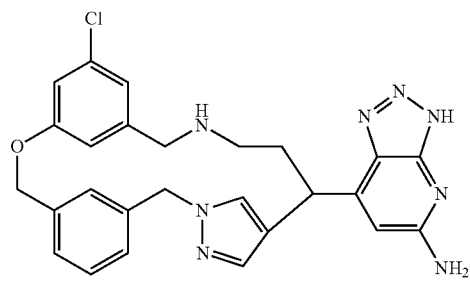 [SMILES: Nc1cc(C2CCNCc3cc(Cl)cc(c3)OCc3cccc(c3)Cn3cc2cn3)c2nn[nH]c2n1]

Example 15 was prepared from 1,3-phenylenedimethanol and tert-butyl 3-chloro-5-hydroxybenzylcarbamate (prepared from 3-chloro-5-hydroxybenzonitrile by procedures described for 10B) using the procedures described for Example 13. MS(ESI) m/z 501.1 (M+H). $^1$H NMR (500 MHz, CD$_4$OD) δ 7.68 (s, 1H), 7.49 (s, 1H), 7.44-7.32 (m, 3H), 7.07-6.88 (m, 4H), 6.37 (br. s., 1H), 5.39-5.21 (m, 4H), 4.47 (d, J=9.1 Hz, 1H), 4.28 (d, J=13.2 Hz, 1H), 4.10 (d, J=13.2 Hz, 1H), 3.00-2.88 (m, 1H), 2.67 (d, J=9.9 Hz, 1H), 2.54-2.38 (m, 2H). Analytical HPLC: RT=4.67 min (Method A).

Example 16

7-{18-Oxa-3,4,10-triazatetracyclo[18.3.1.1$^{3,6}$.1$^{13,17}$] hexacosa-1(24),4,6(26),13(25),14,16,20,22-octaen-7-yl}-3H-[1,2,3]triazolo[4,5-b]pyridin-5-amine, 2 TFA

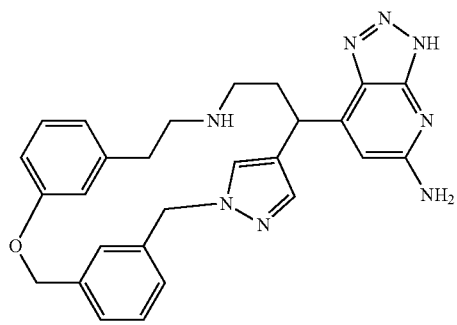 [SMILES: Nc1cc(C2CCNCCc3cccc(c3)OCc3cccc(c3)Cn3cc2cn3)c2nn[nH]c2n1]

Example 16 was prepared from 1,3-phenylenedimethanol and 3-(2-aminoethyl)phenol hydrochloride, using the procedures described for Example 13. MS(ESI) m/z 481.3 (M+H). ¹H NMR (500 MHz, CD₄OD) δ 7.65 (s, 1H), 7.55 (d, J=0.6 Hz, 1H), 7.42-7.32 (m, 3H), 7.22 (t, J=8.0 Hz, 1H), 7.16 (s, 1H), 6.86 (d, J=7.7 Hz, 1H), 6.81 (dd, J=8.3, 2.2 Hz, 1H), 6.71 (d, J=1.9 Hz, 1H), 6.60 (s, 1H), 5.36-5.18 (m, 4H), 4.43 (dd, J=9.8, 5.4 Hz, 1H), 3.39-3.34 (m, 1H), 3.30-3.23 (m, 1H), 2.99-2.85 (m, 3H), 2.71-2.60 (m, 1H), 2.53-2.36 (m, 2H). Analytical HPLC: RT=4.61 min (Method A).

Example 17

7-{14-Oxa-3,4,10-triazatricyclo[13.3.1.1³,⁶]icosa-1(19),4,6(20),15,17-pentaen-7-yl}-3H-[1,2,3]triazolo[4,5-b]pyridin-5-amine, 2TFA

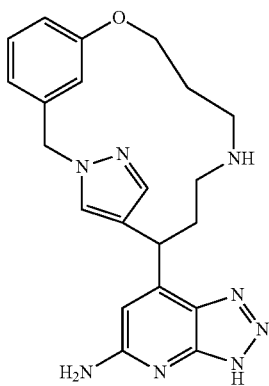 [SMILES: Nc1cc(C2CCNCCCOc3cccc(c3)Cn3cc2cn3)c2nn[nH]c2n1]

17A. Methyl 3-(3-((tert-butoxycarbonyl)amino)propoxy)benzoate

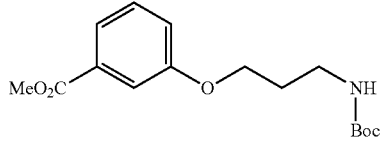 [SMILES: COC(=O)c1cccc(OCCCNC(=O)OC(C)(C)C)c1]

tert-Butyl (3-hydroxypropyl)carbamate (1.38 g, 7.89 mmol) and methyl 3-hydroxybenzoate (1.00 g, 6.57 mmol) were dissolved in THF (13.2 mL). Triphenylphosphine (2.07 g, 7.89 mmol) was added, and the mixture was stirred under argon and cooled to 0° C. DIAD (1.53 mL, 7.89 mmol) was added dropwise. The reaction was stirred ON, allowing the reaction to gradually assume rt. The reaction mixture was evaporated, and the crude product was purified by flash chromatography to provide 17A (1.91 g, 94%) as a colorless oil. MS(ESI) m/z 310.1 (M+H).

17B. tert-Butyl (3-(3-(hydroxymethyl)phenoxy)propyl)carbamate

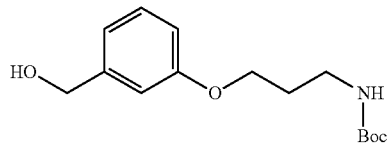 [SMILES: CC(C)(C)OC(=O)NCCCOc1cccc(CO)c1]

17A (1.91 g, 6.17 mmol) was dissolved in THF (12.4 mL) with stirring under argon. The solution was cooled to 0° C., and a solution of lithium borohydride, 2M in THF (6.17 mL, 12.4 mmol) was added in rapid dropwise fashion. MeOH (0.500 mL, 12.5 mmol) was then added slowly dropwise. The reaction mixture was stirred ON allowing the reaction to gradually assume rt. The reaction mixture was cooled in an ice bath and quenched with water, then 1M NaOH. EtOAc was added, and mixture was stirred to dissolve the solids. The mixture was transferred to a separatory funnel with additional water to help dissolve the remaining white solid. The phases were separated, and aq. layer was reextracted 2× with EtOAc. The combined extracts were washed with water and brine, then dried over Na₂SO₄, filtered and evaporated to provide 17B as a viscous oil (1.69 g, 97%). MS(ESI) m/z 281.9 (M+H).

17C. tert-Butyl (3-(3-((4-iodo-1H-pyrazol-1-yl)methyl)phenoxy)propyl)carbamate

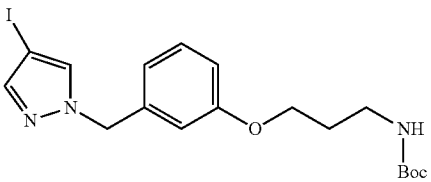 [SMILES: CC(C)(C)OC(=O)NCCCOc1cccc(Cn2cc(I)cn2)c1]

17B (1.7 g, 6.0 mmol) and 4-iodo-1H-pyrazole (0.97 g, 5.0 mmol) were dissolved in THF (10 mL). Triphenylphosphine (1.6 g, 6.0 mmol) was added, and the solution was stirred under argon and cooled to 0° C. DIAD (1.2 mL, 6.0 mmol) was added dropwise. The reaction mixture was stirred ON allowing reaction to gradually assume rt. The reaction mixture was evaporated, and the residue was purified by flash chromatography to give 17C (2.4 g, 105% yield) as a white solid. MS(ESI) m/z 458.0 (M+H).

17D. tert-Butyl(3-(3-((4-(4,4,5,5-tetramethyl-1,3,2-dioxaborolan-2-yl)-1H-pyrazol-1-yl)methyl)phenoxy)propyl)carbamate

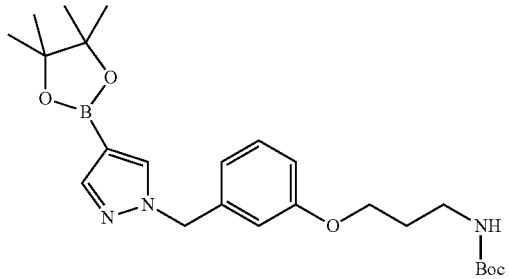 [SMILES: CC(C)(C)OC(=O)NCCCOc1cccc(Cn2cc(B3OC(C)(C)C(C)(C)O3)cn2)c1]

17C (0.50 g, 0.82 mmol), 4,4,4',4',5,5,5',5'-octamethyl-2,2'-bi(1,3,2-dioxaborolane) (0.31 g, 1.2 mmol), KOAc (0.24 g, 2.5 mmol) and DPPF (46 mg, 0.082 mmol) and DMF (0.27 mL) were added to a pressure-rated vial. The vial was evacuated and back-filled with argon three times. The reaction mixture was then stirred at 85° C. ON. The reaction mixture was filtered, and the filtrate was concentrated. The residue was diluted with water, and the solids were filtered off. The filtrate was then extracted with ethyl acetate (3×). The combined organic layers were washed with brine, dried over $Na_2SO_4$, filtered and concentrated. The residue was purified by flash chromatography to provide 17D (0.24 g, 64.5%) containing some des-iodo starting material as by-product MS(ESI) m/z 458.0 (M+H). This was used in the next step without further purification.

17E. 3-(3-((4-(4,4,5,5-Tetramethyl-1,3,2-dioxaborolan-2-yl)-1H-pyrazol-1-yl)methyl)phenoxy)propan-1-amine

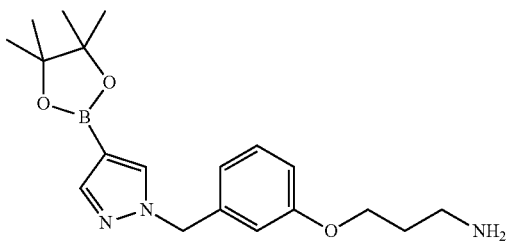 [SMILES: CC1(C)OB(c2cnn(Cc3cccc(OCCCN)c3)c2)OC1(C)C]

To a solution of 17D (130 mg, 0.28 mmol) in dioxane (1 mL) was added a solution of 4M HCl in dioxane (0.70 mL, 2.8 mmol). The reaction mixture was stirred at rt for 1 h, then evaporated to remove solvents. The residual solid was dissolved in DCM and washed with saturated aq. $NaHCO_3$. The aqueous layer was extracted with DCM (3×), and the combined organics were concentrated to give 17E (65 mg, 64.5%) as a colorless oil. MS(ESI) m/z 358.0 (M+H).

17F. (Z)-tert-Butyl (3-iodo-3-(3-trityl-5-(tritylamino)-3H-[1,2,3]triazolo[4,5-b]pyridin-7-yl)allyl) (3-(3-((4-(4,4,5,5-tetramethyl-1,3,2-dioxaborolan-2-yl)-1H-pyrazol-1-yl)methyl)phenoxy)propyl)carbamate

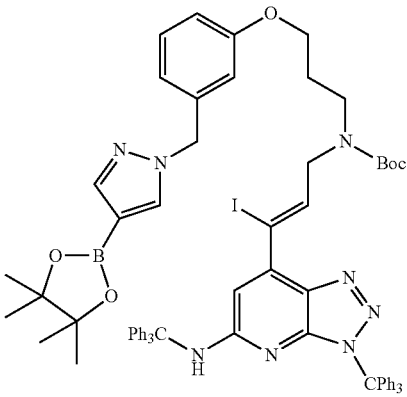

To 17E (22 mg, 0.062 mmol) in DMF (0.26 mL) was added activated 4 Å molecular sieves (45 mg) and cesium hydroxide monohydrate (8.7 mg, 0.052 mmol). The mixture was stirred at rt for 30 min. Intermediate 2 (45 mg, 0.052 mmol) was then added, and stirring was continued for an additional 10 min. $Boc_2O$ (27 mg) was added to the reaction mixture. Stirring was continued for an additional 15 min, and another portion of $Boc_2O$ (10 mg) was added. The reaction mixture was then stirred for 1 h at rt. The solids were removed by filtration and washed 2× with EtOAc. The filtrate was concentrated, and the residue was purified on a silica gel column pre-treated with 1% TEA/Hex to give 17E (69 mg, 49%).

17F. tert-Butyl (14Z,10Z)-11-(3-trityl-5-(tritylamino)-3H-[1,2,3]triazolo[4,5-b]pyridin-7-yl)-11H-4-oxa-8-aza-1(1,4)-pyrazola-3(1,3)-benzenacycloundecaphan-10-ene-8-carboxylate

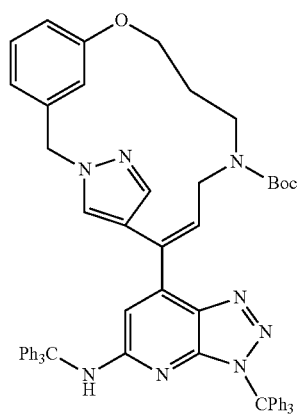

A mixture of 17E (69 mg, 0.060 mmol), $PdCl_2(dppf)$-$CH_2Cl_2$ adduct (49 mg, 0.060 mmol) and $K_2CO_3$ (82 mg, 0.60 mmol) was evacuated and back-filled with argon 3× before sparged dioxane (50 mL) and $H_2O$ (7.7 mL) were added. The resulting reaction mixture was stirred at 85° C.

ON. The reaction mixture was filtered through Celite, and the solids rinsed with EtOAc. The filtrate was concentrated. The crude was purified by flash chromatography to give 17F (23 mg, 39.1%) as a pale yellow oil. MS(ESI) m/z 987.6 (M+H).

Example 17

TFA (0.58 mL) was added to a solution of 17F (23 mg, 0.023 mmol) in DCM (1.75 mL) to produce a bright yellow solution which was stirred for 1 h at rt.

Triethylsilane (37 μL, 0.23 mmol) was then added, and the reaction mixture was concentrated. The residue was dissolved in EtOH (1 mL) and added to $PtO_2$ (1.3 mg, 5.8 μmol), and the mixture was stirred under 30 psi $H_2$ gas for 48 h. The catalyst was removed by filtration, and the filtrate was concentrated. The product was purified by RP-HPLC to give the title compound (6.8 mg, 46% yield). MS(ESI) m/z 405.2 (M+H). $^1$H NMR (500 MHz, $CD_4OD$) δ 8.28-8.09 (m, 1H), 7.62 (s, 1H), 7.39-7.19 (m, 1H), 7.03 (d, J=7.7 Hz, 1H), 6.84 (dd, J=8.3, 1.9 Hz, 1H), 6.79 (s, 1H), 6.34 (s, 1H), 5.49-5.30 (m, 2H), 4.51 (dd, J=12.4, 2.8 Hz, 1H), 4.31-4.09 (m, 2H), 3.29-3.22 (m, 1H), 3.19-3.03 (m, 2H), 2.81 (td, J=12.1, 3.0 Hz, 1H), 2.65 (tdd, J=12.0, 6.7, 3.0 Hz, 1H), 2.58-2.47 (m, 1H), 2.01-1.87 (m, 1H), 1.85-1.74 (m, 1H). Analytical HPLC: RT=3.25 min (Method A).

Examples 18-22 were similarly prepared using the procedures described for Example 17 and the indicated aminoalcohols.

Example 18

7-{3-Oxa-10,11,17-triazatetracyclo[16.2.2.1$^{4,8}$.1$^{10,13}$]tetracosa-4,6,8(24),11,13(23)-pentaen-14-yl}-3H-[1,2,3]triazolo[4,5-b]pyridin-5-amine, 2TFA

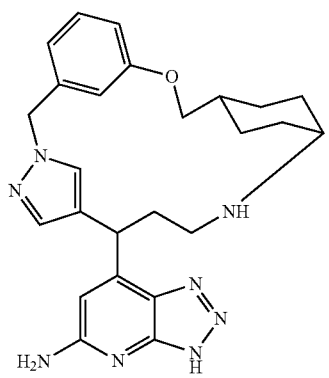 [SMILES: Nc1cc(C2CCNC3CCC(CC3)COc3cccc(c3)Cn3cc2cn3)c2nn[nH]c2n1]

(Prepared from tert-butyl (cis-4-(hydroxymethyl)cyclohexyl)carbamate) MS(ESI) m/z 459.2 (M+H). $^1$H NMR (500 MHz, $CD_3OD$) δ 7.96 (s, 1H), 7.80 (s, 1H), 7.30 (t, J=8.0 Hz, 1H), 6.96 (d, J=7.7 Hz, 1H), 6.79 (dd, J=8.3, 2.2 Hz, 1H), 6.70 (s, 1H), 5.72 (s, 1H), 5.50-5.34 (m, 2H), 4.72-4.63 (m, 1H), 4.19-4.12 (m, 1H), 4.12-4.05 (m, 1H), 3.49-3.39 (m, 1H), 3.20-3.07 (m, 1H), 2.93-2.82 (m, 1H), 2.68-2.54 (m, 2H), 2.11-2.00 (m, 2H), 1.99-1.90 (m, 3H), 1.83-1.74 (m, 2H), 1.73-1.61 (m, 2H). Analytical HPLC: RT=4.16 min (Method A).

Example 19

7-{14'-Oxa-3',4',10'-triazaspiro[cyclopropane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 2TFA

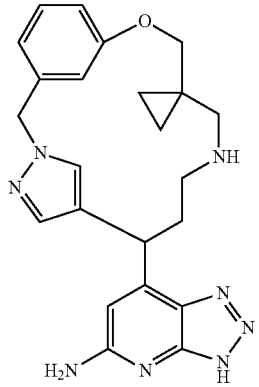 [SMILES: Nc1cc(C2CCNCC3(CC3)COc3cccc(c3)Cn3cc2cn3)c2nn[nH]c2n1]

(Prepared from tert-butyl ((1-(hydroxymethyl)cyclopropyl)methyl)carbamate) MS(ESI) m/z 431.1 (M+H). $^1$H NMR (500 MHz, $CD_3OD$) δ 7.96 (s, 1H), 7.80 (s, 1H), 7.30 (t, J=8.0 Hz, 1H), 6.96 (d, J=7.7 Hz, 1H), 6.79 (dd, J=88.14 (s, 1H), 7.69 (s, 1H), 7.28 (t, J=7.8 Hz, 1H), 7.01 (d, J=7.4 Hz, 1H), 6.87 (s, 1H), 6.81 (dd, J=8.3, 2.2 Hz, 1H), 5.96 (s, 1H), 5.54-5.35 (m, 2H), 4.55 (dd, J=12.4, 2.8 Hz, 1H), 4.18-3.98 (m, 2H), 3.29-3.15 (m, 2H), 3.11-2.97 (m, 2H), 2.71 (tdd, J=12.0, 6.4, 3.2 Hz, 1H), 2.64-2.52 (m, 1H), 0.85-0.78 (m, 1H), 0.75-0.60 (m, 3H). Analytical HPLC: RT=3.65 min (Method A).

Example 20

7-{14'-Oxa-3',4',10'-triazaspiro[cyclopropane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 2TFA Enantiomer A, and Example 21

7-{14'-Oxa-3',4',10'-triazaspiro[cyclopropane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 2TFA Enantiomer B

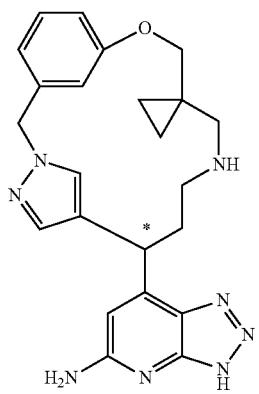 [SMILES: Nc1cc(C2CCNCC3(CC3)COc3cccc(c3)Cn3cc2cn3)c2nn[nH]c2n1]

Examples 20 and 21 were prepared by chiral SFC separation of Example 19 (Column: Lux 5µ Cellulose-4, eluted with 35% EtOH/0.1% DEA/65% $CO_2$ at 40° C. and 150 Bar.). Ex. 20 (peak 1): MS(ESI) m/z 431.1 (M+H). $^1$H NMR (500 MHz, $CD_3OD$) δ 8.14 (s, 1H), 7.69 (s, 1H), 7.28 (t, J=7.8 Hz, 1H), 7.01 (d, J=7.7 Hz, 1H), 6.85 (s, 1H), 6.81 (dd, J=8.3, 2.2 Hz, 1H), 5.96 (s, 1H), 5.51-5.32 (m, 2H), 4.54 (dd, J=12.4, 3.0 Hz, 1H), 4.13-4.02 (m, 2H), 3.28-3.21 (m, 1H), 3.19 (d, J=14.0 Hz, 1H), 3.11-2.98 (m, 2H), 2.71 (tdd, J=12.1, 6.3, 3.3 Hz, 1H), 2.65-2.53 (m, 1H), 0.85-0.78 (m, 1H), 0.76-0.61 (m, 3H).

Analytical HPLC: RT=3.86 min (Method A). Example 21 (peak 2): MS(ESI) m/z 431.1 (M+H). $^1$H NMR (500 MHz, $CD_3OD$) δ 8.13 (s, 1H), 7.69 (s, 1H), 7.28 (t, J=7.8 Hz, 1H), 7.01 (d, J=7.7 Hz, 1H), 6.88-6.74 (m, 2H), 5.95 (s, 1H), 5.55-5.31 (m, 2H), 4.54 (dd, J=12.4, 2.8 Hz, 1H), 4.15-4.01 (m, 2H), 3.28-3.21 (m, 1H), 3.20-3.14 (m, 1H), 3.09-3.00 (m, 2H), 2.71 (tdd, J=12.1, 6.3, 3.3 Hz, 1H), 2.64-2.53 (m, 1H), 0.84-0.77 (m, 1H), 0.76-0.61 (m, 3H). Analytical HPLC: RT=3.85 min (Method A).

Example 22

7-{14'-Oxa-3',4',10'-triazaspiro[cyclopentane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 2TFA

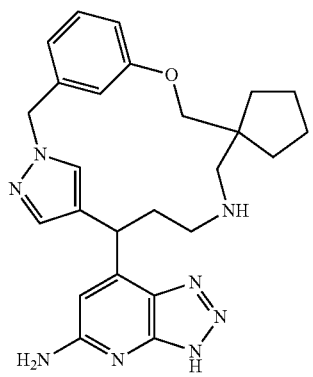 [SMILES: Nc1cc(C2CCNCC3(CCCC3)COc3cccc(c3)Cn3cc2cn3)c2nn[nH]c2n1]

(Prepared from tert-butyl ((1-(hydroxymethyl)cyclopentyl)methyl)carbamate) MS(ESI) m/z 459.2 (M+H). $^1$H NMR (500 MHz, $CD_3OD$) δ 8.06 (s, 1H), 7.62 (s, 1H), 7.31 (t, J=8.0 Hz, 1H), 7.05 (d, J=7.4 Hz, 1H), 6.93 (dd, J=8.1, 2.1 Hz, 1H), 6.75 (s, 1H), 6.05 (s, 1H), 5.47-5.32 (m, 2H), 4.41 (dd, J=12.2, 2.6 Hz, 1H), 4.02 (d, J=9.9 Hz, 1H), 3.87 (d, J=10.2 Hz, 1H), 3.15-3.07 (m, 2H), 2.81 (td, J=12.0, 2.3 Hz, 1H), 2.67 (tdd, J=12.2, 6.7, 3.0 Hz, 1H), 2.62-2.52 (m, 1H), 1.81-1.68 (m, 6H), 1.66-1.57 (m, 1H), 1.52-1.42 (m, 1H). One proton under solvent peak. Analytical HPLC: RT=4.49 min (Method A).

Example 23

7-[14-(Trifluoromethoxy)-18-oxa-3,4,10-triazatetracyclo[17.3.1.1$^{3,6}$.1$^{12,16}$]pentacosa-1(23),4,6(25),12,14,16(24),19,21-octaen-7-yl]-3H-[1,2,3]triazolo[4,5-b]pyridin-5-amine, 2TFA

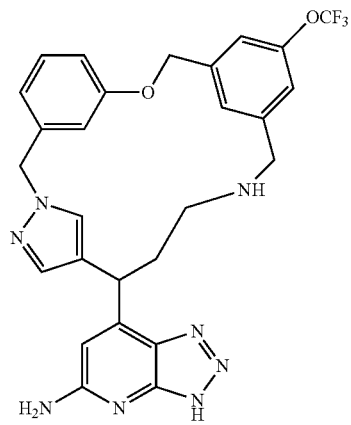 [SMILES: Nc1cc(C2CCNCc3cc(cc(OC(F)(F)F)c3)COc3cccc(c3)Cn3cc2cn3)c2nn[nH]c2n1]

23A. Methyl 3-bromo-5-(trifluoromethoxy)benzoate

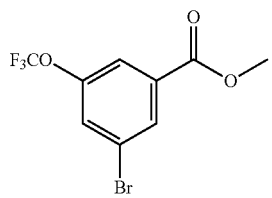 [SMILES: COC(=O)c1cc(Br)cc(OC(F)(F)F)c1]

A solution of 3-bromo-5-(trifluoromethoxy)benzoic acid (1.0 g, 3.5 mmol) and conc. $H_2SO_4$ (0.05 mL, 0.92 mmol) in MeOH (10 mL) was stirred at reflux ON. After evaporation of the solvent, the residue was dissolved in 1N NaOH and extracted 3× with EtOAc. The combined extracts were dried over $Na_2SO_4$, filtered and evaporated to give 23A (975 mg, 93%) as a colorless oil, which was used without further purification in the next step. $^1$H NMR (500 MHz, $CDCl_3$) δ 8.24-8.10 (m, 1H), 7.92-7.79 (m, 1H), 7.60 (s, 1H), 4.06-3.94 (m, 3H).

23B. Methyl 3-cyano-5-(trifluoromethoxy)benzoate

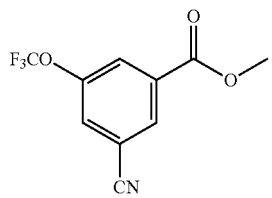 [SMILES: COC(=O)c1cc(C#N)cc(OC(F)(F)F)c1]

A mixture of 23A (0.60 g, 2.0 mmol) and dicyanozinc (0.15 g, 1.3 mmol) in DMF (4.0 ml) was sparged with argon for 30 min, and then was stirred at rt for 20 min before $(Ph_3P)_4Pd$ (0.23 g, 0.20 mmol) was added. The reaction mixture was heated at 80° C. ON. Additional (Ph₃P)₄Pd (0.23 g, 0.20 mmol) and dicyanozinc (0.15 g, 1.3 mmol) were added, and the reaction mixture was heated at 95° C. for 2 h. After cooling to rt, the mixture was filtered through Celite. The filtrate was evaporated to remove DMF. The residue was diluted with water and extracted with EtOAc (2×). The combined organic layers were washed with brine, dried over Na₂SO₄ and evaporated. The residue was purified by flash chromatography to provide the nitrile 23B (0.40 g, 81% yield) as a white solid. ¹H NMR (500 MHz, CDCl₃) δ 8.29 (t, J=1.4 Hz, 1H), 8.20-8.06 (m, 1H), 7.71 (s, 1H), 4.01 (s, 3H).

23C. tert-Butyl 3-(hydroxymethyl)-5-(trifluoromethoxy)benzylcarbamate

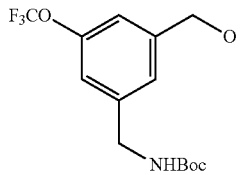

To a solution of 23B (0.40 g, 1.6 mmol) in THF (1.6 mL) was added a 1M solution of LAH in THF (4.9 mL, 4.9 mmol) dropwise at 0° C. The reaction mixture was gradually warmed up to rt and stirred ON. The reaction mixture was cooled to 0° C. and slowly quenched sequentially with H₂O (0.2 mL), 1N NaOH (0.2 mL) and H₂O (0.6 mL). After stirring this mixture for 15 min at rt, Boc₂O (0.38 mL, 1.6 mmol) was added. Stirring was continued for 1 h. The solids were removed by filtration through a pad of Celite, and washed with EtOAc. The filtrate was concentrated, and the residue purified by flash chromatography to provide 23C (0.24 g, 46% yield) as a colorless oil. ¹H NMR (500 MHz, CDCl₃) δ 7.21 (s, 1H), 7.14 (s, 1H), 7.06 (s, 1H), 5.00 (br. s., 1H), 4.70 (s, 2H), 4.32 (d, J=5.2 Hz, 2H), 2.25 (br. s., 1H), 1.48 (s, 9H).

23D. Methyl 3-((3-(((tert-butoxycarbonyl)amino)methyl)-5-(trifluoromethoxy)-benzyl)oxy)benzoate

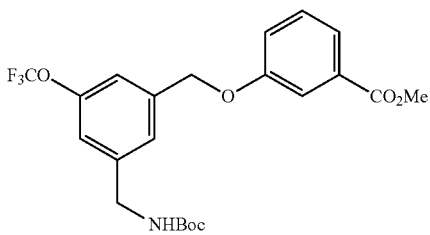 [SMILES: COC(=O)c1cccc(OCc2cc(CNC(=O)OC(C)(C)C)cc(OC(F)(F)F)c2)c1]

23C (0.242 g, 0.752 mmol) and methyl 3-hydroxybenzoate (0.104 g, 0.684 mmol) were dissolved in THF (1.4 mL). Triphenylphosphine (0.215 g, 0.820 mmol) was added, and the solution was stirred under argon and cooled to 0° C. DIAD (0.159 mL, 0.820 mmol) was added dropwise. The reaction mixture was stirred ON allowing the reaction mixture to gradually assume rt. The reaction mixture was evaporated to remove volatiles, and the residue purified by flash chromatography to yield 23D (274 mg, 88% yield) as a colorless oil. MS(ESI) m/z 456.0 (M+H).

23E. tert-Butyl 3-((3-(hydroxymethyl)phenoxy)methyl)-5-(trifluoromethoxy)-benzylcarbamate

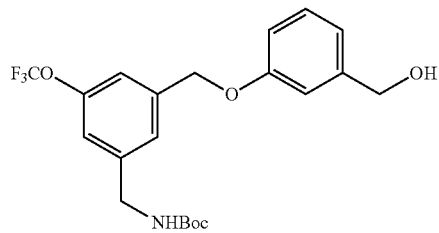 [SMILES: CC(C)(C)OC(=O)NCc1cc(COc2cccc(CO)c2)cc(OC(F)(F)F)c1]

23 D (0.27 g, 0.60 mmol) was dissolved in THF (1.2 mL) with stirring under argon at rt. A solution of LiBH₄, 2M in THF (0.60 mL, 1.2 mmol) was added in rapid dropwise fashion. MeOH (0.049 mL, 1.2 mmol) was then added slowly dropwise. The reaction mixture was stirred at room temperature for 1 h. An additional 0.2 mL of 2M LiBH₄ in THF was added, and the reaction was heated at 66° C. for 0.5 h to drive the reaction to completion. The reaction mixture was cooled in an ice bath and quenched with water, then 1M NaOH. EtOAc was added, and mixture was stirred to dissolve the solids, then transferred to a separatory funnel using additional water as needed to dissolve the remaining white solid. Phases were separated, and the aq. layer was reextracted 2× with EtOAc. The combined extracts were washed with brine, dried over Na₂SO₄, filtered and evaporated to provide 23E (263 mg, 102%) as a viscous oil. MS(ESI) m/z 428.0 (M+H).

23F. tert-Butyl 3-((3-((4-(4,4,5,5-tetramethyl-1,3,2-dioxaborolan-2-yl)-1H-pyrazol-1-yl)methyl)phenoxy)methyl)-5-(trifluoromethoxy)benzylcarbamate

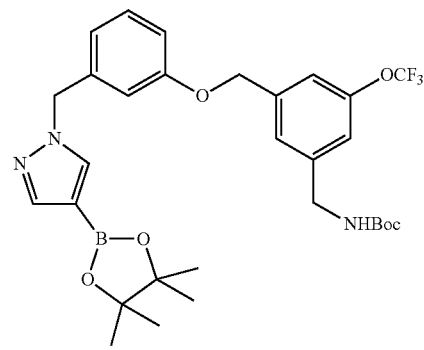 [SMILES: CC(C)(C)OC(=O)NCc1cc(COc2cccc(Cn3cc(B4OC(C)(C)C(C)(C)O4)cn3)c2)cc(OC(F)(F)F)c1]

A mixture of 4-(4,4,5,5-tetramethyl-1,3,2-dioxaborolan-2-yl)-1H-pyrazole (117 mg, 0.602 mmol) and 23E (257 mg, 0.602 mmol) in toluene (3.0 mL) was sonicated for 10 min to help dissolve the solids. Tris(butyl)phosphine (0.226 mL, 0.903 mmol) was added followed by TMAD (155 mg, 0.903 mmol), and the reaction mixture was stirred at rt ON. The reaction mixture was filtered, the solid washed with additional toluene, and the filtrate evaporated. The crude product was purified by flash chromatography to give 23F (294 mg, 81%) as a colorless oil. MS(ESI) m/z 604.2 (M+H).

Example 23 was prepared from 23F following the procedures described for the synthesis of Ex. 17 from 17D. MS(ESI) m/z 551.0 (M+H). ¹H NMR (500 MHz, CD₃OD)

δ 7.64 (s, 1H), 7.43 (s, 1H), 7.38-7.28 (m, 4H), 7.06 (dd, J=8.0, 1.9 Hz, 1H), 7.01 (d, J=7.7 Hz, 1H), 6.52 (s, 1H), 6.30 (s, 1H), 5.35-5.26 (m, 2H), 5.25-5.17 (m, 2H), 4.49 (dd, J=12.2, 3.2 Hz, 1H), 4.39 (d, J=13.5 Hz, 1H), 4.21 (d, J=13.5 Hz, 1H), 2.96 (ddd, J=12.0, 10.5, 6.1 Hz, 1H), 2.70-2.60 (m, 1H), 2.59-2.50 (m, 1H), 2.49-2.39 (m, 1H). Analytical HPLC: RT=5.37 min (Method A).

Example 24

7-{15,22-Difluoro-18-oxa-3,4,10-triazatetracyclo[17.3.1.1$^{3,6}$.1$^{12,16}$]pentacosa-1(23),4,6(25),12,14,16(24),19,21-octaen-7-yl}-3H-[1,2,3]triazolo[4,5-b]pyridin-5-amine, 2TFA

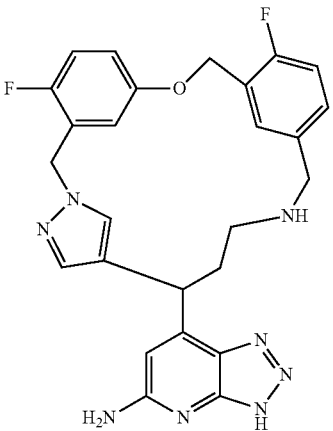 [SMILES: Nc1cc(C2CCNCc3ccc(F)c(c3)COc3ccc(F)c(c3)Cn3cc2cn3)c2nn[nH]c2n1]

24A. tert-Butyl N-{[4-fluoro-3-(hydroxymethyl)phenyl]methyl}carbamate

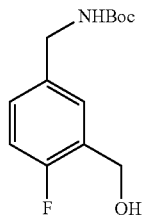 [SMILES: CC(C)(C)OC(=O)NCc1ccc(F)c(CO)c1]

To a solution of 5-cyano-2-fluorobenzoic acid (0.50 g, 3.0 mmol) in THF (3 ml) was added a solution of 1M LAH in THF (9.1 ml, 9.1 mmol) at 0° C. dropwise. The reaction mixture was gradually warmed up to rt and stirred ON. The reaction mixture was again cooled to 0° C. and slowly quenched sequentially with H$_2$O (0.2 mL), 1N NaOH (0.2 mL) and H$_2$O (0.6 mL). After stirring this mixture for 15 min at RT, Boc$_2$O (0.66 g, 3.0 mmol) was added. Stirring was continued for 2 h at rt. The solids were removed by filtration through Celite, and washed with EtOAc. The filtrate was concentrated, and the residue was purified by flash chromatography to provide 24A (0.33 g, 42%). $^1$H NMR (500 MHz, CDCl$_3$) δ 7.37 (dd, J=7.2, 2.2 Hz, 1H), 7.26-7.17 (m, 1H), 7.03 (dd, J=9.6, 8.5 Hz, 1H), 4.77 (d, J=6.1 Hz, 2H), 4.31 (br d, J=5.2 Hz, 2H), 1.87 (t, J=6.2 Hz, 1H), 1.48 (s, 9H).

24B. Methyl 2-fluoro-5-hydroxybenzoate

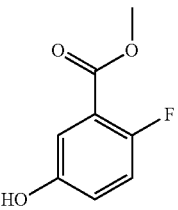

A solution of 2-fluoro-5-hydroxybenzoic acid (1.5 g, 9.6 mmol) and conc. H$_2$SO$_4$ (0.050 mL, 0.92 mmol) in MeOH (10 mL) was stirred at reflux ON. After evaporation of the solvent, the residue was dissolved in 1N NaOH and extracted 3× with EtOAc. The combined extracts were dried over Na$_2$SO$_4$, filtered and evaporated to give 24B (1.47 g, 90% yield) as a colorless solid which was used without further purification in the following reaction. $^1$H NMR (500 MHz, CDCl$_3$) δ 7.39 (dd, J=5.5, 3.3 Hz, 1H), 7.08-7.03 (m, 1H), 7.03-6.98 (m, 1H), 3.95 (s, 3H).

Example 24 was prepared as described for Example 23 by substituting 24A for 23C and 24B for methyl-3-hydroxybenzoate in Step 23D. MS(ESI) m/z 503.2 (M+H). $^1$H NMR (500 MHz, CD$_3$OD) δ 7.59 (s, 1H), 7.44 (s, 1H), 7.40 (br s, 1H), 7.33 (br d, J=6.3 Hz, 1H), 7.18-7.09 (m, 3H), 6.41 (s, 1H), 6.25 (br d, J=6.1 Hz, 1H), 5.31 (d, J=8.8 Hz, 2H), 5.30-5.25 (m, 1H), 5.24-5.18 (m, 1H), 4.47 (dd, J=9.5, 5.9 Hz, 1H), 4.05-3.97 (m, 1H), 3.96-3.90 (m, 1H), 2.67-2.62 (m, 1H), 2.61-2.52 (m, 1H), 2.39-2.32 (m, 2H). Analytical HPLC: RT=1.13 min (Method C).

Example 25

7-[(3R,4S,6S,10S)-4-Benzyl-2-oxa-7,13,14-triazatetracyclo[14.3.1.1$^{3,6}$.1$^{11,14}$]docosa-1(19),11(21),12,16(20),17-pentaen-10-yl]-3H-[1,2,3]triazolo[4,5-b]pyridin-5-amine, 2TFA, and Example 26

7-[(3R,4S,6S,10R)-4-Benzyl-2-oxa-7,13,14-triazatetracyclo[14.3.1.1$^{3,6}$.1$^{11,14}$]docosa-1(19),11(21),12,16(20),17-pentaen-10-yl]-3H-[1,2,3]triazolo[4,5-b]pyridin-5-amine, 2TFA

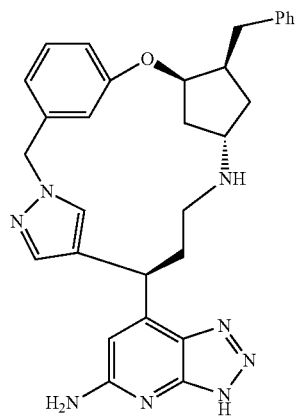

Example 25

Example 26

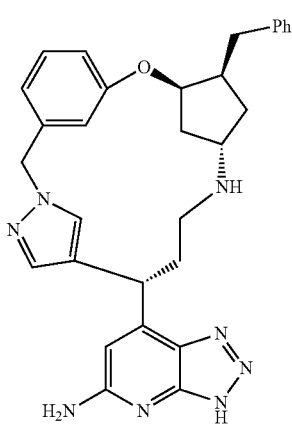

25A. Methyl 3-(41R,2S,4S)-2-benzyl-4-((tert-butoxycarbonyl)amino)cyclopentyl)oxy)benzoate

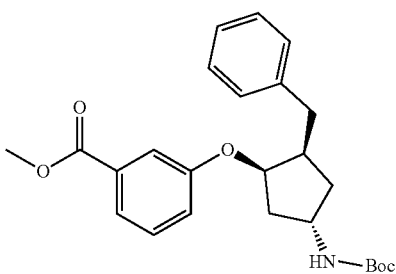 [SMILES: COC(=O)c1cccc(O[C@@H]2C[C@@H](NC(=O)OC(C)(C)C)C[C@@H]2Cc2ccccc2)c1]

A solution of Intermediate 6 (212 mg, 0.727 mmol), methyl 3-hydroxybenzoate (122 mg, 0.799 mmol), and triphenylphosphine (229 mg, 0.872 mmol) in THF (1.5 mL) was treated dropwise with DIAD (0.170 mL, 0.872 mmol) with stirring under nitrogen at room temperature. The reaction mixture was then stirred at rt for 16 h. The mixture was concentrated. The residue was purified by flash chromatography to provide 25A (200 mg, 64.7%) as a colorless oil. MS(ESI) m/z 370.0 (M-tBu+H).

25B. tert-Butyl ((1S,3S,4R)-3-benzyl-4-(3-(hydroxymethyl)phenoxy)cyclopentyl) carbamate

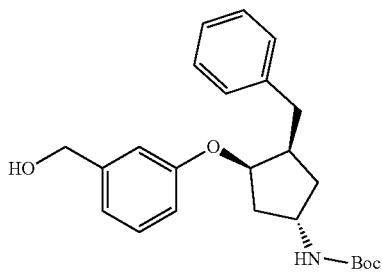 [SMILES: CC(C)(C)OC(=O)N[C@H]1C[C@H](Cc2ccccc2)[C@H](Oc2cccc(CO)c2)C1]

25A (0.20 g, 0.47 mmol) was dissolved in THF (0.94 mL) with stirring under argon. The solution was cooled to 0° C., and a 2M solution of LiBH₄ in THF (0.47 mL, 0.94 mmol) was added in rapid dropwise fashion. MeOH (38 μL, 0.94 mmol) was then added slowly dropwise. The reaction mixture was stirred at rt for 16 h. Another 0.2 mL of 2M LiBH₄ was added, and the reaction was heated at reflux for 4 h. Reaction mixture was cooled in an ice bath and quenched with water, then 1M NaOH. EtOAc was added, and mixture was stirred to dissolve the solids. The mixture was transferred to a separatory funnel with additional water to help dissolve the remaining white solid. Phases were separated, and the aq. layer was reextracted 2× with EtOAc. The combined extracts were washed with brine, dried over Na₂SO₄, filtered and evaporated. The residue was purified by flash chromatography to provide 25B (80 mg, 43%) as a colorless oil. MS(ESI) m/z 795.6 (2M+H).

25C. tert-Butyl ((14S,3S,4R)-3-benzyl-4-(3-((4-(4,4,5,5-tetramethyl-1,3,2-dioxaborolan-2-yl)-1H-pyrazol-1-yl)methyl)phenoxy)cyclopentyl)carbamate

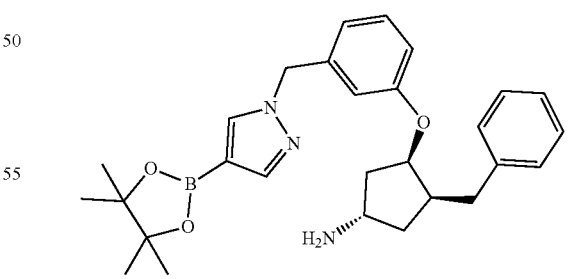

A mixture of 4-(4,4,5,5-tetramethyl-1,3,2-dioxaborolan-2-yl)-1H-pyrazole (39 mg, 0.20 mmol) and 25B (80 mg, 0.20 mmol) in toluene (1.0 mL) was sonicated for 10 min. Tris(butyl)phosphine (75 μL, 0.30 mmol) was added, followed by TMAD (52 mg, 0.30 mmol), and the reaction mixture was stirred at room temperature ON. The reaction mixture was filtered, the solid was washed with additional toluene, and the filtrate was evaporated. The residue was purified by flash chromatography to give 25C (115 mg, 100%) as a colorless oil. MS(ESI) m/z 574.3 (M+H).

25D. (1S,3S,4R)-3-Benzyl-4-(3-((4-(4,4,5,5-tetramethyl-1,3,2-dioxaborolan-2-yl)-1H-pyrazol-1-yl)methyl)phenoxy)cyclopentanamine, HCl To a solution of 25C (0.20 g, 0.35 mmol) in dioxane (1 mL) was added a solution of 4M HCl in dioxane (0.87 mL, 3.5 mmol). The reaction mixture was stirred at rt for 3 h. The solvents were removed by evaporation, and the residue was titurated with THF to give the crude product, 25D, which was used directly in the next step. MS(ESI) m/z 474.1 (M+H).

25E. tert-Butyl ((1S,3S,4R)-3-benzyl-4-(3-((4-(4,4,5,5-tetramethyl-1,3,2-dioxaborolan-2-yl)-1H-pyrazol-1-yl)methyl)phenoxy)cyclopentyl)((Z)-3-iodo-3-(3-trityl-5-(tritylamino)-3H-[1,2,3]triazolo[4,5-b]pyridin-7-yl)allyl)carbamate

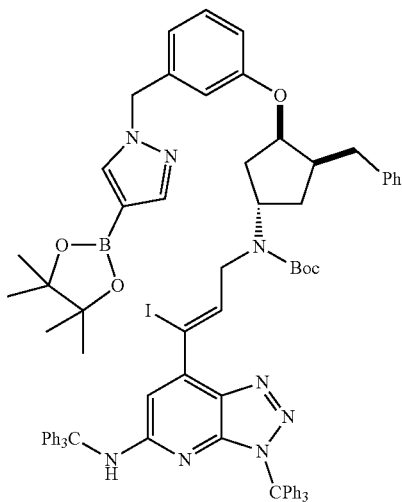

To a solution of 25D (178 mg, 0.349 mmol) in DMF (2.9 mL) was added cesium hydroxide monohydrate (147 mg, 0.873 mmol) and potassium iodide (48.3 mg, 0.291 mmol), and the mixture was stirred at rt for 30 min. A solution of Intermediate 2 (252 mg, 0.291 mmol) in DMF (0.5 mL) was then added dropwise. The reaction mixture was stirred for 10 min, followed by addition of Boc$_2$O (0.135 mL, 0.582 mmol). The reaction mixture was stirred at rt for an additional 2 h. The solids were removed by filtration, and the filtrate was concentrated. The residue was purified by flash chromatography to give 25E (200 mg, 50.7%) as a yellow oil. MS(ESI) m/z 1357.8 (M+H).

25F. tert-Butyl (14Z,51R,53S,55S,8Z)-55-benzyl-9-(3-trityl-5-(tritylamino)-3H-[1,2,3]triazolo[4,5-b]pyridin-7-yl)-11H-4-oxa-6-aza-1(1,4)-pyrazola-3(1,3)-benzena-5(1,3)-cyclopentanacyclononaphan-8-ene-6-carboxylate

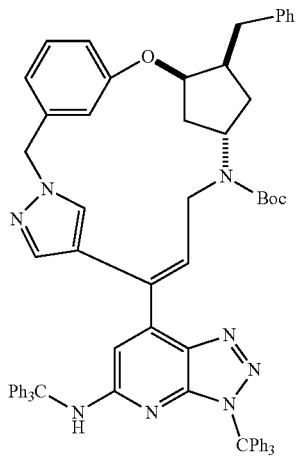

A mixture of 25E (0.200 g, 0.157 mmol), PdCl$_2$(dppf)-CH$_2$Cl$_2$ adduct (128 mg, 0.157 mmol) and potassium carbonate (217 mg, 1.57 mmol) was evacuated and back-filled with argon 3×, and then sparged dioxane (136 mL) and H$_2$O (21 mL) were added. The resulting reaction mixture was stirred at 85° C. for 16 h. The reaction mixture was filtered through Celite, and the filter cake was rinsed with EtOAc. The filtrate was concentrated. The residue was purified by flash chromatography to give 25F (77 mg, 45%) as a pale yellow oil. MS(ESI) m/z 1103.7 (M+H).

Examples 25 and 26

TFA (0.63 mL) was added to a solution of 25F (28 mg, 0.025 mmol) in dichloromethane (1.9 mL). The solution was stirred for 1 h, then triethylsilane (40 μL, 0.25 mmol) was then added. The reaction mixture was concentrated in vacuo. The residue was dissolved in EtOH (3 mL), and the solution was added to platinum(IV) oxide (2.9 mg, 0.013 mmol). This reaction mixture was stirred under hydrogen gas at 50 psi at rt for 16 h. The catalyst was removed by filtration and washed with MeOH. The filtrate was concentrated, and the crude product was purified with RP-HPLC to provide the separated diastereomers.

Example 25 (2.1 mg)

MS(ESI) m/z 521.3 (M+H). $^1$H NMR (500 MHz, CD$_3$OD) δ 8.26 (s, 1H), 7.59 (s, 1H), 7.37-7.27 (m, 5H), 7.25-7.18 (m, 1H), 7.16 (d, J=7.4 Hz, 1H), 6.86 (dd, J=8.3, 1.9 Hz, 1H), 6.69 (s, 1H), 6.58 (s, 1H), 5.44 (d, J=15.1 Hz, 1H), 5.27 (d, J=15.1 Hz, 1H), 4.35 (br d, J=10.2 Hz, 1H), 4.28 (q, J=3.8 Hz, 1H), 4.11-3.99 (m, 1H), 3.54-3.43 (m, 1H), 3.08 (dd, J=13.2, 7.4 Hz, 1H), 2.77-2.53 (m, 5H), 2.21 (ddd, J=14.2, 10.0, 7.4 Hz, 1H), 1.88-1.74 (m, 2H), 1.46-1.36 (m, 1H). Analytical HPLC RT=5.39 min (Method A).

Example 26 (4.0 mg)

MS(ESI) m/z 521.3 (M+H). $^1$H NMR (500 MHz, CD$_3$OD) δ 8.03 (s, 1H), 7.70 (s, 1H), 7.41-7.24 (m, 5H), 7.23-7.15 (m, 1H), 7.08 (d, J=7.4 Hz, 1H), 6.85 (dd, J=8.3, 1.7 Hz, 1H), 6.64 (br s, 1H), 6.13 (s, 1H), 5.54-5.37 (m, 2H), 4.65 (dd, J=11.6, 3.6 Hz, 1H), 4.58-4.46 (m, 1H), 3.97-3.80 (m, 1H), 3.20-3.02 (m, 3H), 2.78-2.67 (m, 1H), 2.67-2.47 (m, 3H), 2.13 (ddd, J=14.3, 9.5, 4.3 Hz, 1H), 2.05-1.91 (m, 1H), 1.89-1.70 (m, 2H). Analytical HPLC RT=5.58 min (Method A).

Example 27

7-[(17S)-18-Phenyl-16-oxa-2,8,9-triazapentacyclo[16.2.2.1$^{1,17}$.1$^{6,9}$.1$^{11,15}$]pentacosa-6(25),7,11(24),12,14-pentaen-5-yl]-3H-[1,2,3]triazolo[4,5-b]pyridin-5-amine, 2TFA

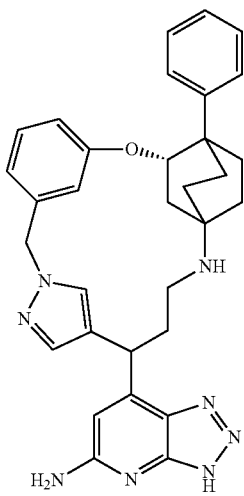 [SMILES: Nc1cc(C2CCNC34CCC(c5ccccc5)(CC3)[C@H](C4)Oc3cccc(c3)Cn3cc2cn3)c2nn[nH]c2n1]

27A. (S,Z)-4-((3-(5-Amino-3H-[1,2,3]triazolo[4,5-b]pyridin-7-yl)-3-(1-(3-((triisopropylsilyl)oxy)benzyl)-1H-pyrazol-4-yl)allyl)amino)-1-phenylbicyclo[2.2.2]octan-2-ol

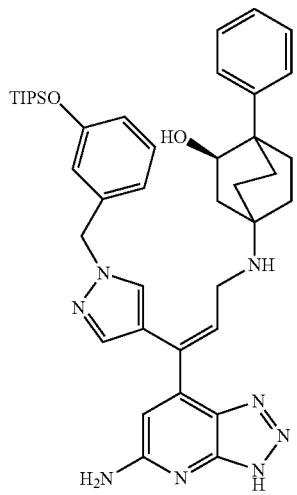

To a solution of Intermediate 5 (0.2 g, 0.2 mmol) in a mixture of THF (2 mL) and EtOH (2 mL) was added triethylamine (0.25 mL, 1.8 mmol) and Intermediate 10 (0.15 g, 0.60 mmol), and the mixture was heated to 60° C. for 6 hours. The solution was allowed to cool, and sodium borohydride (0.04 g, 1.0 mmol) was added in one portion. This mixture was stirred at rt for 16 h. The reaction mixture was partitioned between EtOAc and brine, and the aqueous layer extracted 2× with EtOAc. The combined extracts were washed with brine, dried over Na$_2$SO$_4$, filtered and evaporated. The product was purified on a silica gel column (pre-treated with 1% TEA/Hexanes) to give 27A (172 mg, 71.6%). MS(ESI) m/z 1203.9 (M+H).

27B. (S,Z)-tert-Butyl (3-(5-amino-3H-[1,2,3]triazolo[4,5-b]pyridin-7-yl)-3-(1-(3-hydroxybenzyl)-1H-pyrazol-4-yl)allyl)(3-hydroxy-4-phenylbicyclo[2.2.2]octan-1-yl)carbamate

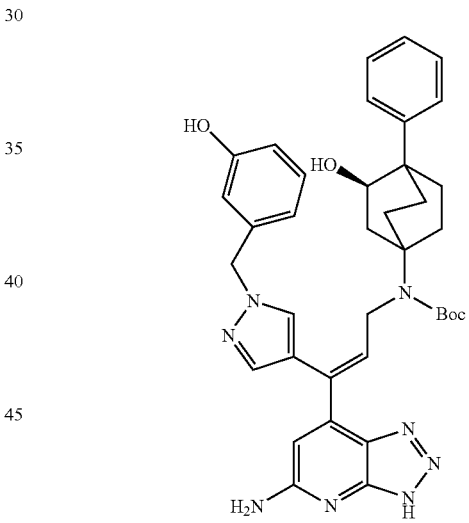

27A (138 mg, 0.115 mmol) was dissolved in a mixture of THF (0.191 mL) and 1N NaOH (0.191 mL). A solution of Boc$_2$O (0.050 g, 0.23 mmol) in THF (0.191 mL) was added. The reaction mixture was stirred at rt under nitrogen for 16 h. Another portion of Boc$_2$O (0.05 g, 0.23 mmol) was added. Stirring was continued at rt for 56 h. The reaction mixture was concentrated, and the residue was purified on a silica column (pre-treated with 1% TEA in hexanes) to give 27B (114 mg, 87%) as a greyish oil. MS(ESI) m/z 1147.7 (M+H).

27C. tert-Butyl (4Z,17S)-18-phenyl-5-[3-(triphenyl-methyl)-5-[(triphenylmethyl)amino]-3H-[1,2,3]tri-azolo[4,5-b]pyridin-7-yl]-16-oxa-2,8,9-triazapenta-cyclo[16.2.2.1$^{1,17}$.1$^{6,9}$.1$^{11,15}$]pentacosa-4,6(25),7,11(24),12,14-hexaene-2-carboxylate

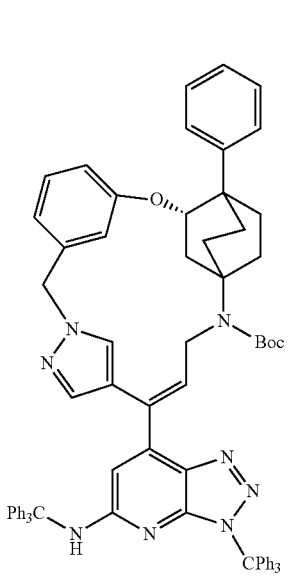

A solution of 27B (0.030 g, 0.026 mmol) in toluene (5.2 mL) in a 20 mL pressure vial was degassed by bubbling with argon for 15 min. A 1 M solution of cyanomethylenetributylphosphorane in toluene (0.10 mL, 0.10 mmol) was added slowly dropwise at rt. The reaction mixture was then heated with stirring at 100° C. for 16 h. The volatiles were removed by evaporation. Purification of the residue by flash chromatography gave 27C (23 mg, 85%). MS(ESI) m/z 1029.5 (M+H).

Example 27

TFA (0.56 mL) was added to a solution of 27C (23 mg, 0.022 mmol) in DCM (1.7 mL) to produce a bright yellow solution. After stirring for 1 h at rt, triethylsilane (36 µL, 0.22 mmol) was added. The reaction mixture was then concentrated in vacuo. The residue was dissolved in EtOH (3 mL), and the solution was added to PtO$_2$ (2.5 mg, 0.011 mmol). This mixture was stirred under 50 psi of hydrogen gas at rt for 16 h. The catalyst was removed by filtration and rinsed with MeOH. The filtrate was concentrated, and the product was purified by RP-HPLC to provide the title compound (5.1 mg, 28%) as a 1:1 mixture of diastereomers. MS(ESI) m/z 547.4 (M+H). Analytical HPLC RT=5.23 min (Method A).

Example 28

7-[(17R)-18-Phenyl-16-oxa-2,8,9-triazapentacyclo[16.2.2.1$^{1,17}$.1$^{6,9}$.1$^{11,15}$]pentacosa-6(25),7,11(24),12,14-pentaen-5-yl]-3H-[1,2,3]triazolo[4,5-b]pyridin-5-amine

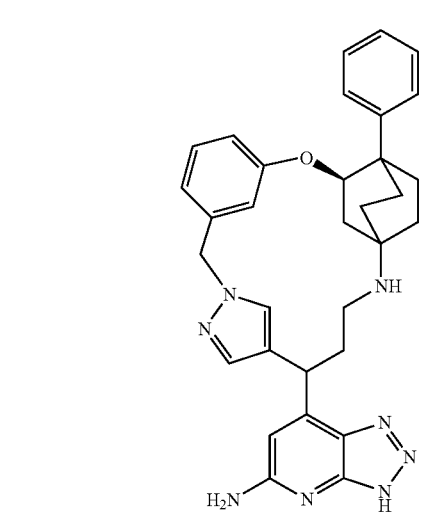 [SMILES: Nc1cc(C2CCNC34CCC(c5ccccc5)(CC3)[C@@H](C4)Oc3cccc(c3)Cn3cc2cn3)c2nn[nH]c2n1]

Example 28 was prepared as described for Example 27 by substituting Intermediate 9 for Intermediate 10 in step 27A. The product was isolated as 1:1 mixture of diastereomers. MS(ESI) m/z 547.4 (M+H). Analytical HPLC RT=5.58 min (Method A).

Example 29

7-[(18S)-19-Phenyl-17-oxa-2,8,9-triazapentacyclo[17.2.2.1$^{1,18}$.1$^{6,9}$.1$^{12,16}$]hexacosa-6(26),7,12(25),13,15-pentaen-5-yl]-3H-[1,2,3]triazolo[4,5-b]pyridin-5-amine, 2TFA

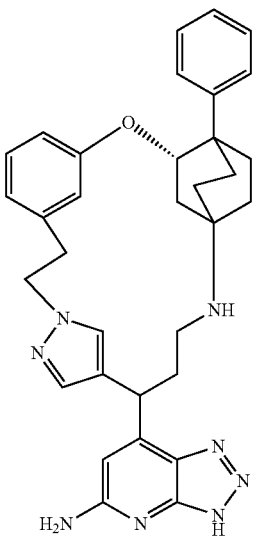 [SMILES: Nc1cc(C2CCNC34CCC(c5ccccc5)(CC3)[C@H](C4)Oc3cccc(c3)CCn3cc2cn3)c2nn[nH]c2n1]

29A. Methyl 2-(3-((triisopropylsilyl)oxy)phenyl)acetate

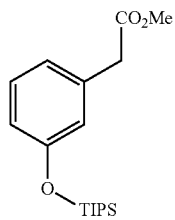

Methyl 2-(3-hydroxyphenyl)acetate (0.75 g, 4.5 mmol) and imidazole (0.36 g, 5.3 mmol) were dissolved in DMF (3.0 ml). The solution was cooled to 0° C. while TIPS-Cl (1.2 ml, 5.0 mmol) was added dropwise. After completion of addition, stirring was continued at 0° C. for 1 h, then ON at rt. Additional imidazole (0.18 g, 2.7 mmol) and TIPS-Cl (0.58 mL, 2.5 mmol) were added. The reaction mixture was stirred for an additional 5 h. Reaction mixture was diluted with water and extracted 3× with $Et_2O$. The combined extracts were washed with water and brine, then dried over $Na_2SO_4$, filtered and evaporated to provide 29A. MS(ESI) m/z 323.1 (M+H).

29B. 2-(3-((Triisopropylsilyl)oxy)phenyl)ethanol

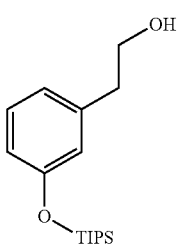

29B was prepared from 29A in 91% yield using the procedure described for Intermediate 3, step B. MS(ESI) m/z 295.1 (M+H).

29C. 4-(4,4,5,5-Tetramethyl-1,3,2-dioxaborolan-2-yl)-1-(3-((triisopropylsilyl)oxy)-phenethyl)-1H-pyrazole

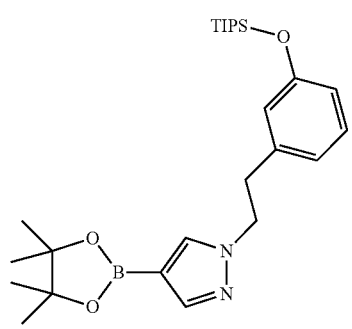

A mixture of 4-(4,4,5,5-tetramethyl-1,3,2-dioxaborolan-2-yl)-1H-pyrazole (308 mg, 1.59 mmol) and 29B (468 mg, 1.59 mmol) in toluene (7.9 mL) was sonicated for 10 min. Tris(butyl)phosphine (0.595 mL, 2.38 mmol) was added, followed by TMAD (410 mg, 2.38 mmol), and the reaction was stirred at room temperature for 3 h. The reaction mixture was filtered, and the solid washed with additional toluene. The filtrate was evaporated, and the residue purified by flash chromatography to provide 29C. MS(ESI) m/z 471.2 (M+H).

29D. (Z)-3-(1-(3-((Triisopropylsilyl)oxy)phenethyl)-1H-pyrazol-4-yl)-3-(3-trityl-5-(tritylamino)-3H-[1,2,3]triazolo[4,5-b]pyridin-7-yl)acrylaldehyde

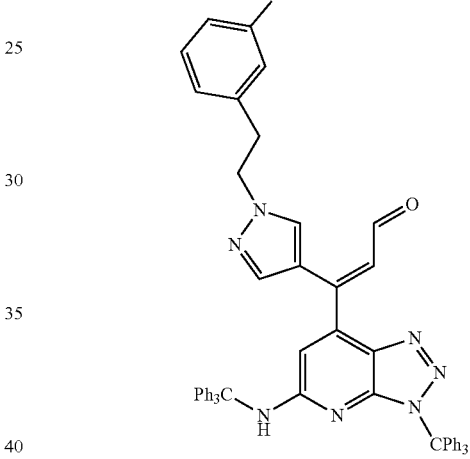

29D was prepared from 29C and intermediate 1 using the procedures described for the syntheses of Intermediate 4 and Intermediate 5. MS(ESI) m/z 1016.5 (M+H).

Example 29 was prepared following the steps outlined for Ex. 27, substituting 29D for Intermediate 5 in Step 27A. The product was isolated as a 1:1 mixture of diastereomers. MS(ESI) m/z 579.3 (M+H). $^1$H NMR (500 MHz, $CD_3OD$) δ 7.59 (s, 1H), 7.42 (s, 1H), 7.40-7.36 (m, 2H), 7.34-7.29 (m, 2H), 7.23-7.17 (m, 1H), 6.99 (t, J=7.8 Hz, 1H), 6.60 (dd, J=8.1, 2.1 Hz, 1H), 6.52 (d, J=7.4 Hz, 1H), 6.49-6.44 (m, 2H), 4.50 (dd, J=8.8, 6.6 Hz, 1H), 4.37-4.28 (m, 3H), 3.05 (t, J=6.7 Hz, 2H), 3.01-2.91 (m, 2H), 2.65-2.56 (m, 1H), 2.55-2.42 (m, 2H), 2.39-2.29 (m, 1H), 2.12-2.01 (m, 1H), 2.00-1.90 (m, 2H), 1.85 (br t, J=12.7 Hz, 2H), 1.82-1.73 (m, 2H), 1.72-1.66 (m, 1H). Analytical HPLC RT=1.40 min (Method C).

Example 30

7-{8,9,15-triazatetracyclo[16.3.1.1²,⁶.1⁸,¹¹]tetracosa-1(22),2,4,6(24),9,11(23),18,20-octaen-12-yl}-3H-[1,2,3]triazolo[4,5-b]pyridin-5-amine, 2TFA

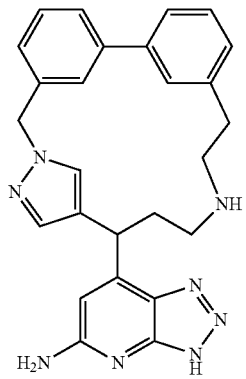 [SMILES: Nc1cc(C2CCNCCc3cccc(c3)-c3cccc(c3)Cn3cc2cn3)c2nn[nH]c2n1]

30A. tert-Butyl (2-(3'-(hydroxymethyl)-[1,1'-biphenyl]-3-yl)ethyl)carbamate

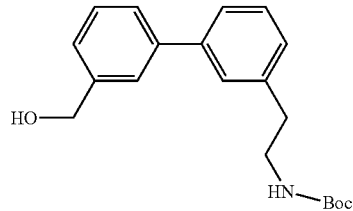 [SMILES: CC(C)(C)OC(=O)NCCc1cccc(-c2cccc(CO)c2)c1]

A mixture of tert-Butyl 3-bromophenethylcarbamate (0.20 g, 0.67 mmol), Pd(PPh₃)₄ (0.15 g, 0.13 mmol) and (3-(hydroxymethyl)phenyl)boronic acid (0.15 g, 1.0 mmol) was dissolved in dioxane (2 mL), and 2M Na₂CO₃ (1 mL) was added. The reaction mixture was stirred at 100° C. ON. After cooling to rt, the reaction mixture was filtered, and the filtrate was concentrated. The product was purified by silica gel chromatography to provide 30A (220 mg, 101%) as a colorless oil. MS(ESI) m/z 655.4 (2M+H).

Example 30 was prepared from 30A using the procedures described for 9E and the preparation of Ex. 7 from 7F. MS(ESI) m/z 451.2 (M+H). ¹H NMR (500 MHz, CD₃OD) δ 8.11 (s, 1H), 7.81 (s, 1H), 7.61-7.51 (m, 2H), 7.47 (td, J=7.7, 2.5 Hz, 2H), 7.38-7.29 (m, 2H), 7.14 (s, 1H), 6.83 (s, 1H), 6.30 (s, 1H), 5.58-5.45 (m, 2H), 4.59 (dd, J=12.1, 2.2 Hz, 1H), 3.57-3.45 (m, 2H), 3.43-3.34 (m, 2H), 3.17-3.06 (m, 2H), 2.72-2.61 (m, 1H), 2.60-2.49 (m, 1H). Analytical HPLC RT=4.31 min (Method A).

Example 31

7-[(3S,4S)-4-Benzyl-2-oxa-6,12,13-triazatetracyclo[13.3.1.1³,⁶.1¹⁰,¹³]henicosa-1(18),10(20),11,15(19),16-pentaen-9-yl]-3H-[1,2,3]triazolo[4,5-b]pyridin-5-amine, 2TFA

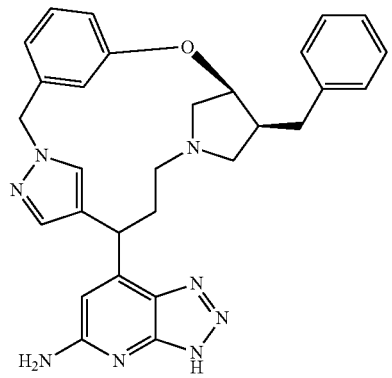 [SMILES: Nc1cc(C2CCN3C[C@H](Cc4ccccc4)[C@@H](C3)Oc3cccc(c3)Cn3cc2cn3)c2nn[nH]c2n1]

31A. (3R,4S)-4-Benzyl-1-((Z)-3-(1-(3-((triisopropylsilyl)oxy)benzyl)-1H-pyrazol-4-yl)-3-(3-trityl-5-(tritylamino)-3H-[1,2,3]triazolo[4,5-b]pyridin-7-yl)allyl)pyrrolidin-3-ol

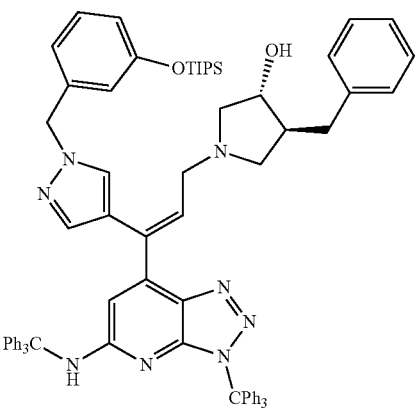

To Intermediate 5 (0.10 g, 0.10 mmol) in DCM (1 mL) was added Intermediate 7 (24 mg, 0.11 mmol) under nitrogen. The mixture was stirred for 15 min, followed by addition of sodium triacetoxyborohydride (25 mg, 0.12 mmol). Stirring was continued for 1 h at rt. The reaction mixture was quenched with sat'd aq. NaHCO₃ (3 mL), and then diluted with EtOAc (3 mL). The phases were separated, and the aq. layer extracted twice more with EtOAc (2 mL). The combined organic extracts were washed with brine, dried over Na₂SO₄, filtered and evaporated to provide 31A (129 mg, 93%). MS(ESI) m/z 1163.6 (M+H).

Example 31 was prepared from 31A following the steps described for the preparation of Example 27 from 27A. MS(ESI) m/z 507.3 (M+H). ¹H NMR (500 MHz, CD₃OD) δ 7.96 (s, 1H), 7.66 (s, 1H), 7.43-7.30 (m, 6H), 7.30-7.25 (m, 1H), 7.23 (d, J=7.7 Hz, 1H), 6.89 (dd, J=8.1, 2.1 Hz, 1H), 6.66 (s, 1H), 5.58 (d, J=16.5 Hz, 1H), 5.49 (s, 1H), 5.42 (d, J=16.5 Hz, 1H), 4.51 (t, J=3.4 Hz, 1H), 4.43 (dd, J=12.7, 2.2

Hz, 1H), 3.89 (dd, J=11.3, 7.2 Hz, 1H), 3.72 (td, J=12.4, 6.2 Hz, 1H), 3.48-3.40 (m, 1H), 3.15 (d, J=14.0 Hz, 1H), 3.11-3.03 (m, 1H), 2.99-2.88 (m, 2H), 2.79-2.60 (m, 2H), 2.41-2.30 (m, 1H). Analytical HPLC: RT=5.27 min (Method A).

Example 32

7-[(11S,14R)-16-Oxa-3,4,10-triazatetracyclo [15.3.1.1$^{3,6}$.1$^{11,1^{4}}$]tricosa-1(21),4,6(23),17,19-pentaen-7-yl]-3H-[1,2,3]triazolo[4,5-b]pyridin-5-amine, 2TFA

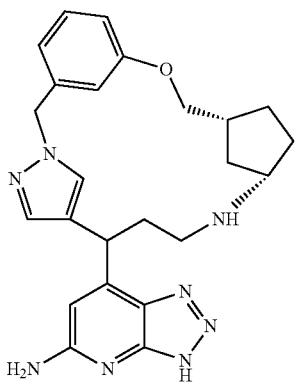 [SMILES: Nc1cc(C2CCN[C@H]3CC[C@@H](COc4cccc(c4)Cn4cc2cn4)C3)c2nn[nH]c2n1]

32A. tert-Butyl 01S,3R)-3-(hydroxymethyl)cyclopentyl)carbamate

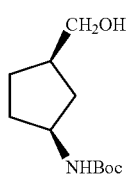 [SMILES: CC(C)(C)OC(=O)N[C@H]1CC[C@@H](CO)C1]

(1R,3S)-3-((tert-Butoxycarbonyl)amino)cyclopentanecarboxylic acid (0.13 g, 0.58 mmol) was dissolved in THF (4 mL), and TEA (0.18 mL, 1.3 mmol) was added. The solution was cooled to 0° C., and ethyl chloroformate (0.061 mL, 0.63 mmol) was added dropwise. The reaction mixture was stirred at 0° C. for 30 min, then filtered into a flask cooled at 0° C. using 2-3 mL THF to transfer. A solution of sodium borohydride (0.065 g, 1.7 mmol) in a minimum of water was then added to the filtrate as a single portion. Stirring was continued in the ice bath for 10-15 min, then at room temperature for 1 h. The reaction mixture was diluted with water and EtOAc. The phases were separated, and the aq. layer extracted 2× with EtOAc. The combined organic extracts were washed with brine, dried over $Na_2SO_4$, filtered and evaporated. Residue was purified by silica gel chromatography to provide 32A (0.108 g, 87%). $^1$H NMR (500 MHz, CDCl$_3$) δ 4.70 (br. s., 1H), 3.95 (br. s., 1H), 3.58 (d, J=5.78 Hz, 2H), 2.04-2.31 (m, 2H), 1.87-1.99 (m, 1H), 1.70-1.83 (m, 1H), 1.52-1.58 (m, 1H), 1.46-1.52 (m, 2H), 1.44 (s, 9H), 1.07-1.19 (m, 1H).

32B. 3-((4-(4,4,5,5-Tetramethyl-1,3,2-dioxaborolan-2-yl)-1H-pyrazol-1-yl)methyl)phenol

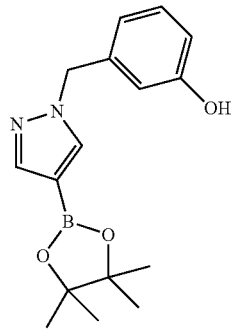 [SMILES: CC1(C)OB(c2cnn(Cc3cccc(O)c3)c2)OC1(C)C]

A 1M solution of TBAF in THF (2.25 mL, 2.25 mmol) was added at 0° C. to a solution of Intermediate 3 (0.514 g, 1.13 mmol) in THF (5.6 ml). When the reaction was complete by LCMS, the mixture was diluted with water and extracted with EtOAc (3×). The combined organic extracts were washed with brine, dried over $Na_2SO_4$, filtered and concentrated. Purification by silica gel chromatography provided 32B (0.226 g, 66.9%) MS(ESI) m/z 300.8 (M+H).

Example 32 was prepared from 32A and 32B following the procedures described for 9D, 9E, and the preparation of Ex. 7 from 7F. Example 32 was obtained as a 1:1 mixture of diastereomers. MS(ESI) m/z 445.1 (M+H). Analytical HPLC: RT=3.85 min (Method A).

Example 33

7-{5-Amino-3H-[1,2,3]triazolo[4,5-b]pyridin-7-yl}-13-(2-phenylethyl)-3,4,10,13-tetraazatricyclo [13.3.1.1$^{3,6}$]icosa-1(19),4,6(20),15,17-pentaen-12-one, 2TFA

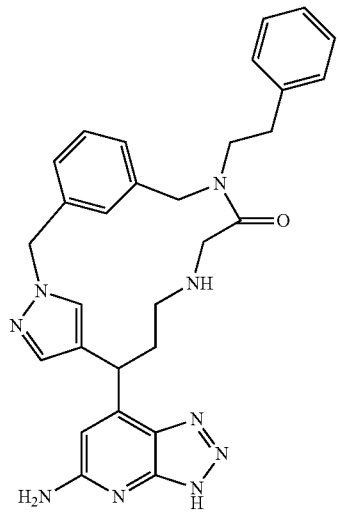 [SMILES: Nc1cc(C2CCNCC(=O)N(CCc3ccccc3)Cc3cccc(c3)Cn3cc2cn3)c2nn[nH]c2n1]

33A. Methyl 3-((phenethylamino)methyl)benzoate

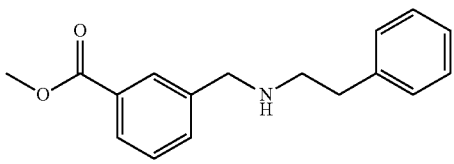 [SMILES: COC(=O)c1cccc(CNCCc2ccccc2)c1]

Methyl 3-formylbenzoate (1.0 g, 6.1 mmol) was dissolved in MeOH (20 ml) with stirring under argon. Phenethylamine (0.77 mL, 6.1 mmol) was added, and the reaction mixture was heated at reflux in a 75° C. oil bath for 2.5 h. The mixture was cooled to rt and evaporated. The residue was redissolved in MeOH (10 mL), and the solution was stirred at rt under argon while sodium borohydride (0.46 g, 12 mmol) was added in small portions. The resulting reaction mixture was stirred ON at rt. The reaction mixture was diluted with water and extracted 3× with EtOAc. The combined extracts were washed with brine, dried over $Na_2SO_4$, filtered and evaporated. The crude product was obtained as a yellow oil which was used without further purification (1.64 g, 100%). $^1$H NMR (500 MHz, $CDCl_3$) δ 7.96 (s, 1H), 7.92 (d, J=7.70 Hz, 1H), 7.49 (d, J=7.43 Hz, 1H), 7.38 (t, J=7.55 Hz, 1H), 7.27-7.32 (m, 2H), 7.17-7.24 (m, 3H), 3.91 (s, 3H), 3.85 (s, 2H), 2.87-2.94 (m, 2H), 2.80-2.87 (m, 2H).

33B. (3-((Phenethylamino)methyl)phenyl)methanol

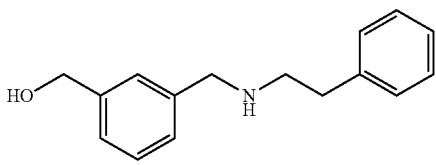 [SMILES: OCc1cccc(CNCCc2ccccc2)c1]

33A (1.47 g, 5.47 mmol) was dissolved in THF (25 ml) with stirring at room temperature under argon. A 2M solution of $LiBH_4$ in THF (5.47 ml, 10.9 mmol) was added, followed by dropwise addition of MeOH (0.443 ml, 10.9 mmol). The reaction mixture was stirred ON at rt. The reaction mixture was then heated to reflux for 2-3 h to drive the reaction to completion. After cooling to room temperature and then in an ice bath, the reaction mixture was quenched with 1M HCl until the mixture was acidic and all solids were in solution. The mixture was stirred for 20 min at room temperature, then adjusted to alkaline pH with 1M NaOH and extracted 3× with EtOAc. The combined extracts were washed with brine, dried over $Na_2SO_4$, filtered and evaporated. Purification of the residue on silica gel provided 33B (0.441 g, 33.4%). MS(ESI) m/z 242.1 (M+H).

33C. tert-Butyl (2-((3-(hydroxymethyl)benzyl)(phenethyl)amino)-2-oxoethyl)carbamate

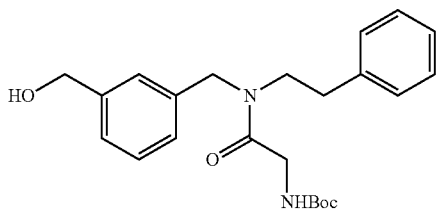 [SMILES: CC(C)(C)OC(=O)NCC(=O)N(CCc1ccccc1)Cc1cccc(CO)c1]

A mixture of 33B (0.25 g, 1.0 mmol) and 2-((tert-butoxycarbonyl)amino)acetic acid (0.18 g, 1.0 mmol) was dissolved in DMF (10 mL). NMM (0.57 mL, 5.2 mmol), HOBT monohydrate (0.24 g, 1.5 mmol) and EDC (0.30 g, 1.5 mmol) were added, and the reaction mixture was stirred ON at rt under argon. The reaction mixture was diluted with water and extracted 3× with EtOAc. The combined extracts were washed with water, 5% aq. citric acid, sat'd aq. $NaHCO_3$ and brine, then dried over $Na_2SO_4$, filtered and evaporated to provide 33C (0.39 g, 95%). MS(ESI) m/z 399.1 (M+H).

33D. tert-Butyl (2-oxo-2-(phenethyl(3-((4-(4,4,5,5-tetramethyl-1,3,2-dioxaborolan-2-yl)-1H-pyrazol-1-yl)methyl)benzyl)amino)ethyl)carbamate

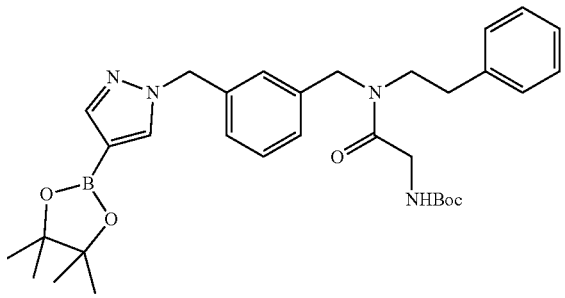 [SMILES: CC(C)(C)OC(=O)NCC(=O)N(CCc1ccccc1)Cc1cccc(Cn2cc(B3OC(C)(C)C(C)(C)O3)cn2)c1]

4-(4,4,5,5-Tetramethyl-1,3,2-dioxaborolan-2-yl)-1H-pyrazole (0.20 g, 1.0 mmol) and 33C (0.39 g, 0.98 mmol) were dissolved in toluene (10 ml). $nBu_3P$ (0.37 ml, 1.5 mmol) was added, followed by TMAD (0.25 g, 1.5 mmol). The reaction mixture was stirred ON at room temperature under argon. The mixture was filtered, and the solid washed with a little toluene. The filtrate was evaporated. Purification by silica gel chromatography provided 33D (0.34 g, 61%). MS(ESI) m/z 575.3 (M+H).

33E. 2-Amino-N-phenethyl-N-(3-((4-(4,4,5,5-tetramethyl-1,3,2-dioxaborolan-2-yl)-1H-pyrazol-1-yl)methyl)benzyl)acetamide, HCl

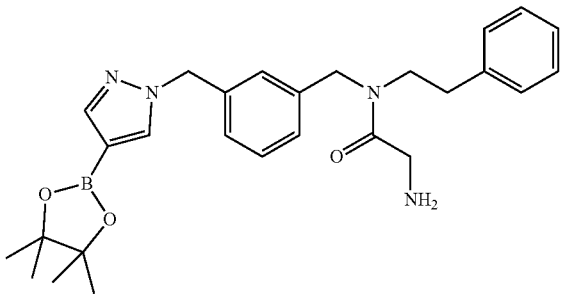 [SMILES: CC1(C)OB(c2cnn(Cc3cccc(CN(CCc4ccccc4)C(=O)CN)c3)c2)OC1(C)C]

33D (0.34 g, 0.59 mmol) was dissolved in dioxane (2.0 ml), and a solution of 4N HCl in dioxane (1.5 ml, 5.9 mmol) was added. The solution was stirred at rt under argon for ~1 h, then the solvents were removed bu evaporation in vacuo. The residue was triturated with ether and dried ON. 33E was obtained as a white solid and used without further purification. MS(ESI) m/z 475.2 (M+H).

33F. (Z)-tert-Butyl (3-iodo-3-(3-trityl-5-(tritylamino)-3H-[1,2,3]triazolo[4,5-b]pyridin-7-yl)allyl)(2-oxo-2-(phenethyl(3-((4-(4,4,5,5-tetramethyl-1,3,2-dioxaborolan-2-yl)-1H-pyrazol-1-yl)methyl)benzyl)amino)ethyl)carbamate

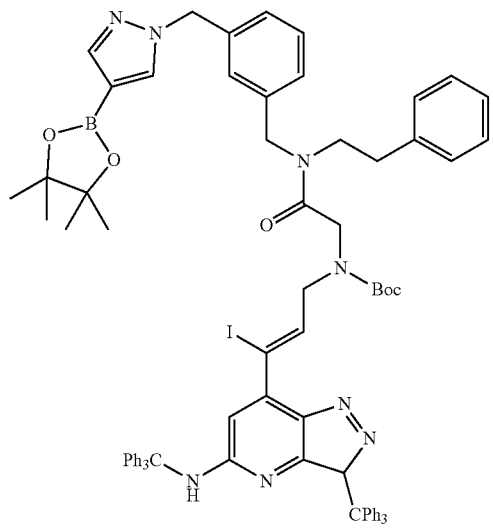

To 33E (0.18 g, 0.35 mmol) in DMF (1.1 ml) was added cesium hydroxide monohydrate (0.16 g, 0.92 mmol), and the mixture was stirred at rt for 30 min. KI (0.038 g, 0.23 mmol) and Intermediate 2 (0.20 g, 0.23 mmol) were added, and stirring was continued for 10 min. BOC₂O (0.11 ml, 0.46 mmol) was added to the reaction mixture, and stirring was continued for another 1 h. The reaction mixture was filtered to removed the solids, which were washed with EtOAc. The filtrate was concentrated. The residue was taken up in DCM and filtered. Purification by flash chromatography provided 33F (0.227 g, 72.3% yield) as a brownish yellow foam that was used without further purification. MS(ESI) m/z 1358.3 (M+H).

33G. tert-Butyl (14Z,10Z)-6-oxo-5-phenethyl-11-(3-trityl-5-(tritylamino)-3H-[1,2,3]triazolo[4,5-b]pyridin-7-yl)-11H-5,8-diaza-1(1,4)-pyrazola-3(1,3)-benzenacycloundecaphan-10-ene-8-carboxylate

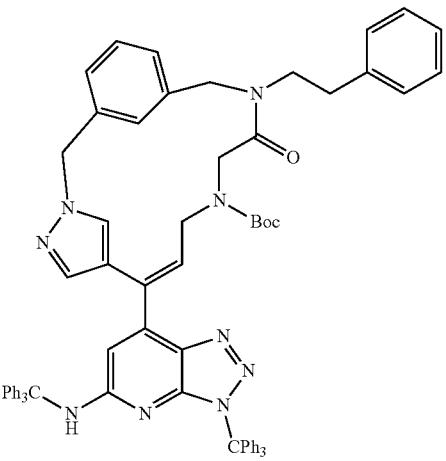

33F (0.10 g, 0.074 mmol), K₂CO₃ (0.10 g, 0.74 mmol) and PdCl₂(dppf)-DCM adduct (0.06 g, 0.074 mmol) were weighed into a 250 mL flask. The flask was evacuated and backfilled with argon 3×. Dioxane (60 mL) and water (9.2 mL) were added, and the mixture was degassed by careful application of vacuum and backfilling with argon 3×. The reaction mixture was then stirred and heated in an 85° C. oil bath ON. The reaction mixture was filtered through a Celite cartridge which was washed with additional EtOAc. The filtrate was evaporated. Purification by silica gel chromatography provided 33G as a pale yellow solid (34 mg, 42%). MS(ESI) m/z 1104.5 (M+H).

Example 33 was prepared from 33G as described for the conversion of 27C to Ex. 27 MS(ESI) m/z 522.2 (M+H). ¹H NMR (500 MHz, CD₃OD) δ 7.95 (s, 1H), 7.60 (s, 1H), 7.40 (s, 2H), 7.37-7.34 (m, 1H), 7.33-7.27 (m, 3H), 7.02 (br d, J=6.6 Hz, 2H), 6.96-6.86 (m, 1H), 6.71 (s, 1H), 5.49-5.33 (m, 2H), 4.44 (br dd, J=11.4, 3.7 Hz, 1H), 3.66-3.49 (m, 2H), 3.33 (dt, J=3.3, 1.7 Hz, 4H), 2.96-2.81 (m, 3H), 2.58-2.46 (m, 2H), 2.41 (br s, 1H). Analytical HPLC: RT=4.60 (Method A).

Example 34

7-[(12S,13R)-12-Phenyl-15-oxa-3,4,10-triazatetracyclo[14.3.1.1³,⁶.1¹⁰,¹³]docosa-1(20),4,6(22),16,18-pentaen-7-yl]-3H-[1,2,3]triazolo[4,5-b]pyridin-5-amine

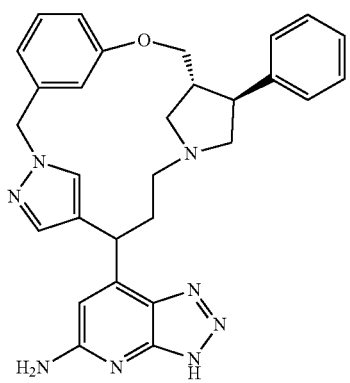 [SMILES: Nc1cc(C2CCN3C[C@H](COc4cccc(c4)Cn4cc2cn4)[C@@H](c2ccccc2)C3)c2nn[nH]c2n1]

34A. (3R,4S)-tert-Butyl 3-(hydroxymethyl)-4-phenylpyrrolidine-1-carboxylate

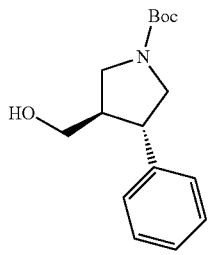 [SMILES: CC(C)(C)OC(=O)N1C[C@H](CO)[C@@H](c2ccccc2)C1]

(3R,4S)-1-tert-Butyl 3-methyl 4-phenylpyrrolidine-1,3-dicarboxylate (352 mg, 1.15 mmol) was dissolved in THF (12 mL), and the solution was cooled in an ice bath with stirring under argon. A solution of 2M LiBH₄ in THF (1.73 mL, 3.46 mmol) was added dropwise, and the mixture was stirred for 1 h in the ice bath, then ON at room temperature. The reaction mixture was cooled to 0° C. and quenched with 1M HCl to pH 1. After stirring for 30 min, the pH was adjusted to 9-10 with solid K₂CO₃, and the mixture was extracted 2× with DCM. The combined extracts were washed with brine, dried over Na₂SO₄, filtered and evaporated. Purification on silica gel provided 34A (292 mg, 104%) as a colorless oil which was used without further purification. MS(ESI) m/z 278.1 (M+H).

34B. (3R,4S)-tert-Butyl 3-((3-(methoxycarbonyl)phenoxy)methyl)-4-phenylpyrrolidine-1-carboxylate

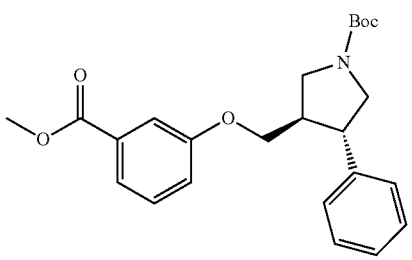 [SMILES: COC(=O)c1cccc(OC[C@H]2CN(C(=O)OC(C)(C)C)C[C@@H]2c2ccccc2)c1]

34B was prepared from 34A and methyl 3-hydroxybenzoate using a similar procedure to that described for 25A. MS(ESI) m/z 412.1 (M+H).

34C. (3R,4S)-tert-Butyl 3-((3-(hydroxymethyl)phenoxy)methyl)-4-phenylpyrrolidine-1-carboxylate

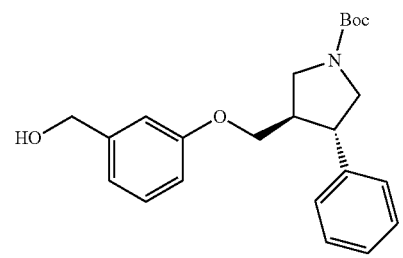 [SMILES: CC(C)(C)OC(=O)N1C[C@H](COc2cccc(CO)c2)[C@@H](c2ccccc2)C1]

34C was prepared from 34B following the procedure described for 10D. MS(ESI) m/z 384.2 (M+H).

34D. 1-(3-(((3R,4S)-4-Phenylpyrrolidin-3-yl)methoxy)benzyl)-4-(4,4,5,5-tetramethyl-1,3,2-dioxaborolan-2-yl)-1H-pyrazole, HCl

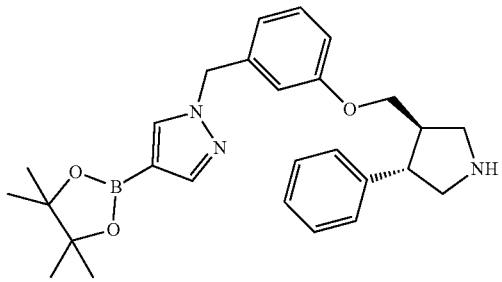 [SMILES: CC1(C)OB(c2cnn(Cc3cccc(OC[C@H]4CNC[C@@H]4c4ccccc4)c3)c2)OC1(C)C]

34D was prepared from 34C in two steps following the procedures described for 9D and 9E. MS(ESI) m/z 460.1 (M+H).

34E. 7-((Z)-1-Iodo-3-((3S,4R)-3-phenyl-4-((3-((4-(4,4,5,5-tetramethyl-1,3,2-dioxaborolan-2-yl)-1H-pyrazol-1-yl)methyl)phenoxy)methyl)pyrrolidin-1-yl)prop-1-en-1-yl)-N,3-ditrityl-3H-[1,2,3]triazolo[4,5-b]pyridin-5-amine

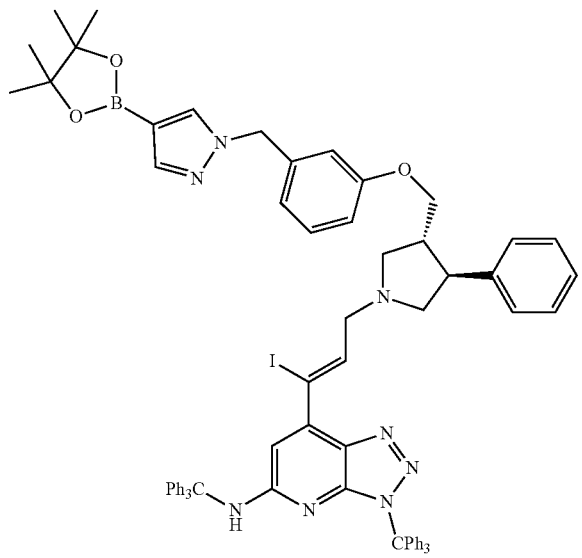

To a solution of Intermediate 8 (50 mg, 0.063 mmol) in DCM (1 mL) was added 34D (31 mg, 0.063 mmol) under nitrogen. The mixture was stirred for ~15 min, followed by addition of sodium triacetoxyborohydride (16 mg, 0.075 mmol). Stirring was continued at rt for 1 h. Purification of the reaction mixture by flash chromatography provided 34E (33 mg, 43%) as a yellow oil. MS(ESI) m/z 1243.3 (M+H).

Example 34 was prepared from 34E following the steps described for the preparation of Ex. 7 from 7G. MS(ESI) m/z 507.3 (M+H). $^1$H NMR (500 MHz, CD$_3$OD) δ 7.74 (s, 1H), 7.65 (s, 1H), 7.46-7.39 (m, 2H), 7.38-7.29 (m, 4H), 7.10 (br d, J=7.2 Hz, 1H), 6.94 (br d, J=7.2 Hz, 1H), 6.56 (br s, 1H), 6.29 (br s, 1H), 5.50 (d, J=15.4 Hz, 1H), 5.31 (d, J=15.7 Hz, 1H), 4.34 (br d, J=12.1 Hz, 1H), 4.19 (br d, J=12.7 Hz, 1H), 4.07 (br d, J=12.4 Hz, 1H), 3.85 (br s, 1H), 3.79-3.66 (m, 4H), 3.14-3.03 (m, 1H), 2.76-2.69 (m, 2H), 2.66 (br d, J=8.5 Hz, 1H), 2.55-2.39 (m, 1H). Analytical HPLC RT=5.07 min (Method A).

Example 35

2-(7-{15-Amino-3H-[1,2,3]triazolo[4,5-b]pyridin-7-yl}-18-oxa-3,4,10-triazatetracyclo[17.3.1.1$^{3,6}$.1$^{13,17}$]pentacosa-1(23),4,6(25),13,15,17(24),19,21-octaen-10-yl)acetamide, TFA

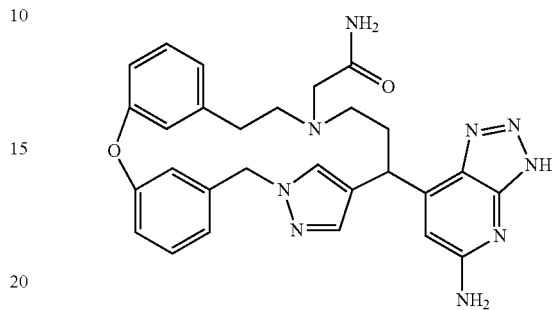

35A. tert-Butyl 3-bromophenethylcarbamate

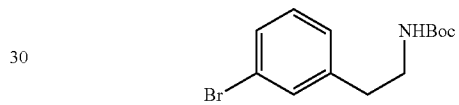

Sodium bicarbonate (0.983 g, 11.7 mmol) was added to a solution of 2-(3-bromophenyl)ethanamine (1.17 g, 5.85 mmol) and di-tert-butyl dicarbonate (1.63 ml, 7.02 mmol) in THF (15 ml), and the reaction mixture was stirred at rt ON. The mixture was diluted with EtOAc, washed with water and brine, dried over Na$_2$SO$_4$ and concentrated. The crude product was purified by flash chromatography to yield 35A (1.74 g, 99%) as a clear oil. $^1$H NMR (500 MHz, CDCl$_3$) δ 7.37-7.35 (m, 1H), 7.35 (s, 1H), 7.22-7.14 (m, 1H), 7.14-7.08 (m, 1H), 4.53 (br s, 1H), 3.46-3.27 (m, 2H), 2.77 (br t, J=6.9 Hz, 2H), 1.44 (s, 9H).

35B. Methyl 3-(3-(2-((tert-butoxycarbonyl)amino)ethyl)phenoxy)benzoate

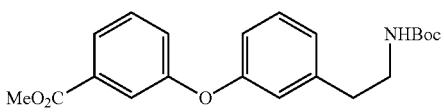 [SMILES: COC(=O)c1cccc(Oc2cccc(CCNC(=O)OC(C)(C)C)c2)c1]

35A (1.74 g, 5.81 mmol) and methyl 3-hydroxybenzoate (0.928 g, 6.10 mmol) were dissolved in dioxane (23 ml). To the resulting solution were added cesium carbonate (5.68 g, 17.4 mmol), CuI (1.11 g, 5.81 mmol) and 2-(dimethylamino)acetic acid (0.599 g, 5.81 mmol). Ar was bubbled through solution for 5 min, and then the reaction mixture was heated at 105° C. ON under argon. The mixture was cooled to rt and diluted with EtOAc (15 mL), washed with 1N HCl and brine. The organic layer was concentrated and the residue was purified by flash chromatography to provide 35B (1.19 g, 55.1%). MS (ESI) m/z 372.0 (M+H).

35C. tert-Butyl 3-(3-(hydroxymethyl)phenoxy)phenethylcarbamate

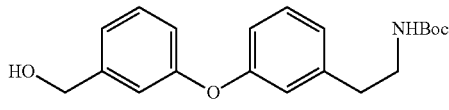 [SMILES: CC(C)(C)OC(=O)NCCc1cccc(Oc2cccc(CO)c2)c1]

35C was prepared from 35B by reduction with LiBH₄ as described for 10D. MS (ESI) m/z 344.1 (M+H).

35D. 2-(3-(3-((4-(4,4,5,5-Tetramethyl-1,3,2-dioxaborolan-2-yl)-1H-pyrazol-1-yl)methyl)phenoxy)phenyl)ethanamine, HCl

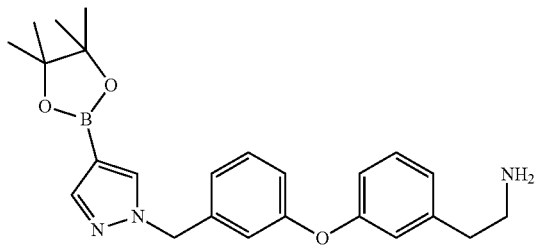 [SMILES: CC1(C)OB(c2cnn(Cc3cccc(Oc4cccc(CCN)c4)c3)c2)OC1(C)C]

35D was prepared from 35C using the Mitsunobu procedure described for 9D followed by deprotection with HCl in dioxane as described for 9E. MS (ES): m/z 420.1 (M+H).

35E. (Z)-7-(1-Iodo-3-((3-(3-((4-(4,4,5,5-tetramethyl-1,3,2-dioxaborolan-2-yl)-1H-pyrazol-1-yl)methyl)phenoxy)phenethyl)amino)prop-1-en-1-yl)-N,3-ditrityl-3H-[1,2,3]triazolo[4,5-b]pyridin-5-amine To a solution of 35D (0.10 g, 0.25 mmol) in DMF (0.55 mL) was added cesium hydroxide monohydrate (86 mg, 0.51 mmol), and the mixture was stirred at rt for 30 min, before KI (28 mg, 0.17 mmol) and Intermediate 3 (148 mg, 0.171 mmol) were added. The reaction mixture was stirred for an additional 10 min, then filtered to removed the solids, which were washed 2× with EtOAc. The filtrate was concentrated to provide 35E (0.22 g, 106%) which was used purification in the next step. MS (ESI) m/z 1203.2 (M+H).

35F. 7-((14Z,10Z)-11H-4-oxa-8-aza-1(1,4)-pyrazola-3,5(1,3)-dibenzenacycloundecaphan-10-en-11-yl)-N,3-ditrityl-3H-[1,2,3]triazolo[4,5-b]pyridin-5-amine

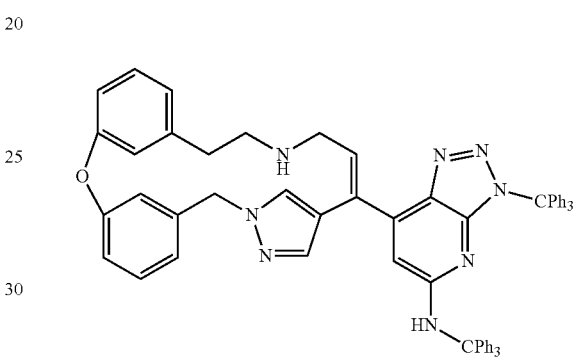

A mixture of 35E (0.20 g, 0.17 mmol), PdCl₂(dppf)-CH₂Cl₂ Adduct (68 mg, 0.083 mmol) and K₂CO₃ (0.12 g, 0.83 mmol) was degassed and back-filled with argon 3×. Degassed dioxane (60 mL) and H₂O (9.3 mL) were then added. The resulting reaction mixture was stirred at 85° C. for 3.5 h. The reaction was cooled to rt and filtered through Celite. The solids were washed with EtOAc, and the combined filtrate was concentrated. The residue was purified by flash chromatography to provide 35F (55.4 mg, 35.1% yield). MS (ESI) m/z 949.3 (M+H).

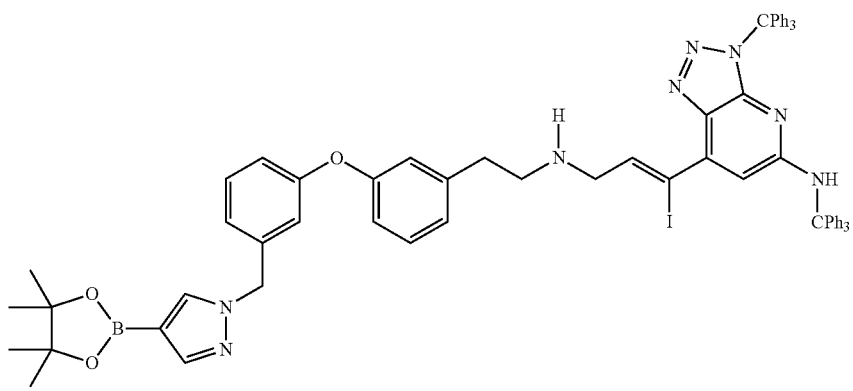

35G. 2-((14Z,10Z)-11-(3-Trityl-5-(tritylamino)-3H-[1,2,3]triazolo[4,5-b]pyridin-7-yl)-11H-4-oxa-8-aza-1(1,4)-pyrazola-3,5(1,3)-dibenzenacycloundecaphan-10-en-8-yl)acetamide

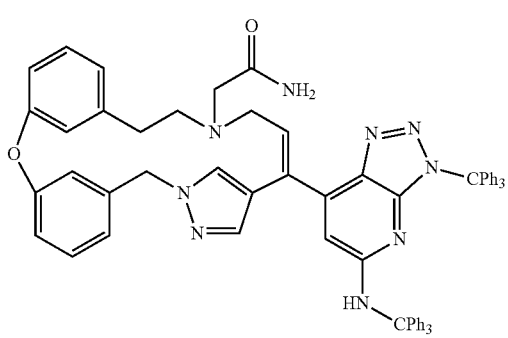

35F (55 mg, 0.058 mmol) was dissolved in DMF (0.75 mL) and Et$_3$N (0.016 mL, 0.12 mmol) was added, followed by 2-iodoacetamide (13 mg, 0.070 mmol). The reaction mixture was concentrated to provide 35G which was used crude in the next step. MS (ESI) m/z 1006.4 (M+H).

Example 35 was prepared from 35G by trityl deprotection and hydrogenation using the procedure described for Example 7. MS (ESI) m/z 525.2 (M+H). $^1$H NMR (500 MHz, CD$_3$OD) δ 7.78 (s, 1H), 7.56 (s, 1H), 7.48-7.37 (m, 2H), 7.28-7.19 (m, 1H), 7.16-7.09 (m, 2H), 7.08-7.00 (m, 1H), 6.72 (s, 1H), 6.50 (s, 1H), 6.48-6.41 (m, 1H), 5.28 (s, 2H), 4.41-4.29 (m, 1H), 4.06 (br. s., 2H), 3.64-3.54 (m, 1H), 3.50-3.39 (m, 1H), 3.07-2.90 (m, 4H), 2.66-2.46 (m, 2H). Analytical HPLC RT=4.53 min (Method A).

Example 36

7-{12,12-Difluoro-18-oxa-3,4,10-triazatetracyclo[17.3.1.1$^{3,6}$.1$^{13,17}$]pentacosa-1(23),4,6(25),13,15,17(24),19,21-octaen-7-yl}-3H-[1,2,3]triazolo[4,5-b]pyridin-5-amine, 2TFA

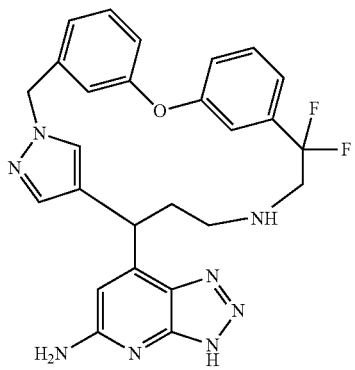 [SMILES: Nc1cc(C2CCNCC(F)(F)c3cccc(c3)Oc3cccc(c3)Cn3cc2cn3)c2nn[nH]c2n1]

36A. tert-Butyl (2-(3-bromophenyl)-2-oxoethyl)carbamate

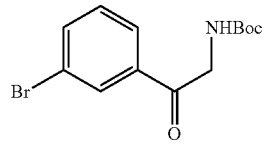 [SMILES: CC(C)(C)OC(=O)NCC(=O)c1cccc(Br)c1]

36A was prepared from 2-amino-1-(3-bromophenyl)ethanone hydrochloride using a similar procedure to that described for 34A. MS(ESI) m/z 313.9 (M+H).

36B. tert-Butyl (2-(3-bromophenyl)-2,2-difluoroethyl)carbamate

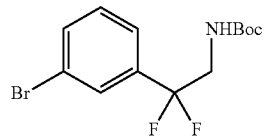 [SMILES: CC(C)(C)OC(=O)NCC(F)(F)c1cccc(Br)c1]

Deoxofluor (2.8 mL, 15 mmol) was added dropwise at 0° C. to a solution of 36B (0.96 g, 3.1 mmol) in DCM (5 mL). The reaction mixture was stirred at rt ON. The reaction mixture was quenched by addition of saturated aq. NaHCO$_3$ (60 mL) dropwise at 0° C. until the gas evolution ceased. The mixture was then extracted with DCM (3×). The organic layer was washed with brine, dried over Na$_2$SO$_4$, filtered and evaporated. The crude product was purified by flash chromatography to provide 36B (283 mg, 27%). MS (ESI) m/z 301.9 (M+Na-tBu).

Example 36 was prepared from 36B in 7 steps following the procedures described above for 35B, 10D, 9D, 9E, 34E, 7G and Ex. 7. MS(ESI) m/z 503.2 (M+H). $^1$H NMR (500 MHz, CD$_3$OD) δ 7.81 (s, 1H), 7.67-7.57 (m, 1H), 7.54 (s, 1H), 7.49-7.43 (m, 2H), 7.31 (dd, J=8.1, 2.1 Hz, 1H), 7.26 (d, J=8.0 Hz, 1H), 7.20-7.11 (m, 1H), 7.03 (s, 1H), 6.55 (s, 1H), 6.32 (d, J=1.7 Hz, 1H), 5.30 (s, 2H), 4.42 (dd, J=10.6, 4.5 Hz, 1H), 4.01-3.90 (m, 1H), 3.90-3.78 (m, 1H), 3.21-3.07 (m, 1H), 2.72-2.62 (m, 1H), 2.58-2.43 (m, 2H). FNMR −77.27 ppm. Analytical HPLC RT=4.87 min (Method A).

Example 37

7-[10-(2-Methoxyethyl)-18-oxa-3,4,10-triazatetracyclo[17.3.1.1³,⁶.1¹³,¹⁷]pentacosa-1(23),4,6(25),13,15,17(24),19,21-octaen-7-yl]-3H-[1,2,3]triazolo[4,5-b]pyridin-5-amine, 2TFA

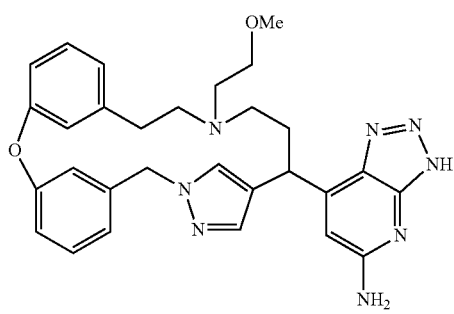 [SMILES: COCCN1CCc2cccc(c2)Oc2cccc(c2)Cn2cc(cn2)C(c2cc(N)nc3[nH]nnc23)CC1]

37A. N-(3-bromophenethyl)-2-methoxyethanamine

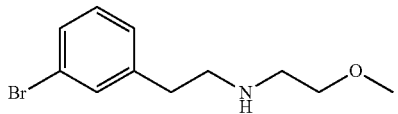

To a mixture of 2-(3-bromophenyl)ethanamine (485 mg, 2.42 mmol) and K$_2$CO$_3$ (469 mg, 3.39 mmol) in acetonitrile (7.3 mL) was added 1-bromo-2-methoxyethane (228 µL, 2.42 mmol), and the mixture was stirred ON at rt. The mixture was then heated at reflux for 6 h. An additional portion of 1-bromo-2-methoxyethane (75 µL, 0.80 mmol) was added, and heating was continued ON. The reaction mixture was filtered. The filtrate was concentrated, and residue purified by flash chromatography to provide 37A (189 mg, 30.2%). MS(ESI) m/z 257.9 (M+H).

Example 37 was prepared in 8 steps following the procedures described for 35A, 35B, 10D, 9D, 9E, 34E, 7G and Ex. 7. MS(ESI) m/z 525.2 (M+H). $^1$H NMR (500 MHz, CD$_3$OD) δ 7.78 (br. s., 1H), 7.55 (s, 1H), 7.47-7.36 (m, 2H), 7.28-7.20 (m, 1H), 7.17-7.08 (m, 2H), 7.07-7.01 (m, 1H), 6.76-6.69 (m, 1H), 6.54-6.46 (m, 1H), 6.46-6.38 (m, 1H), 5.28 (s, 2H), 4.44-4.29 (m, 1H), 3.79-3.69 (m, 2H), 3.67-3.55 (m, 1H), 3.53-3.44 (m, 2H), 3.44-3.38 (m, 4H), 3.12-2.89 (m, 4H), 2.61-2.49 (m, 2H). Analytical HPLC RT=5.21 min (Method A).

What is claimed is:

1. The compound of the formula

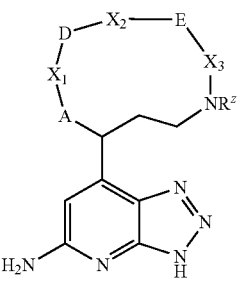

wherein
ring A is pyrazole substituted with 0-1 R$^1$;
R$^1$ is C$_{1-4}$ alkyl, C$_{1-4}$ haloalkyl or halogen;
X$_1$ is CH$_2$, or C$_{1-4}$ alkylene;
D is phenyl, pyridyl or pyrrolidinyl, all of which are substituted with 0-1 R$^2$,
R$^2$ is OH, halogen, C$_{1-4}$ alkyl, C$_{1-4}$ alkoxy or C$_{1-4}$ haloalkyl;
X$_2$ is a bond, C$_{1-4}$ alkylene substituted with 0-2 R$^3$, —O—, —OCH$_2$—, —CH$_2$O—, or —OCHR$^3$—;
R$^3$ is C$_{1-4}$ alkyl;
E is selected from a bond, phenyl, pyridyl, C$_3$-C$_8$ cycloalkyl or pyrrolidinyl, substituted with 0-2 R$^4$
R$^4$ is independently at each occurrence, halogen, C$_{1-4}$ alkoxy, C$_{1-4}$ haloalkoxy, phenyl or benzyl;
X$_3$ is a bond, C$_{1-4}$ alkyl substituted with 0-1 R$^5$ where R$^5$ is alkoxy, halogen, alkyl or hydroxyalkyl; or X$_3$ and NR$^z$ are taken together to form a pyrrolidinyl ring substituted with an aryl or aryl C$_{1-4}$ alkyl group;
R$^z$ is H, CH$_3$, CH$_2$CH$_2$OCH$_3$, CH$_2$CH$_2$OH, or CH$_2$CONH$_2$;
or a pharmaceutically acceptable salt, stereoisomer, tautomer or a solvate thereof.

2. A compound according to claim 1 of the formula

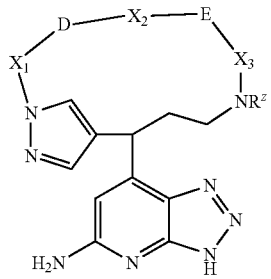

wherein
X$_1$ is CH$_2$, or C$_{1-4}$ alkylene;
D is phenyl, pyridyl or pyrrolidinyl, all of which are substituted with 0-1 R$^2$,
R$^2$ is OH, halogen, C$_{1-4}$ alkyl, C$_{1-4}$ alkoxy or C$_{1-4}$ haloalkyl;
X$_2$ is a bond, C$_{1-4}$ alkylene substituted with 0-1 R$^3$, —O—, —OCH$_2$—, —CH$_2$O—, or —OCHR$^3$—;
R$^3$ is C$_{1-4}$ alkyl;
E is selected from a bond, phenyl, pyridyl, C$_3$-C$_8$ cycloalkyl or pyrrolidinyl, substituted with 0-2 R$^4$ $R^4$ is independently at each occurrence, halogen, $C_{1-4}$ alkoxy, $C_{1-4}$ haloalkoxy, phenyl or benzyl;

$X_3$ is a bond, $C_{1-4}$ alkyl substituted with 0-1 $R^5$ where $R^5$ is alkoxy, halogen, alkyl or hydroxyalkyl; or $X^3$ and $NR^z$ are taken together to form a pyrrolidinyl ring substituted with an aryl or aryl $C_{1-4}$ alkyl group;

or $X_3$ and $NR^z$ are taken together to form a pyrrolidinyl ring substituted with an aryl or aryl $C_{1-4}$ alkyl or group;

$R^z$ is H, $CH_3$, $CH_2CH_2OCH_3$, $CH_2CH_2OH$, or $CH_2CONH_2$;

or a pharmaceutically acceptable salt, stereoisomer, tautomer or a solvate thereof.

3. A compound according to claim 2 wherein
$X_1$ is $CH_2$ or $CH_2CH_2$—;
D is phenyl;
$X_2$ is $C_{1-4}$ alkylene, —O—, —OCH$_2$— or —CH$_2$O;
E is a phenyl or $C_3$-$C_8$ cycloalkyl, substituted with 0-2 $R^4$;
$R^4$ is F, Cl, methoxy, $CF_3$ or benzyl;
$X_3$ is a bond or $C_{1-2}$ alkyl;
or a pharmaceutically acceptable salt, stereoisomer, tautomer or a solvate thereof.

4. A compound selected from
7-{17-oxa-3,4,10-triazatetracyclo[16.3.1.1$^{3,6}$.1$^{12,1^6}$]tetracosa-1(22),4,6(24),12,14,16(23), 18,20-octaen-7-yl}-3H-[1,2,3]triazolo[4,5-b]pyridin-5-amine, 7-{18-oxa-3,4,10-triazatetracyclo[17.3.1.1$^{3,6}$.1$^{13,1^7}$]pentacosa-1(23),4,6(25),13,15,17(24),19,21-octaen-7-yl}-3H-[1,2,3]triazolo[4,5-b]pyridin-5-amine, 7-{18-oxa-3,4,10-triazatetracyclo[17.3.1.1$^{3,6}$.1$^{13,1^7}$]pentacosa-1(23),4,6(25),13,15,17(24),19,21-octaen-7-yl}-3H-[1,2,3]triazolo[4,5-b]pyridin-5-amine, 7-{18-oxa-3,4,10-triazatetracyclo[17.3.1.1$^{3,6}$.1$^{13,1^7}$]pentacosa-1(23),4,6(25),13,15,17(24),19,21-octaen-7-yl}-3H-[1,2,3]triazolo[4,5-b]pyridin-5-amine, 7-{10-methyl-17-oxa-3,4,10-triazatetracyclo[16.3.1.1$^{3,6}$.1$^{12,1^6}$]tetracosa-1(22),4,6(24),12,14,16(23), 18,20-octaen-7-yl}-3H-[1,2,3]triazolo[4,5-b]pyridin-5-amine, 7-{18-oxa-3,4,10-triazatetracyclo[17.3.1.1$^{3,6}$.1$^{12,1^6}$]pentacosa-1(23),4,6(25),12,14,16(24), 19,21-octaen-7-yl}-3H-[1,2,3]triazolo[4,5-b]pyridin-5-amine, 7-[(17R)-18-phenyl-16-oxa-2,8,9-triazapentacyclo[16.2.2.1$^{1,1^7}$.1$^{6,9}$.1$^{11,1^3}$]pentacosa-6(25),7,11(24),12,14-pentaen-5-yl]-3H-[1,2,3]triazolo[4,5-b]pyridin-5-amine, 7-[(17S)-18-phenyl-16-oxa-2,8,9-triazapentacyclo[16.2.2.1$^{1,1^7}$.1$^{6,9}$.1$^{11,1^3}$]pentacosa-6(25),7,11(24),12,14-pentaen-5-yl]-3H-[1,2,3]triazolo[4,5-b]pyridin-5-amine, 7-[(3S,4S)-4-benzyl-2-oxa-6,12,13-triazatetracyclo[13.3.1.1$^{3,6}$.1$^{10,1^3}$]henicosa-1(18),10(20),11,15(19),16-pentaen-9-yl]-3H-[1,2,3]triazolo[4,5-b]pyridin-5-amine, 7-{14-oxa-3,4,10-triazatricyclo[13.3.1.1$^{3,6}$]icosa-1(19), 4,6(20), 15,17-pentaen-7-yl}-3H-[1,2,3]triazolo[4,5-b]pyridin-5-amine, 7-{14'-oxa-3',4',10'-triazaspiro[cyclopropane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 7-{14'-oxa-3',4',10'-triazaspiro[cyclopropane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 7-{14'-oxa-3',4',10'-triazaspiro[cyclopentane-1,12'-tricyclo[13.3.1.1$^{3,6}$]icosane]-1'(19'),4',6'(20'),15',17'-pentaen-7'-yl}-3H-[1,2,3]triazolo[4,5-b]pyridin-5-amine, 7-[(3R,4S,6S,10R)-4-benzyl-2-oxa-7,13,14-triazatetracyclo[14.3.1.1$^{3,6}$.1$^{11,1^4}$]docosa-1(19), 11(21),12,16(20),17-pentaen-10-yl]-3H-[1,2,3]triazolo[4,5-b]pyridin-5-amine, 7-[(3R,4S,6S,10S)-4-benzyl-2-oxa-7,13,14-triazatetracyclo[14.3.1.1$^{3,6}$.1$^{11,1^4}$]docosa-1(19),11(21),12,16(20),17-pentaen-10-yl]-3H-[1,2,3]triazolo[4,5-b]pyridin-5-amine, 7-{8,9,15-triazatetracyclo[16.3.1.1$^{2,6}$.1$^{8,11}$]tetracosa-1(22),2,4,6(24),9,11(23),18,20-octaen-12-yl}-3H-[1,2,3]triazolo[4,5-b]pyridin-5-amine, 7-{3-oxa-10,11,17-triazatetracyclo[16.2.2.1$^{4,8}$.1$^{10,13}$]tetracosa-4,6,8(24),11,13(23)-pentaen-14-yl}-3H-[1,2,3]triazolo[4,5-b]pyridin-5-amine, 7-{15,22-difluoro-18-oxa-3,4,10-triazatetracyclo[17.3.1.1$^{3,6}$.1$^{12,1^6}$]pentacosa-1(23),4,6(25),12,14,16(24), 19,21-octaen-7-yl}-3H-[1,2,3]triazolo[4,5-b]pyridin-5-amine, 7-[(18S)-19-phenyl-17-oxa-2,8,9-triazapentacyclo[17.2.2.1$^{1,1^8}$.1$^{6,9}$.1$^{12,1^6}$]hexacosa-6(26),7,12(25),13,15-pentaen-5-yl]-3H-[1,2,3]triazolo[4,5-b]pyridin-5-amine, 7-{2-oxa-7,13,14-triazatetracyclo[14.3.1.1$^{3,6}$.1$^{11,1^4}$]docosa-1(19),11(21),12,16(20),17-pentaen-10-yl}-3H-[1,2,3]triazolo[4,5-b]pyridin-5-amine, 7-[(17R)-17-methyl-18-oxa-3,4,10-triazatetracyclo[17.3.1.1$^{3,6}$. 1$^{12,1^6}$]pentacosa-1(23),4,6(25),12,14,16(24), 19,21-octaen-7-yl]-3H-[1,2,3]triazolo[4,5-b]pyridin-5-amine, 7-{17-oxa-3,4,10-triazatetracyclo[17.3.1.1$^{3,6}$.1$^{12,1^6}$]pentacosa-1(23),4,6(25),12,14,16(24), 19,21-octaen-7-yl}-3H-[1,2,3]triazolo[4,5-b]pyridin-5-amine, 7-[(11R,14R)-16-oxa-3,4,10-triazatetracyclo[15.3.1.1$^{3,6}$.1$^{11,1^4}$]tricosa-1(21),4,6(23),17,19-pentaen-7-yl]-3H-[1,2,3]triazolo[4,5-b]pyridin-5-amine,

[(11S)-7-{5-amino-3H-[1,2,3]triazolo[4,5-b]pyridin-7-yl}-18-oxa-3,4,10-triazatetracyclo[17.3.1.1$^{3,6}$.1$^{13,1^7}$]pentacosa-1(23),4,6(25),13,15,17(24),19,21-octaen-1-yl]methanol, 7-{14-fluoro-17-oxa-3,4,10-triazatetracyclo[17.3.1.1$^{3,6}$.1$^{12,1^6}$]pentacosa-1(23),4,6(25), 12(24), 13,15,19,21-octaen-7-yl}-3H-[1,2,3]triazolo[4,5-b]pyridin-5-amine, 7-{15-fluoro-17-oxa-3,4,10-triazatetracyclo[17.3.1.1$^{3,6}$.1$^{12,1^6}$]pentacosa-1(23),4,6(25), 12(24),13,15,19,21-octaen-7-yl}-3H-[1,2,3]triazolo[4,5-b]pyridin-5-amine, 7-{14-chloro-17-oxa-3,4,10-triazatetracyclo[17.3.1.1$^{3,6}$.1$^{12,1^6}$]pentacosa-1(23),4,6(25), 12(24), 13,15,19,21-octaen-7-yl}-3H-[1,2,3]triazolo[4,5-b]pyridin-5-amine, 7-{18-oxa-3,4,10-triazatetracyclo[18.3.1.1$^{3,6}$.1$^{13,1^7}$]hexacosa-1(24),4,6(26), 13(25),14,16,20,22-octaen-7-yl}-3H-[1,2,3]triazolo[4,5-b]pyridin-5-amine, 7-[(11R)-11-methyl-18-oxa-3,4,10-triazatetracyclo[17.3.1.1$^{3,6}$.1$^{13,1^7}$]pentacosa-1(23),4,6(25),13,15,17(24), 19,21-octaen-7-yl]-3H-[1,2,3]triazolo[4,5-b]pyridin-5-amine, 7-[(11S)-11-methyl-i 8-oxa-3,4,10-triazatetracyclo[17.3.1.1$^{3,6}$.1$^{13,1^7}$]pentacosa-1(23),4,6(25),13,15,17(24), 19,21-octaen-7-yl]-3H-[1,2,3]triazolo[4,5-b]pyridin-5-amine, 7-[(17R)-17-(2-methylpropyl)-18-oxa-3,4,10-triazatetracyclo[17.3.1.1$^{3,6}$.1$^{12,1^6}$]pentacosa-1 (23),4,6(25),12,14,16(24),19,21-octaen-7-yl]-3H-[1,2,3]triazolo[4,5-b]pyridin-5-amine, 7-[(3R,4S,6S)-4-benzyl-2-oxa-7,13,14-triazatetracyclo[15.3.1.1$^{3,6}$.1$^{11,1^4}$]tricosa-1(20),11(22),12,17(21),18-pentaen-10-yl]-3H-[1,2,3]triazolo[4,5-b]pyridin-5-amine, 7-[(3R,4S,6S)-4-benzyl-2-oxa-7,13,14-triazatetracyclo[15.3.1.1$^{3,6}$.1$^{11,1^4}$]tricosa-1(20),11(22),12,17(21),18-pentaen-10-yl]-3H-[1,2,3]triazolo[4,5-b]pyridin-5-amine, 7-{5-amino-3H-[1,2,3]triazolo[4,5-b]pyridin-7-yl}-13-(2-phenylethyl)-3,4,10,13-tetraazatricyclo[13.3.1.1$^{3,6}$]icosa-1(19),4,6(20),15,17-pentaen-12-one, 7-{12,12-difluoro-18-oxa-3,4,10-triazatetracyclo[17.3.1.1$^{3,6}$.1$^{13,17}$]pentacosa-1(23),4,6(25),13,15,17(24),19,21-octaen-7-yl}-3H-[1,2,3]triazolo[4,5-b]pyridin-5-amine, or a stereoisomer, a tautomer, or a pharmaceutically acceptable salt thereof.

5. A pharmaceutical composition, comprising a pharmaceutically acceptable carrier and a compound of any one of claims 1-4, or a stereoisomer, a tautomer, or a pharmaceutically acceptable salt thereof.

\* \* \* \* \*